(12) United States Patent
Patel et al.

(10) Patent No.: US 11,337,987 B1
(45) Date of Patent: May 24, 2022

(54) COMPOSITIONS AND METHODS FOR TREATING CENTRAL NERVOUS SYSTEM DISORDERS

(71) Applicant: Lipocine Inc., Salt Lake City, UT (US)

(72) Inventors: Mahesh V. Patel, Salt Lake City, UT (US); Nachiappan Chidambaram, Sandy, UT (US); Kilyoung Kim, West Jordan, UT (US); Kongnara Papangkorn, Sandy, UT (US); Benjamin J. Bruno, Salt Lake City, UT (US); Kiran Kumar Vangara, Riverton, UT (US)

(*) Notice: Subject to any disclaimer, the term of this patent is extended or adjusted under 35 U.S.C. 154(b) by 0 days.

(21) Appl. No.: 17/314,883

(22) Filed: May 7, 2021

(51) Int. Cl.
*A61K 31/57* (2006.01)
*A61K 9/00* (2006.01)
*A61P 25/24* (2006.01)
*A61K 9/48* (2006.01)

(52) U.S. Cl.
CPC ............ *A61K 31/57* (2013.01); *A61K 9/0053* (2013.01); *A61P 25/24* (2018.01); *A61K 9/0095* (2013.01); *A61K 9/4825* (2013.01)

(58) Field of Classification Search
CPC ........ A61K 31/57; A61K 9/0053; A61P 25/24
See application file for complete search history.

(56) References Cited

U.S. PATENT DOCUMENTS

| | | | |
|---|---|---|---|
| 4,900,734 A | 2/1990 | Maxson | 514/171 |
| 5,645,856 A | 7/1997 | Lacy | 424/455 |
| 6,267,985 B1 | 7/2001 | Chen | 424/451 |
| 6,294,192 B1 | 9/2001 | Patel | 424/451 |

(Continued)

FOREIGN PATENT DOCUMENTS

| | | | |
|---|---|---|---|
| WO | WO2001001960 | 1/2001 | A61K 9/08 |
| WO | WO2017173044 | 10/2017 | A61K 31/57 |

OTHER PUBLICATIONS

Andreen et al., Allopregnanolone Concentration and Mood—a Bimodal Association in Postmenopausal Women Treated with Oral Progesterone, Psychopharmacology, May 25, 2006, vol. 187, pp. 209-221.

(Continued)

*Primary Examiner* — San Ming R Hui

(74) *Attorney, Agent, or Firm* — Michael R. Schramm

(57) ABSTRACT

The present disclosure is drawn to compositions and methods for treating CNS disorders. In one embodiment, an oral pharmaceutical composition can comprise a therapeutically effective amount of pregn-4-ene-3,20-dione; and a pharmaceutically acceptable carrier that provides formation of either 3α-OH-5α-pregnan-20-one, or 3α-OH-5β-pregnan-20-one, or both in an amount sufficient to treat a CNS disorder when orally administered to a subject. In another embodiment, a method of treating a CNS disorder can comprise orally administering to a subject, a therapeutically effective amount of pregn-4-ene-3,20-dione that provides an amount of GABA receptor binding pregn-4-ene-3,20-dione metabolites that is sufficient to treat the CNS disorder. In another embodiment, a method of treating a CNS disorder can comprise orally administering to the subject, a therapeutically effective amount of pregn-4-ene-3,20-dione that provides an amount of 3α-OH-5α-pregnan-20-one, or 3α-OH-5β-pregnan-20-one, or both that is sufficient to treat the CNS disorder.

26 Claims, 3 Drawing Sheets

(56) References Cited

U.S. PATENT DOCUMENTS

| | | | |
|---|---|---|---|
| 6,309,663 B1 | 10/2001 | Patel | 424/450 |
| 6,458,383 B2 | 10/2002 | Chen | 424/451 |
| 6,544,553 B1 | 4/2003 | Hsia | 424/465 |
| 6,761,903 B2 | 7/2004 | Chen | 424/451 |
| 6,982,281 B1 | 1/2006 | Chen | 514/458 |
| 6,987,101 B1 | 1/2006 | Nashed | 514/171 |
| 7,374,779 B2 | 5/2008 | Chen | 424/451 |
| 8,633,178 B2 | 1/2014 | Bernick | 514/169 |
| 9,084,797 B2 | 7/2015 | Caufriez | A61K 31/57 |
| 9,375,437 B2 | 6/2016 | Nachaegari | A61K 31/57 |
| 9,795,617 B2 | 10/2017 | Baucom | A61K 31/57 |
| 9,931,349 B2 | 4/2018 | Shadiack | A61K 31/57 |
| 10,052,386 B2 | 8/2018 | Bernick | A61K 47/14 |
| 10,286,077 B2 | 5/2019 | Shadiack | A61K 47/26 |
| 10,328,087 B2 | 6/2019 | Thorsteinsson | A61K 31/573 |
| 10,471,148 B2 | 11/2019 | Cacace | A61K 47/14 |
| 10,774,108 B2 | 9/2020 | Martinez Botella | C07J 41/0055 |
| 10,806,740 B2 | 10/2020 | Periscaner | A61K 31/57 |
| 10,822,370 B2 | 11/2020 | Botella | C07J 43/003 |
| 2002/0012680 A1 | 1/2002 | Patel | 424/400 |
| 2003/0077297 A1 | 4/2003 | Chen | 424/400 |
| 2003/0104048 A1 | 6/2003 | Patel | 424/451 |
| 2003/0235595 A1 | 12/2003 | Chen | 424/400 |
| 2003/0236236 A1 | 12/2003 | Chen | 514/171 |
| 2005/0171193 A1 | 8/2005 | Chen | 514/458 |
| 2010/0136105 A1 | 6/2010 | Chen | 424/455 |
| 2010/0137271 A1 | 6/2010 | Chen | 514/181 |
| 2011/0142945 A1 | 6/2011 | Chen | 424/489 |
| 2011/0312927 A1 | 12/2011 | Nachaegari | 514/177 |
| 2011/0312928 A1 | 12/2011 | Nachaegari | 514/177 |
| 2013/0029947 A1 | 1/2013 | Nachaegari | 514/170 |
| 2015/0064243 A1 | 3/2015 | Chen | A61K 47/22 |
| 2015/0202211 A1 | 7/2015 | Amadio | A61K 31/27 |
| 2015/0374826 A1 | 12/2015 | Patel | A61K 47/14 |
| 2016/0015649 A1 | 1/2016 | Chen | A61K 9/4866 |
| 2016/0213687 A1 | 7/2016 | Nachaegari | A61K 31/57 |
| 2018/0125979 A1 | 5/2018 | Chen | A61K 47/22 |
| 2018/0264117 A1 | 9/2018 | Chen | A61K 47/22 |
| 2020/0282061 A1 | 9/2020 | Chen | A61K 47/22 |

OTHER PUBLICATIONS

Aufrere et al., Progesterone: An Overview and Recent Advances, JOPS, Jun. 1976, vol. 65, No. 6, pp. 783-800.

Barak et al., Progesterone Loading as a Strategy for Treating postpartum depression, Human Psychopharmacology Clinical and Experimental, Mar. 12, 2003, pp. 1-3.

Broekhoven et al., Oral Progesterone Decreases saccadic eye velocity and Increases Sedation in Women, PNEC, Aug. 28, 2006, pp. 1190-1199.

Coombes et al., Progestagens are Metabolized by the Gut Microbiota, Pharmaceutics, Aug. 12, 2008, vol. 12, No. 760, pp. 1-10.

De Lignieres, Influence of Route of Administration on Progesterone Metabolism, Maturitis, 1995, vol. 21, pp. 251-257.

FitzGerald et al., Progesterone to Prevent Postnatal Depression, AJOHP, 2000, vol. 30, No. 1, pp. 21-22.

Freeman et al., Anxiolytic Metabolites of Progesterone: Correlation with Mood and Performance Measures following Oral Progesterone, ClinNec, Aug. 18, 1993, vol. 58, pp. 478-484.

Freeman et al., A Placebo-Controlled Study of Effects of Oral Progesterone on Performance and Mood, BJCP, 1992, vol. 33, pp. 293-298.

Gordon et al., Efficacy of Transdermal Estradiol and Micronized Progesterone in the Prevention of Depressive Symptoms in the Menopause Transition, JAM Psychiatry, 2018, vol. 75, pp. 149-157.

Levine et al., Comparison of the Pharmacokinetics of Crinone 8% administered vaginally versus Prometrium Administered Orally in Postmenopausal Women, Fertility and Sterility, Mar. 2003, vol. 73, No. 3, pp. 516-521.

Murphy et al., Determination of Progesterone and Some of its Neuroactive Ring A-Reduced Metabolites in Human Serum, JSBMB, May 2006, vol. 74, pp. 137-142.

Timby et al., Pharmacokinetic and Behavioral Effects of Allopregnanolone in Healthy Women, Psychopharmacology, Sep. 21, 2005, vol. 186, pp. 414-424.

Unknown, Prometrium Warning Label, Abbott Labs, 2011, pp. 1-26.

Vanselow et al., Effects of Progesterone and its 5a and 5b metabolites on Symptoms of PMS According to Route of Administration, JPOG, 1996, vol. 17, pp. 29-38.

Wyatt et al., Efficacy of Progesterone in management of PMS, BMJ, Oct. 6, 2001, vol. 323, pp. 1-8.

ant to a subject. In another aspect, the composition or dosage form can include pregn-4-ene-3,20-dione in a form that enhances, increases, or maximizes formation of either 3α-OH-5α-pregnan-20-one, or 3α-OH-5β-pregnan-20-one, or both when orally administered to a subject. In another aspect, the composition or dosage form can include pregn-4-ene-3,20-dione with a carrier and/or in a form that modulates formation of either 3β-OH-5α-pregnan-20-one, or 3β-OH-5β-pregnan-20-one, or both, collectively referred to as negative allosteric modulators (NAMs) of $GABA_A$ receptor, when orally administered to a subject. For example, in one aspect, the pregn-4-ene-3,20-dione can be formulated with a carrier that when orally administered to a subject increases formation of either 3α-OH-5α-pregnan-20-one, or 3α-OH-5β-pregnan-20-one, or both as compared to an equivalent amount of pregn-4-ene-3,20-dione utilizing a purpose-inadequate carrier or compositions comprising micronized pregn-4-ene-3,20-dione when orally administered to the subject.

COMPOSITIONS AND METHODS FOR TREATING CENTRAL NERVOUS SYSTEM DISORDERS

FIELD OF THE DISCLOSURE

The present disclosure relates to compositions, dosage forms and regimens, and methods of treating a subject with a central nervous system (CNS) disorder. Accordingly, this disclosure involves the fields of chemistry, pharmaceutical sciences, medicine, and other health sciences.

BACKGROUND

CNS disorders are neurological disorders that can affect the structure or function of the brain or spinal cord. CNS disorders can have various causes including trauma, infections, degeneration, structural defects, tumors, autoimmune disorders, and strokes. Some examples include addiction, attention deficit hyperactivity disorder (ADHD), autism, epilepsy, multiple sclerosis, depression, anxiety, and the like. A wide range of treatments have been tried for CNS disorders ranging from surgery to neural rehabilitation to prescription medication. Depression is a mood disorder that can cause persistent feelings of sadness and anhedonia. Specific depression conditions such as Major Depressive Disorder or Clinical Depression, affect an individual feels, thinks and behaves, and can lead to a variety of further emotional and physical problems.

Perinatal depression or Postpartum depression (PPD) is a form of a major depression disorder affecting expectant and new mothers and is characterized by extreme sadness, difficulty bonding with the infant, low energy, anxiety, crying episodes, irritability, feelings of guilt and/or inadequacy, thoughts of self- and/or infant-harm, and changes in sleeping or eating patterns. Onset of PPD can range from the third trimester of pregnancy through about 4 weeks following childbirth. Current statistics show that PPD affects about 10% to 15% of women after childbirth. Treatment for PPD has included cognitive behavioral therapy, interpersonal therapy, antidepressant medication, electroconvulsive therapy, and light aerobic exercise. However, some studies have indicated that many antidepressant medications are insufficiently effective in treating PPD. Further, traditional antidepressants have slow onset, taking weeks to months to reach full efficacy. Therefore, better ways of treating PPD in general continue to be sought.

To-date an injectable (continuous intravenous infusion) brexanalone (i.e. allopregnalone) product marketed under the name ZULRESSO® is the only product approved in the United States for the indication of PPD in women of childbearing age. However, treatment requires hospitalization and the patient needs to be administered and monitored closely by a health care provider in a recognized health care setting under a risk evaluation and mitigation strategy (REMS). In addition to privacy and social stigma issues, the ZULRESSO® treatment protocol requires a patient's admission to a perinatal inpatient unit, which is demanding to a mother when she is still bonding with her newborn. Additional issues with ZULRESSO® treatment include the lengthy duration of therapy, needle phobia, vascular access injection site infection risk, potential repetitive needle sticks to find veins, etc. Furthermore, in view of its non-oral administration form, treatment with ZULRESSO® also presents cost, access, and logistics issues as well the need for a healthcare facility to spend significant time preparing to become treatment ready. Therefore, a significant unmet need exists for an oral composition and methods to treat a CNS depression disorder such as PPD. Utilizing pregn-4-ene-3,20-dione as an oral option to treat depression has been challenging either due to difficulty generating adequate serum PAM (Positive Allosteric Modulator of $GABA_A$ receptor (PAM) levels caused by ineffective dose and dosing regimens for oral delivery or because such compositions are typically formulated with a crystalline form of the active agent with deficient characteristics resulting in sub-therapeutics serum levels of PAMs.

SUMMARY

The present disclosure encompasses compositions and oral dosage forms and regimens including pregn-4-ene-3,20-dione and related methods. The compositions and oral dosage forms can be formulated to include a therapeutically effective amount of pregn-4-ene-3,20-dione and a pharmaceutically acceptable carrier. In one aspect, the pharmaceutically acceptable carrier of the composition or dosage form can provide formation of either 3α-OH-5β-pregnan-20-one, or 3α-OH-5α-pregnan-20-one or both, collectively referred to as positive allosteric modulators (PAMs or 3α metabolites) of $GABA_A$ receptor, in an amount sufficient to treat a CNS depression disorder when orally administered to a subject.

In yet another embodiment, there is provided compositions and oral dosage forms that include a therapeutically effective amount of pregn-4-ene-3,20-dione and a pharmaceutically acceptable carrier that provides increased formation of gamma aminobutyric acid (GABA) receptor binding/modulating PAMs as compared to an equivalent amount of pregn-4-ene-3,20-dione utilizing a purpose-inadequate carrier or compositions comprising micronized pregn-4-ene-3,20-dione when orally administered the subject.

In one embodiment, the composition can be formulated as an oral dosage form that has from about 10 mg to about 400 mg of pregn-4-ene-3,20-dione. In one aspect, the oral dosage form can be a solid, liquid, a semi-liquid or semi solid, a syrup, an emulsion, a dispersion, a suspension, a capsule, a sprinkle, a tablet, a chew, or a drink. In one aspect, some dosage forms can be administered by an injectable for infusion to a subject.

In yet another embodiment, a method of treating a CNS depression disorder in a subject can include orally administering a therapeutically effective amount of pregn-4-ene-3,20-dione to the subject. In one aspect, the therapeutically effective amount of pregn-4-ene-3,20-dione can provide an amount of 3α-OH-5α-pregnan-20-one, or 3α-OH-5β-pregnan-20-one, or both that is sufficient to treat the CNS depression disorder. In another aspect, the therapeutically effective amount of pregn-4-ene-3,20-dione can be in a form that provides a therapeutically effective amount of either 3α-OH-5α-pregnan-20-one, or 3α-OH-5β-pregnan-20-one, or a combination thereof for treating the CNS depression disorder in the subject. In yet another aspect, the pregn-4-ene-3,20-dione can be combined with a carrier that is sufficient to provide a therapeutically effective amount of either 3α-OH-5α-pregnan-20-one, or 3α-OH-5β-pregnan-20-one, or a combination thereof for treating the CNS depression disorder in the subject. In yet another aspect, the pregn-4-ene-3,20-dione can be combined with a carrier that is sufficient to provide a therapeutically effective amount of either 3β-OH-5α-pregnan-20-one, or 3β-OH-5β-pregnan-20-one, or both to modulate effects of either 3α-OH-5α-pregnan-20-one, or 3α-OH-5β-pregnan-20-one or both for treating the CNS depression disorder in the subject.

In yet another aspect, the pregn-4-ene-3,20-dione can be combined with a carrier that is sufficient to provide a therapeutically effective amount of either 3β-OH-5α-pregnan-20-one, or 3β-OH-5β-pregnan-20-one, or both to modulate effects of either 3α-OH-5α-pregnan-20-one, or 3α-OH-5β-pregnan-20-one or both for resulting in desired CNS activity in the subject.

BRIEF DESCRIPTION OF THE DRAWINGS

Features and advantages of invention embodiments will be apparent from the detailed description which follows, taken in conjunction with the accompanying drawings, which together illustrate, by way of example, features of the disclosure; and wherein.

Figure 1:
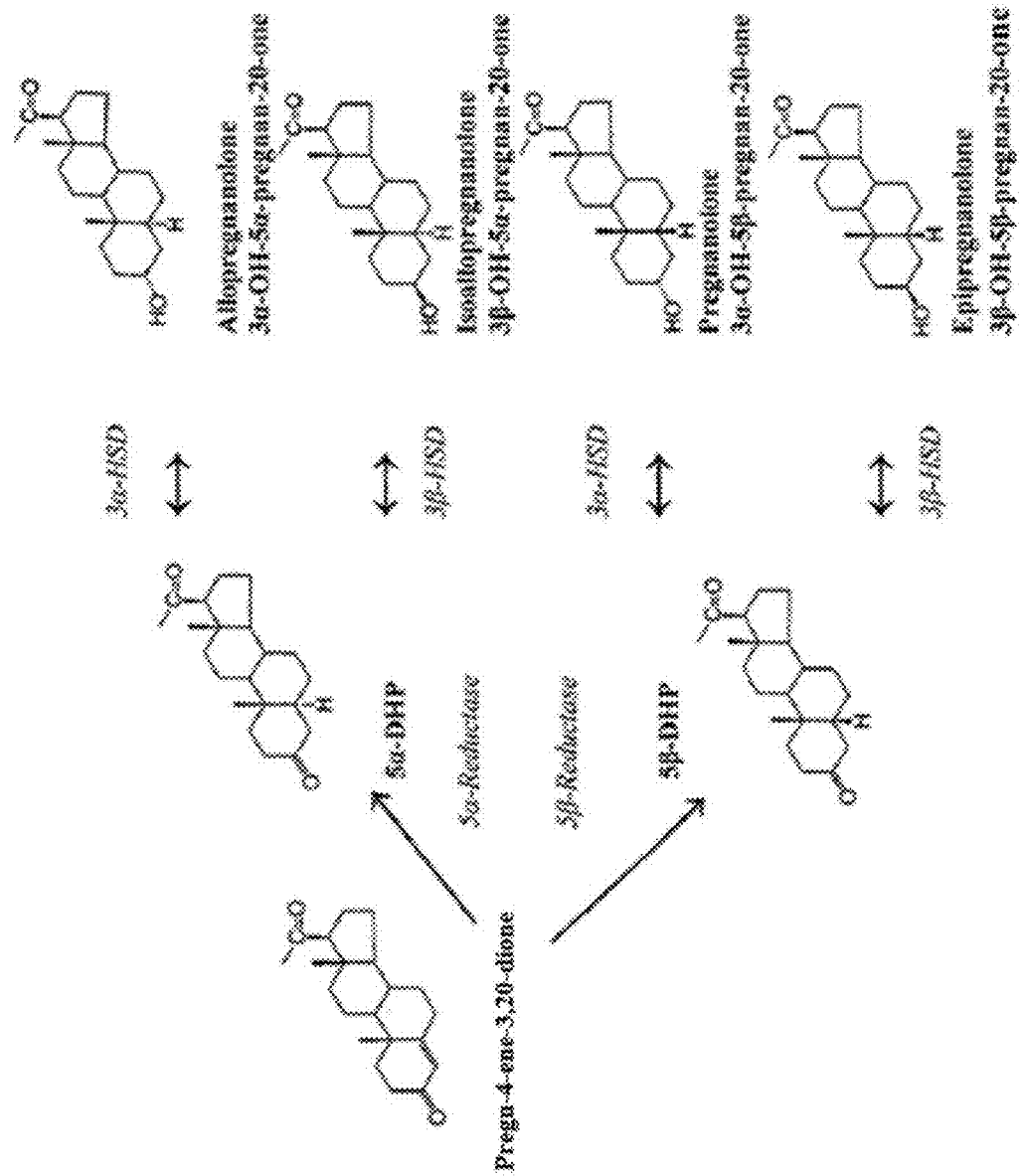
FIG. 1 depicts metabolic pathways of pregn-4-ene-3,20-dione in accordance with an example.

Reference will now be made to the exemplary embodiments illustrated, and specific language will be used herein to describe the same. It will nevertheless be understood that no limitation of the scope of the disclosure is thereby intended.

DETAILED DESCRIPTION

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein but are merely representative thereof.

Definitions

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, the terms "treat," "treatment," or "treating" and the like refers to administration of a therapeutic agent to a subject who is either asymptomatic or symptomatic. In other words, "treat," "treatment," or "treating" can refer to the act of reducing or eliminating a condition (i.e., symptoms manifested), or it can refer to prophylactic treatment (i.e., administering to a subject not manifesting symptoms in order to prevent their occurrence). Such prophylactic treatment can also be referred to as prevention of the condition, preventative action, preventative measures, and the like.

As used herein, the terms "therapeutic agent," "active agent," and the like can be used interchangeably and refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category in this written description, it is understood that such recitation is intended to include express support for the active agent per se, as well as pharmaceutically acceptable salts, esters or compounds significantly related thereto, including without limitation, prodrugs, isomers, and the like.

As used herein, the terms "formulation" and "composition" are used interchangeably and refer to a mixture of two or more compounds, elements, or molecules. In some aspects, the terms "formulation" and "composition" may be used to refer to a mixture of one or more active agents with a carrier or other excipients. Furthermore, the term "dosage form" can include one or more formulation(s) or composition(s) provided in a format for administration to a subject. For example, an "oral dosage form" can be suitable for administration to a subject's mouth. A "topical dosage form" can be suitable for administration to a subject's skin by rubbing, etc.

As used herein, "pharmaceutically acceptable carrier" or "carrier" are used interchangeably and refer to a pharmaceutically acceptable agent or ingredient that can be combined with an active agent as part of a composition or dosage form. In some aspects, pharmaceutically acceptable carriers can impact the form or behavior of an active agent. For example, in some aspects, a pharmaceutically acceptable carrier can be capable of fully or partially dissolving or solubilizing an active agent (e.g., pregn-4-ene-3,20-dione) in a pharmaceutical composition or enabling a non-crystalline amorphous form of the active agent. Further, in some aspects, the carrier can impact or control the properties and performance of the composition or dosage form. For example, in some aspects, a carrier can impact or control the pharmacokinetic performance or profile (e.g. release rate and/or extent of release of the active agent) of the composition and/or the dosage form.

As used herein, a "semi-liquid" or "semi-solid" corresponds to a partially solubilized active agent and a "liquid" corresponds to a fully solubilized active agent at room temperature. "Solid" corresponds to a fully solid active agent at room temperature.

As used herein, a "subject" refers to a mammal that may benefit from the administration of a drug composition, dosage form or dosage regimen, or method disclosed herein. Examples of subjects include humans, and may also include other animals such as horses, pigs, cattle, dogs, cats, rabbits, and aquatic mammals. In one specific aspect, a subject is a human. In another aspect, the subject is a female. In another aspect, the subject is a female is of childbearing age. In another aspect the female as delivered a baby within the last 12 months. In another aspect, the subject is male.

As used herein, "in need of treatment" and the like refers to a subject that has a disease, condition, or disorder or is suspected of having the disease, condition, or disorder according to various diagnostic criteria typically used in practice, or desires treatment or is indicated for treatment. Thus, "in need of treatment" can include the operation of identifying a subject in need of treatment.

As used herein, "identifying a subject in need of treatment" can include the operation of obtaining a biological sample from the subject and determining the level of one or more biomarkers as described herein, assessing a biological sample obtained from said subject, performing an imaging analysis on the subject, assessing one or more clinical characteristics of said subject (e.g., assessing symptoms or overt symptoms), or a combination thereof.

As used herein, the terms "illness," "disease," "condition," "symptom", and "disorder" can be used interchangeably and refer to an abnormality or incorrect functioning of any part, group, or system of a subject's physiology regardless of the causality thereof. For example, a mental illness or emotional disorder can be caused by environmental factors, genetic factors, physiologic events, past experiences, and other influences or combinations thereof.

As used herein, an "acute" condition refers to a condition that can develop rapidly and have distinct symptoms needing urgent or semi-urgent care. By contrast, a "chronic" condition refers to a condition that is typically slower to develop and lingers or otherwise progresses over time. Some examples of acute conditions can include without limitation, an asthma attack, bronchitis, a heart attack (myocardial infarction), pneumonia, and the like. Some examples of chronic conditions can include without limitation, arthritis, diabetes, hypertension, high cholesterol (hyperlipidemia), and the like.

The terms "serum levels," "serum amounts", "serum concentrations," "plasma levels," "plasma concentrations," "blood levels," and "blood concentrations" and the like can be used interchangeably herein and refer to the total amount of an identified analyte (e.g. identified metabolite or active agent), including free, bioavailable, and bound fractions in a subject's blood. For example, "serum 3α-OH-5α-pregnan-20-one" or "serum 3α-OH-5α-pregnan-20-one levels" or "serum 3α-OH-5α-pregnan-20-one concentration" or "plasma 3α-OH-5α-pregnan-20-one concentration" or "3α-OH-5α-pregnan-20-one concentration in the blood" refer the total 3α-OH-5α-pregnan-20-one concentration which is the sum of the 3α-OH-5α-pregnan-20-one fractions present including substantially free and bound 3α-OH-5α-pregnan-20-one concentrations. Likewise, the terms "serum 3α-OH-5β-pregnan-20-one" or "serum 3α-OH-5β-pregnan-20-one levels," "serum 3α-OH-5β-pregnan-20-one concentration," "plasma 3α-OH-5β-pregnan-20-one concentration," or "3α-OH-5β-pregnan-20-one concentration in the blood" are used interchangeably and refer the total 3α-OH-5β-pregnan-20-one concentration which is the sum of the 3α-OH-5β-pregnan-20-one fractions present including substantially free and bound 3α-OH-5β-pregnan-20-one concentrations. It should be understood that in this written description, such terms provide express support for total analyte or agent levels, as well as for the various applicable fractions thereof, including bioavailable, bound, and substantially free fractions. Unless otherwise specified, these values are "observed" concentrations or amounts without adjusting or correcting for the base-line serum levels in the subject(s). As with any bio-analytical measure, for increased consistency, the method employed to measure initial serum levels should be consistent with the method used to monitor and re-measure serum levels during clinical testing and therapy for a subject. As used herein, the term "$C_{avg}$," refers to an average serum concentration level for time 0 to t (e.g. average daily serum concentration level, daily $C_{avg}$, is calculated as ratio of $AUC_{0-24}/24$ hours) and the term "$C_{max}$," refers to a maximum serum concentration level post single dose administration.

Serum neurosteroid measurements for pregn-4-ene-3,20-dione, and its PAM or NAM metabolites based on an immunoassay are not accurate because the assay is typically not specific to the target analyte. To measure the target analyte, the assay should be based on chromatography-combined mass spectrometry method (e.g. LC-MS/MS or GC-MS), which can provide reliable data to assess the true pharmacokinetic and pharmacodynamic potential of pregn-4-ene-3,20-dione and its PAM and NAM metabolites. Consequently, data and results related to oral pregn-4-ene-3,20-dione and its neurosteroid, PAM (e.g., 3α-OH-5α-pregnan-20-one, 3α-OH-5β-pregnan-20-one) or NAM (e.g., 3β-OH-5α-pregnan-20-one, 3β-OH-5β-pregnan-20-one) metabolites are only reliable with respect to levels of neurosteroid generation or the adequacy of neurosteroid levels for desirable GABA receptor modulation when determined by analytical procedures that are amenable to the individual analyte separation step for specificity and accuracy, such as for liquid or gas chromatography, liquid chromatography-tandem mass spectrometry, or gas chromatography-mass spectrometry (LC-MS/MS or GC-MS).

In one aspect the pharmacokinetic values (e.g. serum concentrations, computed ratios) of an analyte of interest (e.g. pregn-4-ene-3,20-dione or a PAM, or a NAM), derived from the present compositions and methods are based on LC-MS/MS or GC-MS measurements.

As use herein with respect to physiologic levels of a given substance, the term "baseline" refers to a level or concentration of the substance, such as analyte of interest (e.g. pregn-4-ene-3,20-dione or a PAM, or a NAM), in a subject prior to administration of an active agent. For example, the baseline level of pregn-4-ene-3,20-dione in a subject would the subject's pregn-4-ene-3,20-dione serum level prior (e.g., just prior) to the commencement of pregn-4-ene-3,20-dione treatment.

The term "oral administration" represents any method of administration in which an active agent can be administered by swallowing, chewing, sucking, or drinking of the composition or dosage form. Oral administration can be intended for enteral delivery of an active agent or transmucosal delivery of the active agent. In some embodiments, the composition and dosage forms of the current disclosure can be admixed with food or drink prior to being orally consumed or can be otherwise co-administered with food.

As used herein, the terms "release" and "release rate" are used interchangeably to refer to the discharge or liberation of pregn-4-ene-3,20-dione from the composition or dosage form into a surrounding environment such as an aqueous medium either in vitro or in vivo.

As used herein, the terms "dissolution" refers to solubilization of the pregn-4-ene-3,20-dione into a surrounding environment such as an aqueous medium either in vitro or in vivo.

In some aspects, the release of the drug may be controlled release. As used herein, the term "controlled release" represents the release of the drug from the dosage form according to a predetermined profile. In some aspects, the controlled release selected can be, accelerated, intermediate, delayed, extended, sustained, pulsatile, gastric, enteric or colonic. Accelerated released may be obtained by for instance an increased rate of release of the drug, an increased susceptibility to metabolism in the Gastro-intestinal (GI) tract, and combinations thereof. In another aspect, combinations of the aforementioned release profiles may be used in order to achieve specific delivery results, such as an immediate release followed by a delayed and/or a sustained release of the active agent.

As used herein, a "dosing regimen" or "regimen" such as an "initial dosing regimen" or "starting dose" or a "maintenance dosing regimen" refers to how, when, how much, and for how long a dose of the compositions or dosage forms of the present disclosure can be administered to a subject. For example, an initial or starting dose regimen for a subject may provide for a total daily dose of from about 15 mg to about 1500 mg administered in two divided doses at least 12 hours apart (e.g., once with breakfast and once with dinner) with meals repeated daily for 30 days.

As used herein, "daily dose" refers to the amount of active agent (e.g., pregn-4-ene-3,20-dione) administered to a subject over a 24-hour period of time. The daily dose can be administered one or more administrations during the 24-hour period. In one embodiment, the daily dose provides for two or three or four or six or eight administrations in a 24-hour period. With this in mind, an "initial dose" or initial daily dose" refers to a dose administered during the initial regimen or period of a dosing regimen.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or by other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein "single unit" when used to describe dosing of a subject refers to the dosage form being a single dosage form, e.g. a single tablet, capsule, pump or squirt of gel or solution, etc. In contrast, "multiple unit" when used to describe dosing of a subject refers to the dosage including two or more dosage forms, e.g. 2 capsules, 3 tablets, 2-4 pumps or squirts, etc. It is noteworthy that multiple unit dosage forms generally will be the same type of dosage forms (i.e. tablet or capsule) but are not required to be the same dosage form type.

As used herein, the term "meal" refers to any of the regular occasions in a day when a reasonably large amount of food is eaten, such as breakfast, lunch, or dinner.

As used herein, the term "Tmax" refers to mean or median time to peak serum level post single dose administration.

As used herein, the term "micronized administration" refers to administration of crystalline micronized pregn-4-ene-3,20-dione dispersed in a composition comprising edible oil and lecithin or in a composition comprising monohydrous lactose.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Occurrences of the phrase "in one embodiment," or "in one aspect," herein do not necessarily all refer to the same embodiment or aspect.

As used herein, comparative terms such as "increased," "decreased," "better," "worse," "higher," "lower," "enhanced," "improved," "maximized," "minimized," and the like refer to a property of a device, component, composition, biologic response, biologic status, or activity that is measurably different from other devices, components, compositions, biologic responses, biologic status, or activities that are in a surrounding or adjacent area, that are similarly situated, that are in a single device or composition or in multiple comparable devices or compositions, that are in a group or class, that are in multiple groups or classes, or as compared to an original (e.g. untreated) or baseline state, or the known state of the art. For example, a composition or dosage form comprising pregn-4-ene-3,20-dione that "increases" 3α-OH-5α-pregnan-20-one or 3α-OH-5β-pregnan-20-one serum levels provides a 3α-OH-5α-pregnan-20-one or 3α-OH-5β-pregnan-20-one serum level in a subject that is elevated as compared to a serum level at a previous point in time, such as a baseline level (e.g., prior to treatment), or as compared to an earlier treatment with a different dose (e.g., lower dose). Alternatively, a composition or dosage form that provides an "increased" serum level of 3α-OH-5α-pregnan-20-one or 3α-OH-5β-pregnan-20-one may provide such increase as compared to an alternative known composition or dosage form e.g. compared to an equivalent amount of pregn-4-ene-3,20-dione utilizing a purpose-inadequate carrier or compositions comprising crystalline pregn-4-ene-3,20-dione in oil when orally administered the subject.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "GABA" refers to gamma aminobutyric acid. GABA is the chief inhibitory neurotransmitter in the developmentally mature mammalian CNS. Its principal role is reducing neuronal excitability throughout the nervous system. "GABA receptor" or "GABA receptors" refer to receptors that are modulated by GABA. $GABA_A$ receptors include an ionotropic receptor and ligand-gated ion channel.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Clinical CNS disorder diagnosis and treatment including depression can be assessed by at least one of the following rating scales/questionnaires or similar measures that include measuring severity of depression in individuals:

a. 17-item Hamilton Rating Scale for Depression (HAM-D)

The Hamilton Rating Scale for Depression is a 17-item questionnaire used to diagnose depression, and as a guide to evaluate recovery and remission. The HAM-D is the most commonly used instrument for assessing symptoms of depression and is administered by a trained physician.

b. Montgomery-Asberg Depression Rating Scale for Depression (MADRS)

The Montgomery-Asberg Depression Scale is a clinician-rated scale used to examine the severity of depressive episodes in patients with mood disorders. It consists of a clinical interview of 10 items that moves from broad questions to more detailed ones.

c. Columbia-Suicide Severity Rating Scale (C-SSRS)

The Colombia Suicide Severity Scale is a suicidal ideation and behavior rating scale used to evaluate suicidality. The C-SSRS consists of a baseline assessment that evaluates the lifetime experiences of the subject with suicidal ideation and/or behavior, and a post-baseline evaluation that focuses on suicidal risk since the last visit.

d. The Clinical Global Impression Scale of Severity (CGI-S)

CGI-S is an objective measure of the severity of patient's illness at the time of assessment, relative to the clinician's past experience with patients who have the same diagnosis.

e. The Clinical Global Impression Scale of Improvement (CGI-I)

CGI-I is a 7-item measure to assess the overall improvement of the patient's illness, relative to the subject's baseline condition.

f. Hamilton Rating Scale for Anxiety (HAM-A)

HAM-A is a clinician-rated scale used to assess the severity of anxiety symptoms. The HAM-A consists of 14-items, each defined by a series of anxiety symptoms, both psychic and somatic.

g. Edinburgh Postnatal Depression Scale (EPDS)

EPDS is a self-rated questionnaire used to identify postpartum depression in outpatient, home visiting settings, or at the 6-8 week examination after delivery. The EPDS consists of 10 items that assess depressive symptoms such as feeling of guilt, low energy, anhedonia, sleep disturbance, and suicidal ideation.

i. Maternal Postnatal Attachment Scale (MPAS)

MPAS is a self-rated questionnaire used to assess the mother-to-infant attachment. The MPAS consists of 19 items that evaluate the emotional bond between the mother and the infant.

j. The Center for Epidemiologic Studies Depression Scale (CES-D)

CES-D is a 20-item measure that asks caregivers to rate how often over the past week they experienced symptoms associated with depression, such as restless sleep, poor appetite, and feeling lonely. Response options range from 0 to 3 for each item (0=Rarely or None of the Time, 1=Some or Little of the Time, 2=Moderately or Much of the time, 3=Most or Almost All the Time). Scores range from 0 to 60, with high scores indicating greater depressive symptoms. CES-D also provides cutoff scores (e.g., 16 or greater) that aid in identifying individuals at risk for Clinical Depression, with good sensitivity and specificity and high internal consistency.

k. The Beck Depression Inventory (BDI)

BDI is a 21-item self-reporting questionnaire for evaluating the severity of depression in normal and psychiatric populations. It relies on the theory of negative cognitive distortions as central to depression. Twenty-one items in BDI are consolidated from those observations and ranked 0-3 for severity.

Generally, clinical CNS activity can be assessed thru monitoring some of the CNS vital signs, such as composite memory, verbal memory, visual memory, psychomotor speed, reaction time, complex attention, cognitive flexibility, processing speed, executive function, non-verbal reasoning, social acuity, sustained attention, working memory, simple motor speed. Alternatively, it may be assessed by monitoring occurrence of sleepiness or somnolence (measured by the Multiple Sleep Latency Test: MSLT, or the Maintenance of Wakefulness Test: MWT), dry mouth (measured by Clinical Oral Dryness Score: CODS), loss of consciousness (measured by Electroencephalography: EEG), dizziness (measured by vertigo, presyncope, disequilibrium, light-headedness, and a combination), fatigue (measured by Psychomotor Vigilance Task: PVT), hot flashes (measured by increases in heart rate, finger blood flow, mood rating scale (e.g., sedation, calmness, contentedness), respiratory exchange ratio, skin temperature, and core body temperature, pulse oximetry monitoring (measuring the saturation of oxygen in hemoglobin in arterial blood), and saccadic eye velocity measurements (measuring latency and saccade pair ratios by infrared oculography).

DESCRIPTION

Reference will now be made in detail to preferred invention embodiments. While the embodiments will be described with particularity, the present disclosure is not limited to such embodiments. To the contrary, it is intended to cover alternatives, variants, modifications, and equivalents as may be included within the spirit and scope of the disclosure.

An initial overview of technology embodiments is provided below, and then specific technology embodiments are described in further detail later. This initial summary is intended to aid readers in understanding the technology more quickly but is not intended to identify key features or essential features of the technology nor is it intended to limit the scope of the claimed subject matter.

A pregnenedione is an unsaturated diketone derivative of a pregnane, such as budesonide and pregn-4-ene-3,20-dione. Pregnenediones are prone to high intestinal first pass effect. Some mucosal enzymes (e.g., 5α-reductases also known as 3-oxo-5α-steroid 4-dehydrogenases) are ubiquitously expressed in various tissues including the intestinal tract. Therefore, the small intestine and liver have been implicated in pregnenedione metabolism because of high expression levels of drug-metabolizing enzymes. As illustrated in FIG. 1, two major enzymes groups, 5α reductase and 5β reductase, are involved in the metabolism of orally administered pregn-4-ene-3,20-dione, producing 5α-dihydroprogesterone (DHP) and 5β-DHP. This reduction metabolism is the rate-limiting step in the generation of PAMs and NAMs. The first metabolism pathway results in production of: (a) 3α-OH-5α-pregnan-20-one via 3α-hydroxysteroid dehydrogenase (HSD)-II/III enzyme, and (b) 3β-OH-5α-pregnan-20-one via 3β-hydroxysteroid dehydrogenase (HSD)-II/III enzyme. The second pathway produces: (a) 3α-OH-5β-pregnan-20-one via 3α-HSD and (b) 3β-OH-5β-pregnan-20-one via 3β-HSD enzyme. 3α-OH-5α-pregnan-20-one, a PAM, is a potent positive modulator of $GABA_A$ receptor activity, but its 3 beta epimer, 3β-OH-5α-pregnan-20-one activity on $GABA_A$ receptors is deemed as a NAM and has been shown to modulate the effects of a PAM (e.g., 3α-OH-5α-pregnan-20-one). Also, 3α-OH-5β-pregnan-20-one, a PAM, is known as a potent positive modulator of $GABA_A$ receptor activity, but its 3 beta epimer, 3β-OH-5β-pregnan-20-one is deemed as a NAM and has been shown to modulate the effects of PAM (e.g., 3α-OH-5β-pregnan-20-one).

Some of the neuro-modulatory and protective effects of 3α-OH-5α-pregnan-20-one and/or 3α-OH-5β-pregnan-20-one may contribute to the benefits and side effects of pregn-4-ene-3,20-dione administration. Specifically, 3α-OH-5α-pregnan-20-one and/or 3α-OH-5β-pregnan-20-one can produce anticonvulsant, antidepressant, anxiolytic, and neuroprotective effects in experimental animals as well as in tissues and cell cultures. Human data has been more contradictory, and several studies have been conducted in an effort to evaluate the neuro-modulatory effects of pregn-4-ene-3,20-dione and its metabolites.

Moreover, reported serum levels of neurosteroid, PAM and NAM, metabolites post administration using compositions and methods with purpose-inadequate carrier or crystalline pregn-4-ene-3,20-dione or sub-therapeutic doses result in inadequate levels to effectively treat CNS depression disorders. Furthermore, previous oral pregn-4-ene-3,20-dione disclosures are directed towards reducing side effects in treating a non-CNS indications such as prevention of endometrial hyperplasia in non-hysterectomized postmenopausal women who are receiving conjugated estrogens or for use in secondary amenorrhea such that the pregn-4-ene-3,20-dione composition and methods minimizes the amount of serum 3α-OH-5α-pregnan-20-one and/or 3α-OH-5β-pregnan-20-one; hence, the risk of related adverse effects.

Some efforts have been made in prior compositions to minimize the release of pregn-4-ene-3,20-dione in the upper GI tract to prevent conversion in the intestinal gut, wall, and flora in order to limit side effects from GABA active neurosteroids after oral administration of pregn-4-ene-3,20-dione. However, there have been no compositions or methods of administration directed towards generating adequate levels of GABA$_A$ receptor modulators for therapeutic utility: especially for higher and faster production of the amount of serum 3α-OH-5α-pregnan-20-one and/or 3α-OH-5β-pregnan-20-one. Such prior compositions and methods use components that result in ineffective amount of serum 3α-OH-5α-pregnan-20-one and/or 3α-OH-5β-pregnan-20-one, or that have been formulated with crystalline pregn-4-ene-3,20-dione with deficient characteristics.

Achieving desired serum 3α-OH-5α-pregnan-20-one and/or 3α-OH-5β-pregnan-20-one levels or appropriate oral dose for efficacy for CNS depression indications has remained elusive, especially for unmet disorders such as Major Depressive Disorder or peri-natal or post-partum depression. The production of 3α-OH-5α-pregnan-20-one and/or 3α-OH-5β-pregnan-20-one from oral pregn-4-ene-3,20-dione as a prodrug has been challenging for numerous reasons. For example, oral pregn-4-ene-3,20-dione as a prodrug has resulted in erratic neurosteroid levels and inconsistent PD effects.

Thus, there remains an unmet need for compositions and methods that enable generation of higher, faster, more reliable, and adequate levels of 3α-OH-5α-pregnan-20-one and/or 3α-OH-5β-pregnan-20-one for treating various CNS depression disorders whereby immediate generation and subsequent effective absorption of 3α-OH-5α-pregnan-20-one and/or 3α-OH-5β-pregnan-20-one is enabled for treating women of child-bearing age, and males. In some aspects, we have surprisingly found compositions and methods effective to produce desirable levels of 3α-OH-5α-pregnan-20-one and/or 3α-OH-5β-pregnan-20-one by inducing immediate reduction of the prodrug in favor of high 3α-OH-5α-pregnan-20-one and/or 3α-OH-5β-pregnan-20-one generation in the GI tract needed to treat CNS depression disorders. In one aspect we have surprisingly found compositions and methods effective to produce desirable levels of 3α-OH-5α-pregnan-20-one and/or 3α-OH-5β-pregnan-20-one without significant alteration of the desired CNS activity due to 3β-OH-5α-pregnan-20-one and/or 3β-OH-5β-pregnan-20-one. In yet another aspect, the present compositions and methods comprise amounts of pregn-4-ene-3,20-dione with carriers that is sufficient to provide effective amount(s) of either 301-OH-5α-pregnan-20-one, or 3β-OH-5β-pregnan-20-one, or 3α-OH-5α-pregnan-20-one, or 3α-OH-5β-pregnan-20-one, or a combination thereof for treating the CNS depression disorder in the subject.

In yet another aspect, the present compositions and methods comprise amounts of pregn-4-ene-3,20-dione with carriers that is sufficient to provide effective amount(s) of either 3β-OH-5α-pregnan-20-one, or 3β-OH-5β-pregnan-20-one, or 3α-OH-5α-pregnan-20-one, or 3α-OH-5β-pregnan-20-one, or a combination thereof resulting in desired CNS activity in the subject.

In some aspects, the present compositions and methods treat a CNS disorder comprising depression. For example, a Major Depressive Disorder or perinatal depression or post-partum depression.

In one embodiment, pregn-4-ene-3,20-dione compositions and oral dosage forms can be formulated to provide amounts or peak levels of 3α-OH-5α-pregnan-20-one, or 3α-OH-5β-pregnan-20-one, or both that are therapeutically effective for treating a CNS disorder when orally administered to a subject. For example, in one aspect, the compositions and oral dosage forms can include a pharmaceutically acceptable carrier that provides formation of either 3α-OH-5α-pregnan-20-one, or 3α-OH-5β-pregnan-20-one, or both in an amount sufficient to treat a CNS disorder when orally administered to a subject.

In one embodiment, an oral pharmaceutical composition comprises an amount of pregn-4-ene-3,20-dione and a pharmaceutically acceptable carrier, wherein said composition treats a CNS disorder in a subject upon oral administration by providing at least one of the following serum level ratios comprising:

$C_{max}$/dose of 3α-OH-5β-pregnan-20-one/pregn-4-ene-3,20-dione of from about $5.0 \times 10^{-8}$/ml to about $2.5 \times 10^{-6}$/ml, $C_{max}$/dose of 3α-OH-5α-pregnan-20-one/pregn-4-ene-3,20-dione of from about $7.5 \times 10^{-8}$/ml to about $2.5 \times 10^{-6}$/ml, and $C_{max}$/dose of (3α-OH-5α-pregnan-20-one and 3α-OH-5β-pregnan-20-one)/pregn-4-ene-3,20-dione of from about $1.3 \times 10^{-7}$/ml to about $5.0 \times 10^{-6}$/ml.

In one aspect, the analyte serum levels are measured using a chromatography combined mass spectrometry method (e.g., LC-MS/MS or GC-MS).

In another embodiment, an oral pharmaceutical composition comprises an amount of pregn-4-ene-3,20-dione and a pharmaceutically acceptable carrier, wherein said composition treats a CNS disorder in a subject upon oral administration by providing at least one of the following values comprising:

a serum level $C_{max}$ of 3α-OH-5α-pregnan-20-one of greater than about 18 ng/ml, a serum level $C_{max}$ of 3α-OH-5β-pregnan-20-one of greater than about 11 ng/ml, a ratio of $C_{max}/C_{max}$ of 3α-OH-5α-pregnan-20-one/pregn-4-ene-3,20-dione of from about 3.0 to about 50, a ratio of $C_{max}/C_{max}$ of 3α-OH-5β-pregnan-20-one/pregn-4-ene-3,20-dione of from about 3.0 to about 50, and a ratio of $C_{max}/C_{max}$ of (3α-OH-5α-pregnan-20-one and 3α-OH-5β-pregnan-20-one)/pregn-4-ene-3,20-dione of from about 5 to about 100.

In one aspect, the analyte serum levels are measured using a chromatography combined mass spectrometry method (e.g., LC-MS/MS or GC-MS).

In one aspect, the compositions and oral dosage forms can include a pharmaceutically acceptable carrier comprising said carrier comprises at least one of alpha-tocopherol, glyceryl monocaprylate, propylene glycol monolaurate, PEG-35 castor oil, PEG-40 hydrogenated castor oil, and a combination thereof that provides formation of either 3α-OH-5α-pregnan-20-one, 3α-OH-5β-pregnan-20-one, or both in an amount sufficient to treat a CNS disorder when orally administered to a subject.

In one embodiment, pregn-4-ene-3,20-dione compositions and oral dosage forms can be formulated to provide therapeutically effective amounts of 3α-OH-5α-pregnan-20-one, 3α-OH-5β-pregnan-20-one, or both relative to a pregn-4-ene-3,20-dione composition or method utilizing a purpose-inadequate carrier. In other words, to provide compositions that are therapeutically effective for treating a CNS disorder when orally administered to a subject. In another aspect, the pregn-4-ene-3,20-dione can be in a form that maximizes formation of 3α-OH-5α-pregnan-20-one, 3α-OH-5β-pregnan-20-one, or both when orally administered to a subject. In another aspect, the pregn-4-ene-3,20-dione can be in a form that when orally administered to a subject increases formation of either 3α-OH-5α-pregnan-20-one, 3α-OH-5β-pregnan-20-one, or both. In one aspect, the present compositions and methods, provide increased formation of 3α-OH-5α-pregnan-20-one, 3α-OH-5β-pregnan-20-one, or both when orally administered to a subject, as compared to an equivalent amount of pregn-4-ene-3,20-dione administered from a composition or method that is purpose-inadequate. In another aspect, the present compositions and methods of provide increased formation of 3α-OH-5α-pregnan-20-one, 3α-OH-5β-pregnan-20-one, or both when orally administered to a subject as compared to an equivalent amount of a micronized administration administered to said subject. In some aspects, the micronized pregn-4-ene-3,20-dione can be administered in an oil or oil-based carrier.

In one embodiment, the composition can be formulated as an oral dosage form that has from about 10 mg to about 400 mg of pregn-4-ene-3,20-dione. In one aspect, the oral dosage form can be a liquid, a semi-liquid, a semi solid, a sprinkle, an emulsion, a dispersion, a granule, a syrup, a suspension, a capsule, a tablet, a chew, or a drink.

In yet another embodiment, dosage regimens and methods of treating a CNS depression disorder in a subject are provided and can include orally administering a composition comprising a therapeutically effective amount of pregn-4-ene-3,20-dione to the subject. In one aspect, the therapeutically effective amount of pregn-4-ene-3,20-dione can provide an amount (e.g. average serum levels, $C_{avg}$ or peak serum levels, $C_{max}$) of 3α-OH-5α-pregnan-20-one, or 3α-OH-5β-pregnan-20-one, or both that is sufficient to treat the CNS disorder. In another aspect, the therapeutically effective amount of pregn-4-ene-3,20-dione in a composition can be in a form that provides a therapeutically effective amount of 3α-OH-5α-pregnan-20-one, 3α-OH-5β-pregnan-20-one, or both for treating the CNS disorder in the subject. In yet another aspect, the pregn-4-ene-3,20-dione can be combined with a carrier that is sufficient to provide a therapeutically effective amount of 3α-OH-5α-pregnan-20-one, 3α-OH-5β-pregnan-20-one, or both for treating the CNS disorder in the subject.

In yet another embodiment, dosage regimens and methods of treating a CNS depression disorder in a female comprising a pregnant female or a female who has given birth within at least one of one month, six months, and twelve months.

Compositions

As previously discussed, reported serum levels of neurosteroid metabolites after oral administration of compositions with predominantly crystalline pregn-4-ene-3,20-dione or sub-therapeutic doses do not result in adequate levels to effectively treat CNS depression disorders. In addition, oral pregn-4-ene-3,20-dione as a prodrug has resulted in erratic neurosteroid levels and inconsistent pharmacodynamic effects therefore, an enhanced way of treating CNS depression disorders would be useful.

In one embodiment, an oral pharmaceutical composition can include a therapeutically effective amount of pregn-4-ene-3,20-dione and a pharmaceutically acceptable carrier that provides formation of 3α-OH-5α-pregnan-20-one, 3α-OH-5β-pregnan-20-one, or both in an amount sufficient to treat a CNS depression disorder when orally administered to a subject. In some aspects, the carrier can maximize, speed, or otherwise impact formation of 3α-OH-5α-pregnan-20-one, 3α-OH-5β-pregnan-20-one, or both from the pregn-4-ene-3,20-dione composition when administered to a subject. In some aspects, the carrier can impact release of the pregn-4-ene-3,20-dione when administered to a subject. In some aspects, the carrier can impact generation of the 3α-OH-5α-pregnan-20-one, 3α-OH-5β-pregnan-20-one, or both when administered to a subject. In some aspects, the carrier can impact generation of 3β-OH-5α-pregnan-20-one, 3β-OH-5β-pregnan-20-one, or both when administered to a subject.

In some aspects, the pregn-4-ene-3,20-dione form can impact the generation of 3α-OH-5α-pregnan-20-one, 3α-OH-5β-pregnan-20-one, or both when administered to a subject. In some aspects, the pregn-4-ene-3,20-dione form can impact generation of 30-OH-5α-pregnan-20-one, 3β-OH-5β-pregnan-20-one, or both when administered to a subject.

In some aspects, the pregn-4-ene-3,20-dione daily dose or dosing regimen can impact generation of 3α-OH-5α-pregnan-20-one, 3α-OH-5β-pregnan-20-one, or both when administered to a subject. In some aspects, the pregn-4-ene-3,20-dione daily dose or dosing regimen can impact generation of 3β-OH-5α-pregnan-20-one, 3β-OH-5β-pregnan-20-one, or both when administered to a subject.

In another aspect, the pregn-4-ene-3,20-dione can be in a form that when orally administered to a subject maximizes, speeds, or otherwise impacts increases formation of 3α-OH-5α-pregnan-20-one, 3α-OH-5β-pregnan-20-one, or both. In one embodiment, the pregn-4-ene-3,20-dione can be in a form that increases formation of 3α-OH-5α-pregnan-20-one, 3α-OH-5β-pregnan-20-one, or both as compared to an equivalent amount of a micronized administration. For example, the formation of 3α-OH-5α-pregnan-20-one, 3α-OH-5β-pregnan-20-one, or both can be increased by up to about 8 times or 800% when compared to an equivalent amount of a micronized administration.

The therapeutically effective amount of pregn-4-ene-3,20-dione can vary. In one example, the therapeutically effective amount of pregn-4-ene-3,20-dione can be present in the composition or oral dosage form an amount greater than one or more of: 0.0001 wt %, 0.001 wt %, 0.01 wt %, 0.1 wt %, 0.5 wt %, 1.0 wt %, 2.0 wt %, 5.0 wt %, 10.0 wt %, 15.0 wt %, 20.0 wt %, or combinations thereof. In another example, the therapeutically effective amount of pregn-4-ene-3,20-dione can be present in an amount of from about 0.0001 wt % to about 10 wt % of the composition or oral dosage form. In another example, the therapeutically effective amount of pregn-4-ene-3,20-dione can be present in an amount of from about 10.0001 wt % to about 20 wt %. In yet another example, the therapeutically effective amount of pregn-4-ene-3,20-dione can be present in an amount of from about 20.001 wt % to about 24.999 wt %. In another example, the therapeutically effective amount of pregn-4-ene-3,20-dione can be present in an amount of from 0.06 wt % to about 25 wt % or 3 wt % to 10 wt %.

In one aspect, the present compositions and methods comprise at least one of a substantially non-crystalline and/or a substantially solubilized pregn-4-ene-3,20-dione form.

The therapeutically effective amount of pregn-4-ene-3,20-dione can be combined with a pharmaceutically acceptable carrier to form 3α-OH-5α-pregnan-20-one, 3α-OH-5β-pregnan-20-one, or both in an amount sufficient to treat a CNS depression disorder when administered to a subject. In some embodiments, such a carrier can include an additive. A wide variety of additives can be used to fully or partially solubilize pregn-4-ene-3,20-dione in the pharmaceutical composition in order to provide therapeutically effective levels of 3α-OH-5α-pregnan-20-one and 3α-OH-5β-pregnan-20-one for treating a CNS disorder (e.g., post-partum depression). Examples of suitable additives can include: (i) tocopherol (e.g. vitamin E) or its derivatives; (ii) fatty acids or their salts; (iii) glyceryl fatty acid esters; (iv) PEG glycerides of fatty acid esters; (v) polyglycerol fatty acid esters; (vi) triglycerides; (vii) hydrogenated polyoxyl vegetable oils or glycerides; (viii) propylene glycol fatty acid esters; (ix) edible oils; (x) sterols or its derivatives, (xi) omega oils, such as omega fatty acids, fish oil, flax seed oil, algae oil, and the like, or combinations thereof.

In one aspect, vitamin E or its derivatives can comprise: alpha-tocopherol, beta-tocopherol, gamma-tocopherol, delta-tocopherol, tocopherol acetate, tocopherol linoleate, tocopherol succinate, tocotrienols (alpha-, beta-, gamma-, or delta-), tocofersolan or TPGS (PEG derivatives of alpha-tocopherol), the like, or combinations thereof.

In another aspect, fatty acids or their salts can comprise: octanoic acid, capric acid, lauric acid, myristic acid, palmitic acid, stearic acid, oleic acid, linoleic acid, linoelaidic acid, sodium caproate, sodium caprylate, sodium laurate, sodium myristate, sodium palmitate, sodium oleate, sodium stearate, SLS, sodium lauryl sarcosinate, sodium dioctyl sulfosuccinate, sodium cholate, sodium taurocholate, the like, or combinations thereof.

In another aspect, glyceryl fatty acid esters can comprise: glyceryl monooleate, glyceryl monoleate/linoleate, glyceryl monolinoleate, glyceryl ricinoloeate, glyceryl monolaurate, glyceryl monopalmitate, glyceryl monostearate, glyceryl mono-/di-oleate, glyceryl palmitate/stearate, glyceryl acetate, glyceryl laurate, glyceryl citrate/lactate/oleate/linoleate, glyceryl caprylate, glyceryl caprylate/caprate, glyceryl dicaprylate/dicaprate, mono-/di-acetylated monoglycerides, glyceryl monostearate, glyceryl dilaurate, glyceryl dioleate, the like, or combinations thereof.

In yet another aspect, PEG glycerides of fatty acid esters can comprise: PEG fatty acid monoesters, PEG glycerol fatty acid esters, PEG fatty acid diesters, PEG fatty acid mono-/di-ester mixtures, PEG triglycerides of fatty acid esters, the like, or combinations thereof. PEG glycerol fatty acid esters can comprise: PEG glyceryl laurate, PEG glyceryl laurate, PEG glyceryl caprylate, PEG glyceryl caprate, PEG glyceryl oleate, PEG glyceryl mono-/di-fatty acid ester mixtures, the like, or combinations thereof. PEG fatty acid monoesters can comprise: esters of caprylic acid, capric acid, lauric acid, oleic acid, and stearic acid, the like, or combinations thereof. Examples of the PEG fatty acid monoesters can include PEG (1-100, 200, 300, 400) monocaprylate, PEG (1-100, 200, 300, 400) monocaprate, PEG (1-100, 200, 300, 400) monolaurate, PEG (1-100, 200, 300, 400) monooleate, PEG (1-100, 200, 300, 400) monopalmitate, PEG (1-100, 200, 300, 400) monostearate, and PEG (1-100, 200, 300, 400) monococoate, the like, or combinations thereof. PEG fatty acid diesters can comprise PEG (4-32) dicaprylate, PEG (4-32) dicaprate, PEG (4-32) dilaurate, PEG (4-32) dioleate, PEG (4-32) distearate, and PEG (4-32) dipalmitate, the like, or combinations thereof. PEG fatty acid mono-/di-ester mixtures can comprise: PEG caprylate/caprate, PEG mono-/di-caprylate, PEG mono-/di-caprate, PEG mono-/di-laurate, PEG mono-/di-oleate, and PEG mono-/di-stearate the like, or combinations thereof. PEG triglycerides of fatty acid esters can comprise: lauroyl polyoxylglycerides, stearoyl polyoxylglycerides, oleoyl polyoxyl glycerides, linoleoyl polyoxyl glycerides, lauroyl polyoxyl glycerides, caprylocaproyl polyoxyl glycerides, and behenoyl polyoxylglycerides the like, or combinations thereof.

In a further aspect, polyglycerol fatty acid esters can comprise: polyglyceryl (2, 3, 4, 6, 10) oleate, polyglyceryl (2, 3, 4, 6, 10) dioleate, polyglyceryl (2, 3, 4, 6, 10) trioleate, polyglyceryl (2, 3, 4, 6, 10) laurate, polyglyceryl (2, 3, 4, 6, 10) dilaurate, polyglyceryl (2, 3, 4, 6, 10) trilaurate, polyglyceryl (2, 3, 4, 6, 10) stearate, polyglyceryl (2, 3, 4, 6, 10) distearate, polyglyceryl (2, 3, 4, 6, 10) tristearate, polyglyceryl (2, 3, 4, 6, 10) mono-/di-oleate, polyglyceryl (3,6,10) caprate, polyglyceryl (3,6,10) dicaprate, polyglyceryl (3,6,10) tricaprate, polyglyceryl (3,6,10) caprylate, polyglyceryl (3,6,10) dicaprylate, polyglyceryl (3,6,10) tricaprylate, polyglyceryl (3,6,10) polystearate, polyglyceryl (3,6,10) polyoleate, polyglyceryl (3,6,10) mono-/di-oleate, polyglyceryl (3,6,10) caprylate, polyglyceryl (3,6,10) polycaprylate, polyglyceryl (3,6,10) caprate, polyglyceryl (3,6,10) polycaprate, and polyglyceryl (3,6,10) caprylate/caprate, the like, or combinations thereof.

In another aspect, triglycerides can comprise: glyceryl tricaprylate, glyceryl tricaprate, glyceryl tricaprylate/tricaprate, glyceryl tricaprylate/tricaprate/trisuccinate, glyceryl trioleate, glyceryl tristearate, glyceryl trilaurate, medium chain natural oils, the like, or combinations thereof.

In yet another aspect, hydrogenated polyoxyl vegetable oils or glycerides can comprise: castor oil or hydrogenated castor oil, or an edible vegetable oil such as corn oil, olive oil, peanut oil, palm kernel oil, apricot kernel oil, peppermint oil, coconut oil, sunflower seed oil, or almond oil, the like, or combinations thereof. The polyoxyl group can include glycerol, propylene glycol, ethylene glycol, polyethylene glycol, sorbitol, pentaerythritol, the like, or combinations thereof. Examples of hydrogenated polyoxyl vegetable oils or glycerides can comprise: PEG-35 castor oil (Incrocas-35, Kolliphor EL, Cremophor EL), PEG-40 hydrogenated castor oil (Kolliphor RH 40, Cremophor RH40), PEG-25 trioleate (TAGATRTO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), PEG-6 caprylic/capric glycerides (Softigen 767), PEG-5 hydrogenated castor oil, PEG-7 hydrogenated castor oil, PEG-9 hydrogenated castor oil, PEG-6 corn oil (Labrafil M. 2125 CS), PEG-6 almond oil (Labrafil M 1966 CS), PEG-6 apricot kernel oil (Labrafil M 1944CS), PEG-6 olive oil (Labrafil M 1980 CS), PEG-6 peanut oil (Labrafil M 1969 CS), PEG-6 hydrogenated palm kernel oil (Labrafil M2130 BS), PEG-6 palm kernel oil (Labrafil M 2130 CS), PEG-6 triolein (Labrafil M 2735 CS), PEG-8 corn oil (Labrafil WL 2609 BS), PEG-20 corn glycerides (Crovol M40), and PEG-20 almond glycerides (Crovol A40), the like, or combinations thereof.

In one aspect, propylene glycol fatty acid esters can comprise: propylene glycol monolaurate (Lauroglycol FCC), propylene glycol ricinoleate (Propymuls), propylene glycol monooleate (Myverol P-O6), propylene glycol dicaprylate/dicaprate (Captex 200), and propylene glycol dioctanoate (Captex 800), propylene glycol monocaprylate (Capryol 90, Nikkol Sefsol 218), propylene glycol myristate, propylene glycol monostearate, propylene glycol ricinolate, propylene glycol isostearate, propylene glycol caprylate/caprate, propylene glycol dioleate, propylene glycol distearate, propylene glycol dilaurate, propylene glycol dicaprylate, and propylene glycol dicaprate, the like, or combinations thereof.

In another aspect, edible oils can comprise: corn oil, olive oil, peanut oil, coconut oil, peppermint oil, sunflower seed oil, castor oil, safflower oil, borage oil, cottonseed oil, soybean oil, palm kernel oil, apricot kernel oil, almond oil, omega-3 oil or its derivatives, the like, or combinations thereof.

In one aspect, sterols or its derivatives can comprise: cholesterol, sitosterol, lanosterol, phytosterol, its PEG derivatives, the like, or combinations thereof.

In one embodiment, an additive can be a substance that can be added to the pharmaceutical formulation to enhance the solubilization, separation, or dispersion of the particles, or to enhance the dissolution and further absorption of the particles into the body. Examples of additives can include a lipophilic additive when it has an HLB value of 10 or less, or a hydrophilic additive when it has an HLB value of greater than 10.

In one aspect, the pharmaceutically acceptable carrier can comprise a hydrophilic additive, a lipophilic additive, or a combination thereof.

In one aspect, lipophilic additives can comprise: mono-, di-glycerides of fatty acids, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. Labrafil M 2125 CS), PEG-6 almond oil (e.g. Labrafil M 1966 CS), PEG-6 apricot kernel oil (e.g. Labrafil M 1944 CS), PEG-6 olive oil (e.g. Labrafil M 1980 CS), PEG-6 peanut oil (e.g. Labrafil M 1969 CS), PEG-6 hydrogenated palm kernel oil (e.g. Labrafil M 2130 BS), PEG-6 palm kernel oil (e.g. Labrafil M 2130 CS), PEG-6 triolein (e.g. Labrafil M 2735 CS), PEG-8 corn oil (e.g. Labrafil WL 2609 BS), PEG-20 corn glycerides (e.g. Crovol M40), PEG-20 almond glycerides (e.g. Crovol A40), lipophilic polyoxyethylene-polyoxypropylene block co-polymers (e.g. Pluronic L92, L101, L121 etc.), propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. CAPTEX® 200), and propylene glycol dioctanoate (e.g. CAPTEX® 800), propylene glycol mono-caprylate (e.g. CAPRYOL® 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. ARLACEL® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof, sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, Linoleoyl Polyoxyl-6 glycerides, polyglyceryl 3-oleate, lauroyl PEG-32 glycerides, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. In some cases, an additive for the compositions and oral dosage forms can be a lipophilic surfactant.

The pharmaceutically acceptable carrier can also comprise a hydrophilic additive. In one aspect, the hydrophilic additive can comprise without limitation, non-ionic surfactants, ionic surfactants, zwitterionic surfactants, the like, or combinations thereof. Suitable hydrophilic surfactants can include: alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol, the like, or combinations thereof. Two or more hydrophilic additives from the same or different classes can be referred to as the hydrophilic surfactant unless explicitly specified. In one aspect, non-limiting examples of hydrophilic surfactants can comprise PEG-8 caprylic/capric glycerides, lauroyl macrogol-32 glyceride, stearoyl macrogol glyceride, PEG-40 hydrogenated castor oil, PEG-35 castor oil, SLS, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, the like, or combinations thereof. In some cases, a hydrophilic additive for the compositions and oral dosage forms can be a hydrophilic surfactant.

In yet another aspect, additives can comprise sterols and derivatives of sterols. In various aspects, these additional agents can be hydrophilic or lipophilic. Examples of hydrophilic sterols include: lanosterol PEG-24 cholesterol ether (e.g. Solulan C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko). Examples of Lipophilic Sterol Surfactants are Cholesterol, sitosterol, Phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko), the like, or combinations thereof.

In another aspect, the oral compositions can further comprise a polymeric release modifier. The polymeric release modifier can comprise: celluloses, such as hydroxypropyl celluloses low molecular weight, low viscosity types (e.g. Methocel E5, E6, E10 E15, LV100 etc. grades), hydroxypropyl celluloses having higher molecular weight, medium to high viscosity (e.g. Methocel K4M, K15M, K100M etc.), polyvinylpyrrolidones (e.g. Kollidon k17, K30 etc.), polyvinyl acetates, hydroxypropyl methylcellulose (HPMC), hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP) and crosslinked PVP polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, Sodium croscarmellose, carrageenan, hydroxyethyl cellulose (HEC), carboxymethyl cellulose (CMC) and carboxy ethyl cellulose (CEC), sodium alginate, polycarbophil, gelatin, Xanthan gum, and sodium starch glycolate, the like, or combinations thereof.

The pharmaceutically acceptable carrier can be combined with or otherwise include additives in various amount ranges. For example, the lipophilic additive and hydrophilic additive can be present in amounts such that the ratio of amount (wt %) of lipophilic additive to amount (wt %) of hydrophilic additive is greater than 2:1. In another aspect, the lipophilic additive and hydrophilic additive can be present in amounts such that the ratio of amount (wt %) of lipophilic additive to amount (wt %) of hydrophilic additive is greater than 2.5:1. In another aspect, the lipophilic additive and hydrophilic additive can be present in amounts such that the ratio of amount (wt %) of lipophilic additive to amount (wt %) of hydrophilic additive is greater than 3.5:1. In still another aspect, the lipophilic additive and hydrophilic additive can be present in amounts such that the ratio of amount (wt %) of lipophilic additive to amount (wt %) of hydrophilic additive is at least 6.5:1.

In certain examples, the hydrophilic additive can make up about 1% w/w to about 80% w/w, about 5% w/w to about 70% w/w, about 10% w/w to about 60% w/w, about 15% w/w to about 55% w/w, about 20% w/w to about 50% w/w, about 30% w/w, about 35% w/w, about 40% w/w, about 45% w/w, about 50% w/w, about 55% w/w, about 60% w/w, about 65% w/w, about 70% w/w, about 75% w/w, or about 80% w/w of any pharmaceutical composition described herein. In some examples, the lipophilic additive can make up about 1% w/w to about 90% w/w, about 5% w/w to about 80% w/w, about 5% w/w to about 70% w/w, about 10% w/w to about 60% w/w, about 1% w/w to about 50% w/w, about 5% w/w to about 45% w/w, about 10% w/w to about 40% w/w, about 15% w/w to about 35% w/w, about 20% w/w to about 30% w/w, about 5% w/w, about 6% w/w, about 7% w/w, about 8% w/w, about 10% w/w, about 15% w/w, about 20% w/w, about 25% w/w, or greater than about 30% w/w of any pharmaceutical composition described herein.

Co-solvents can partially solubilize Pregn-4-ene-3,20-dione when presented in an effective amount. Examples of suitable co-solvents can comprise without limitation: alcohols and polyols, such as ethanol, propanol, isopropanol, butanol, benzyl alcohol, ethylene glycol, propylene glycol, butanediols, glycerin or its derivatives thereof, glycerol, diglycerol, polyglycerol, pentaerythritol, sorbitol, mannitol, transcutol, dimethyl isosorbide, triacetin, trimethyl citrate, polyethylene glycol, polypropylene glycol, polyvinylalcohol, hydroxypropyl methylcellulose and other cellulose derivatives, cyclodextrins or its derivatives, the like, or combinations thereof.

In one embodiment, the present oral compositions or dosage forms can provide a ratio of pregn-4-ene-3,20-dione to alpha-tocopherol from about 0.3 to 2.0, such as about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, and about 2.0.

In another embodiment, the present oral compositions or dosage forms can provide a ratio of pregn-4-ene-3,20-dione to glyceryl monocaprylate less than about 0.2, such as about 0.2, about 0.19, about 0.18, about 0.17, about 0.16, about 0.15, about 0.14, about 0.13, about 0.12, about 0.11, about 0.10, about 0.09, and less than about 0.09.

In a further embodiment, the present oral compositions or dosage forms can provide a ratio of alpha-tocopherol to a hydrophilic ingredient from about 0.05 to 4.0, such as about 0.05, about 0.1, about 0.3, about 0.5, about 0.7, about 0.9, about 1.1, about 1.3, about 1.4, about 1.7, about 2.0, about 2.3, about 2.6, about 2.9, about 3.2, about 3.5, and about 4.0.

In yet another embodiment, the present oral compositions or dosage forms can provide a ratio of glyceryl monocaprylate to a hydrophilic ingredient from about 1 to 20 and about 1 to 10, such as about 1, about 2, about 3, about 4, about 5, about 6, about 7, about 8, about 9, and about 10. In another example, the ratio of glyceryl monocaprylate to a hydrophilic ingredient can be from less than about 2, about 1.9, about 1.8, about 1.7, about 1.6, about 1.5, about 1.4, about 1.3, about 1.2, about 1.1, and about 1.0.

In one aspect, the composition can be formulated as a solution, an emulsion, a liquid, a semi-liquid, a suspension, a semi solid, a sprinkle, an emulsion, a dispersion, a granule, a syrup, a suspension, a capsule, a tablet, a chew, or a drink, or the like, or combinations thereof. In one example, the composition can form a dispersion, an emulsion, a solution, or a micellar solution upon 10× or 100× dilution with an aqueous bile salt comprising simulated gastric or intestinal media or water (e.g. FeSSIF, or FaSSIF media well known in the art). In another example, the composition can remain substantially solubilized upon 10× or 100× dilution with an aqueous bile salt comprising simulated gastric or intestinal media or water. In another example, the composition can form a dispersion upon 10× or 100× dilution with an aqueous bile salt comprising simulated gastric or intestinal media or water with a mean dispersion particle size of less than 300 nm or a UV absorbance of less than 3 units when measured at 400 nm.

In one embodiment, the pregn-4-ene-3,20-dione can include a crystalline form that is milled, nanosized, micronized, ultra-micronized, the like, or combinations thereof. In one aspect, the present composition consists of only pregn-4-ene-3,20-dione active in the carrier. In another aspect, the present composition consists of and is free of estradiol. In one another aspect, a specified weight percentage of the pregn-4-ene-3,20-dione in the carrier can be in a non-crystalline form (e.g., amorphous solid, a solution an emulsion, a liquid, a semi-liquid, a suspension, or the like). In one example, at least about 50% of the pregn-4-ene-3,20-dione in the carrier can be in a non-crystalline state. In another example, at least about 65% of the pregn-4-ene-3,20-dione in the carrier can be in a non-crystalline state. In yet another example, at least about 80% of the pregn-4-ene-3,20-dione in the carrier can be in anon-crystalline state. In another example, at least about 95% of the pregn-4-ene-3,20-dione in the carrier can be in a non-crystalline state. In one aspect, the present oral compositions can be comprised substantially free of micronized suspension form of crystalline pregn-4-ene-3,20-dione.

In one embodiment, oral compositions herein can be free of or substantially free of solid forms of pregn-4-ene-3,20-dione. In another embodiment, the present oral compositions can be free of or substantially free of release modulators.

In another aspect, a specified weight percentage of the pregn-4-ene-3,20-dione in the carrier can be solubilized. In one example, from about 50% to about 100% of the pregn-4-ene-3,20-dione in the carrier can be solubilized. In another example, from about 50% to about 65% of the pregn-4-ene-3,20-dione in the carrier can be solubilized. In yet another example, from about 65% to about 85% of the pregn-4-ene-3,20-dione in the carrier can be solubilized. In another example, from about 85% to about 100% of the pregn-4-ene-3,20-dione in the carrier can be solubilized.

Figure 2:
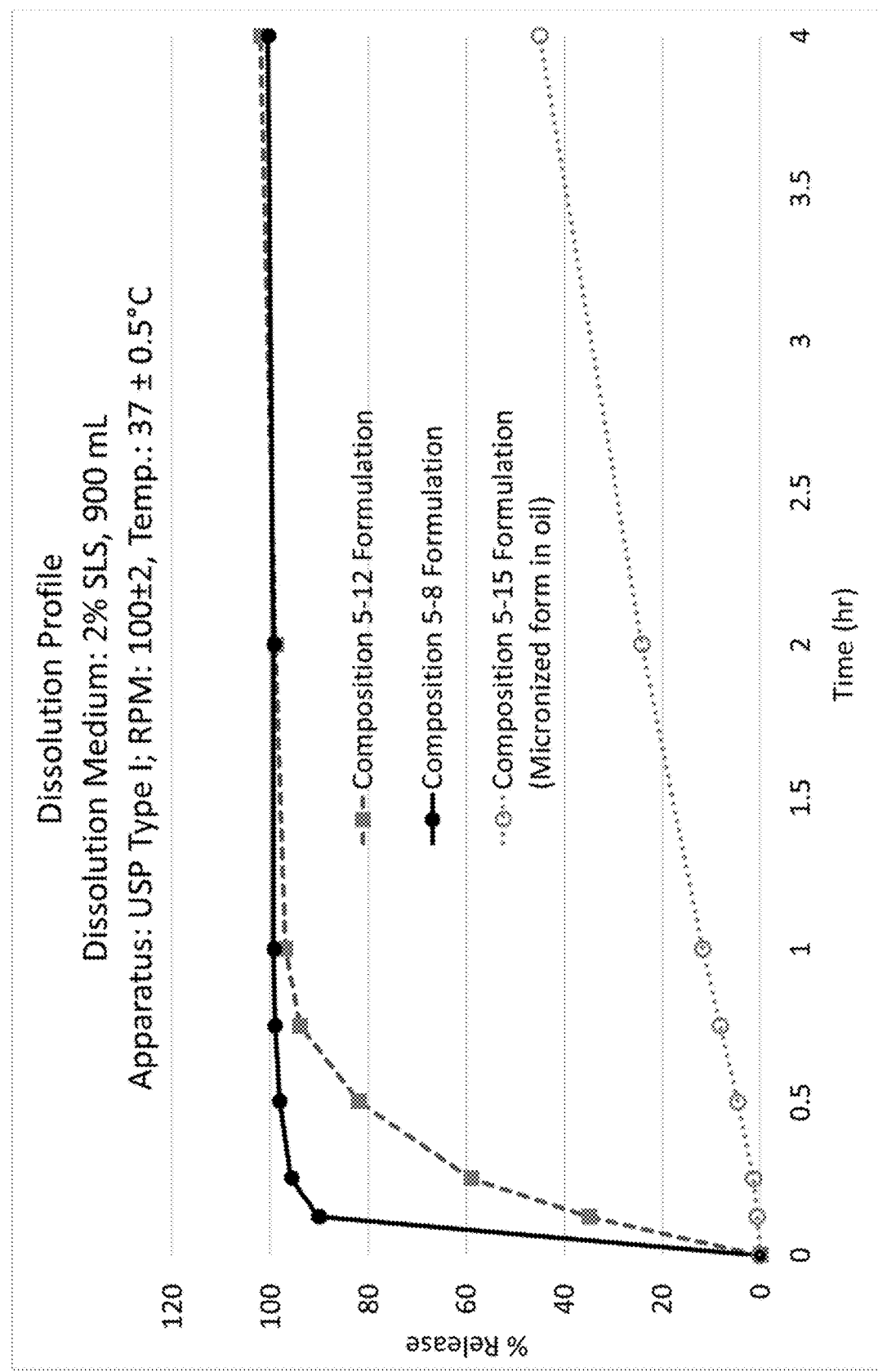
FIG. 2 depicts plots of the release profile of pregn-4-ene-3,20-dione containing oral dosage forms in accordance with certain invention embodiments as compared to a dosage form containing 100 mg micronized pregn-4-ene-3,20-dione suspended in oil. The % release of pregn-4-ene-3,20-dione was measured using a USP Type I dissolution apparatus in 900 mL of deionized water with 2.0% (w/v) of sodium lauryl sulfate (SLS) at 100 rpm at 37° C.

FIG. 2 shows a plot of the release of several examples of the present oral compositions comprising pregn-4-ene-3,20-dione and a composition comprising a micronized pregn-4-ene-3,20-dione suspension in oil performed using a USP Type I dissolution apparatus in 900 mL of deionized water with 2.0% (w/v) of SLS at 100 rpm at 37° C.

In one example, as shown in FIG. 2, the present compositions can release greater than about 50% of the pregn-4-ene-3,20-dione after 15 minutes when measured using a USP Type I dissolution apparatus in 900 mL of deionized water with 2.0% (w/v) of SLS at 100 rpm at 37° C.

In another example, as shown in FIG. 2, the present compositions can release greater than about 75% of the pregn-4-ene-3,20-dione after 30 minutes when measured using a USP Type I dissolution apparatus in 900 mL of deionized water with 2.0% (w/v) of SLS at 100 rpm at 37° C.

In another example, as shown in FIG. 2, the present compositions can release greater than about 90% of the pregn-4-ene-3,20-dione after 60 minutes when measured using a USP Type I dissolution apparatus in 900 mL of deionized water with 2.0% (w/v) of SLS at 100 rpm at 37° C.

In another example, as shown in FIG. 2, the present compositions can release greater than 50% of the pregn-4-ene-3,20-dione in 4 hours from the when measured using a USP Type I dissolution apparatus in 900 mL of deionized water with 2.0% (w/v) of SLS at 100 rpm at 37° C.

In another example, as shown in FIG. 2, the present can release greater than about 30% more of pregn-4-ene-3,20-dione after 15 minutes as compared to the % release from a micronized administration.

Figure 3:
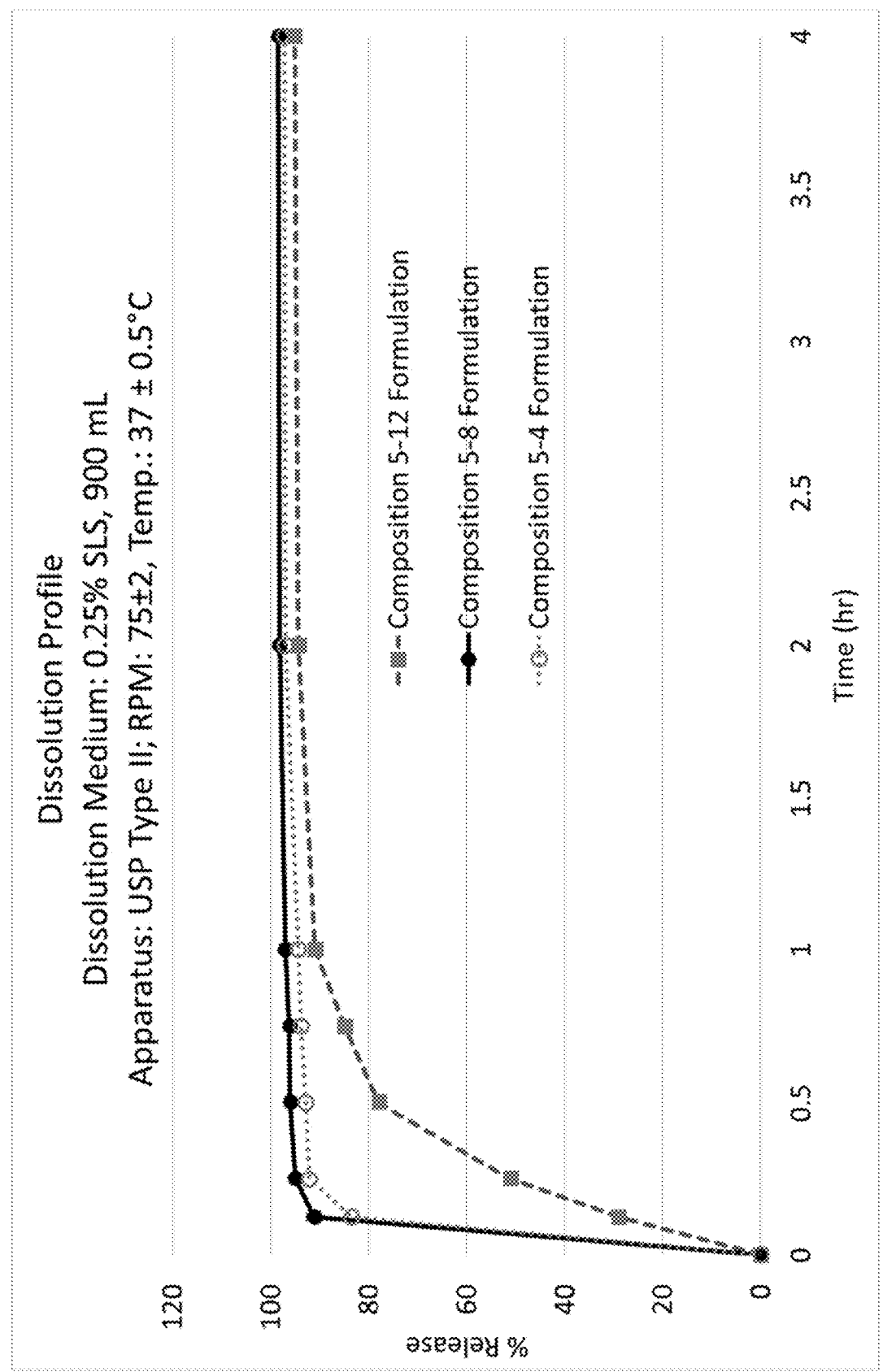
FIG. 3 depicts plots of the release profile of pregn-4-ene-3,20-dione containing oral dosage forms in accordance with certain invention embodiments. The % release of pregn-4-ene-3,20-dione was measured using a USP Type II dissolution apparatus in 900 mL of deionized water with 0.25% (w/v) of SLS at 75 rpm at 37° C.

FIG. 3 shows a plot of the release of several examples for oral compositions comprising pregn-4-ene-3,20-dione performed using a USP Type II dissolution apparatus in 900 mL of deionized water with 0.25% (w/v) of SLS at 75 rpm at 37° C.

In one example, as shown in FIG. 3, the present compositions can release greater than about 50% of the pregn-4-ene-3,20-dione after 20 minutes when measured using a USP Type II dissolution apparatus in 900 mL of deionized water with 0.25% (w/v) of SLS at 75 rpm at 37° C.

In another example, as shown in FIG. 3, the present compositions can release greater than about 75% of the pregn-4-ene-3,20-dione after 30 minutes when measured using a USP Type II dissolution apparatus in 900 mL of deionized water with 0.25% (w/v) of SLS at 75 rpm at 37° C.

In another example, as shown in FIG. 3, the present compositions can release greater than about 90% of the pregn-4-ene-3,20-dione after 60 minutes when measured using a USP Type II dissolution apparatus in 900 mL of deionized water with 0.25% (w/v) of SLS at 75 rpm at 37° C.

In another example, as shown in FIG. 3, the present compositions can release greater than 50% of the pregn-4-ene-3,20-dione in 4 hours from the when measured using a USP Type II dissolution apparatus in 900 mL of deionized water with 0.25% (w/v) of SLS at 75 rpm at 37° C.

In yet another example, the present compositions can release greater than about 30% more of the pregn-4-ene-3,20-dione after 20 minutes as compared to a substantially equivalent amount of a micronized administration when measured using a USP Type III reciprocating cylinder dissolution apparatus at 30 dips per minute in 250 mL of a solution of 0.1N HCl with 3% SLS at 37° C.

In another embodiment, an oral pharmaceutical composition or oral dosage form can include an amount of pregn-4-ene-3,20-dione, that provides $GABA_A$ receptor binding pregn-4-ene-3,20-dione metabolites in amounts that therapeutically effect CNS disorders when administered to a subject. For example, in one embodiment, the composition or oral dosage form can include a pharmaceutically acceptable carrier that maximizes or otherwise accelerates formation of $GABA_A$ receptor PAMs when administered to a subject. In yet another embodiment, the composition or oral dosage form can include pregn-4-ene-3,20-dione in a form that maximizes or otherwise speeds or accelerates formation of $GABA_A$ receptor PAMs when administered to a subject. In yet another embodiment, the composition or oral dosage formulation can include a therapeutically effective amount of pregn-4-ene-3,20-dione that increases $GABA_A$ receptor PAMs formation as compared to an equivalent amount of a micronized administration. In one aspect, the increased metabolite formation for the composition can be up to about 8 times when compared to an equivalent amount of a micronized administration. In one aspect, $GABA_A$ receptor PAMs can be selected from the group comprising: 3α-OH-5α-pregnan-20-one and 3α-OH-5β-pregnan-20-one.

In one embodiment, the composition or oral dosage form can include a pharmaceutically acceptable carrier that minimizes formation of $GABA_A$ receptor NAMs when administered to a subject. In yet another embodiment, the composition or oral dosage form can include pregn-4-ene-3,20-dione in a form that minimizes or otherwise decrease formation of $GABA_A$ receptor NAMs when administered to a subject. In yet another embodiment, the composition or oral dosage formulation can include a therapeutically effective amount of pregn-4-ene-3,20-dione that increases $GABA_A$ receptor NAMs formation as compared to an equivalent amount a micronized administration administered the subject. In one aspect, $GABA_A$ receptor NAMs can be selected from the group comprising: 3β-OH-5α-pregnan-20-one and 3β-OH-5β-pregnan-20-one.

Dosage Forms and Dosing Regimens

In one embodiment, the composition can be formulated as an oral dosage form. The oral dosage form can be a member selected from the group consisting of: a liquid, a semi-liquid, a semi solid, a sprinkle, an emulsion, a dispersion, a granule, a syrup, a suspension, a capsule, a tablet, a chew, or a drink the like, or combinations thereof. In one aspect, the composition can be formulated as an oral dosage form that has from about 10 mg to about 200 mg of pregn-4-ene-3,20-dione. In another aspect, the composition can be formulated as an oral dosage form that has from about 10 mg to about 400 mg of pregn-4-ene-3,20-dione that when orally administered to a subject provides a 3α-OH-5α-pregnan-20-one $C_{max}$ of greater than about 18 ng/ml, or a 3α-OH-5β-pregnan-20-one $C_{max}$ greater than about 11 ng/ml, a 3β-OH-5α-pregnan-20-one $C_{max}$ of greater than about 2.5 ng/ml, or a 3β-OH-5β-pregnan-20-one $C_{max}$ greater than about 2.0 ng/ml, or a combination thereof.

In a further embodiment, the present drink compositions or dosage forms may be formulated as an oral dosage form comprising from about 10 mg to about 900 mg of pregn-4-ene-3,20-dione in a unit dose drinks of about 15 mL up to 90 mL. In one aspect, the present drink compositions or dosage forms can comprise from about 20 mg to about 750 mg of pregn-4-ene-3,20-dione in a single unit dose drink. In one aspect, the present drink compositions or dosage forms can comprise from about 30 mg to about 600 mg of pregn-4-ene-3,20-dione in a single unit dose drink. In a further aspect, the present drink compositions or dosage forms can comprise at least one of about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, or any amount between the above values of pregn-4-ene-3,20-dione in a single unit dose drink.

In a further embodiment, the present drink compositions or dosage forms can comprise from pregn-4-ene-3,20-dione of about 0.06 w/w % to about 1.0 w/w % in a single unit dose drink of about 15 mL to about 90 mL. In an aspect, pregn-4-ene-3,20-dione comprised in the present drink compositions or dosage forms can be one of about 0.06 w/w %, about 0.07 w/w %, about 0.08 w/w %, about 0.09 w/w %, about 0.1 w/w %, about 0.2 w/w %, about 0.3 w/w %, about 0.4 w/w %, about 0.5 w/w %, about 0.6 w/w %, about 0.7 w/w %, about 0.8 w/w %, about 0.9 w/w %, or about 1.0 w/w % in a single unit dose drink of about 15 mL up to 90 mL.

In yet another embodiment, the present drink compositions or dosage forms can optionally comprise other carrier ingredients comprising at least one of flavoring agents, sweeteners, antimicrobial preservatives, antioxidants, and edible fat. In one aspect, flavoring agents can be selected from natural and/or artificial flavors of strawberry, fruit punch, cherry, bubble gum or a combination thereof. In another aspect, sweeteners can be selected from sucralose, sucrose, maltose, acesulfame potassium, or a combination thereof. In other aspect, antimicrobial preservatives can be selected from sodium benzoate, benzoic acid, methyl paraben, propyl paraben, or a combination thereof. In yet further aspect, antioxidants can be selected from disodium edetate, sodium citrate, citric acid, ascorbic acid, ascorbyl palmitate, alpha-tocopherol, BHA, BHT, or a combination thereof.

In yet another embodiment, the present drink compositions or dosage forms comprising pregn-4-ene-3,20-dione can include about 10 to about 15 g of total fat or can be administered with a snack or meal of at least 10 g of total fat.

In one embodiment, the present oral compositions can comprise at least one of less than 195 mg of pregn-4-ene-3,20-dione, less than 95 mg of pregn-4-ene-3,20-dione, less than 70 mg of pregn-4-ene-3,20-dione, less than 58 mg of pregn-4-ene-3,20-dione, less than 48 mg of pregn-4-ene-3,20-dione, less than 30.0% w/w of pregn-4-ene-3,20-dione, less than 17.3% w/w of pregn-4-ene-3,20-dione, less than 13.3% w/w of pregn-4-ene-3,20-dione, less than 9.8% w/w of pregn-4-ene-3,20-dione, less than 8.8% w/w of pregn-4-ene-3,20-dione, less than 8.4% w/w of pregn-4-ene-3,20-dione, less than 7.8% w/w of pregn-4-ene-3,20-dione, less than 7.0% w/w of pregn-4-ene-3,20-dione, less than 6.8% w/w of pregn-4-ene-3,20-dione, less than 5.8% w/w of pregn-4-ene-3,20-dione, or less than 3.9% w/w of pregn-4-ene-3,20-dione.

In one embodiment, the present oral compositions can comprise at least one of from 62 mg to 98 mg of pregn-4-ene-3,20-dione, from 78 mg to 145 mg of pregn-4-ene-3,20-dione, from 155 mg to 195 mg of pregn-4-ene-3,20-dione, from 2.8% w/w to 9.8% w/w of pregn-4-ene-3,20-dione, from 7.2% w/w to 8.3% w/w of pregn-4-ene-3,20-dione, from 8.2% w/w to 9.8% w/w of pregn-4-ene-3,20-dione, from 8.8% w/w to 13.0% w/w of pregn-4-ene-3,20-dione, from 10.2% w/w to 14.8% w/w of pregn-4-ene-3,20-dione, or from 8.7% w/w to 22.3% w/w of pregn-4-ene-3,20-dione.

In one embodiment, the present oral compositions can comprise at least one of greater than 52 mg of pregn-4-ene-3,20-dione, greater than 62 mg of pregn-4-ene-3,20-dione, greater than 75 mg of pregn-4-ene-3,20-dione, greater than 102 mg of pregn-4-ene-3,20-dione, greater than 205 mg of pregn-4-ene-3,20-dione, greater than 4.3% w/w of pregn-4-ene-3,20-dione, greater than 4.7% w/w of pregn-4-ene-3,20-dione, greater than 6.2% of pregn-4-ene-3,20-dione, greater than 7.2% w/w of pregn-4-ene-3,20-dione, greater than 7.5% of pregn-4-ene-3,20-dione, greater than 9.2% w/w of pregn-4-ene-3,20-dione, greater than 10.2% w/w of pregn-4-ene-3,20-dione, greater than 13.4% w/w of pregn-4-ene-3,20-dione, greater than 15.2% w/w of pregn-4-ene-3,20-dione, greater than 17.7% w/w of pregn-4-ene-3,20-dione, or greater than 22.7% w/w of pregn-4-ene-3,20-dione.

In one embodiment, the present oral compositions can comprise at least one of free of alcohol, less than 2.8% w/w of alcohol, less than 5.8% w/w of alcohol, less than 9.8% w/w of alcohol, less than 15.2% w/w of alcohol, from 3.2% w/w to 6.8% w/w of alcohol, greater than 6.2% w/w of alcohol, greater than 7.2% w/w of alcohol, greater than 10.2% w/w of alcohol, greater than 15.6% w/w of alcohol, and. free of ethanol.

In one embodiment, the present oral compositions can comprise at least one of free of hydrophilic solidifying agents, free of PEG 8000, less than 5.9% w/w of PEG 8000, less than 6.0% w/w of PEG 8000, less than 7.7% w/w of PEG 8000, greater than 6.1% w/w of PEG 8000, greater than 6.4% w/w of PEG 8000, and greater than 8.0% w/w of PEG 8000.

In one embodiment, the present oral compositions can comprise at least one of free of propylene glycol, less than 108 mg of propylene glycol, and greater than 183 mg of propylene glycol.

In one embodiment, the present oral compositions can comprise at least one of free of triethyl citrate, less than 5.8% w/w of triethyl citrate, and greater than 6.2% w/w of triethyl citrate.

In one embodiment, the present oral compositions can comprise at least one of free of triacetin, less than 5.8% w/w of triacetin, and greater than 6.2% w/w of triacetin.

In one embodiment, the present oral compositions can comprise at least one of free of lecithin or its derivatives, less than 1.5% w/w of lecithin, greater than 0.4% w/w of lecithin, and greater than 1.7% w/w of lecithin.

In one embodiment, the present oral compositions can comprise at least one of free of lauroyl polyoxyl-32 glycerides, less than about 1.2% w/w of lauroyl polyoxyl-32 glycerides, less than about 2.8% w/w of lauroyl polyoxyl-32 glycerides, less than about 9.5% w/w of lauroyl polyoxyl-32 glycerides, from about 1.8% w/w to 19.0% w/w of lauroyl polyoxyl-32 glycerides, from about 3.2% w/w to about 5.8% w/w of lauroyl polyoxyl-32 glycerides, greater than about 1.8% w/w of lauroyl polyoxyl-32 glycerides, greater than about 6.2% w/w of lauroyl polyoxyl-32 glycerides, greater than about 9.5% w/w of lauroyl polyoxyl-32 glycerides, greater than about 10.5% w/w of lauroyl polyoxyl-32 glycerides, and greater than about 19.8% w/w of lauroyl polyoxyl-32 glycerides.

In one embodiment, the present oral compositions can comprise at least one of free of polysorbate, less than 4.5% w/w of polysorbate, from 5.0% w/w to 6.8% w/w of polysorbate, greater than 4.7% w/w of polysorbate greater than 7.7% w/w of polysorbate, and free of polysorbate 80, In one embodiment, the present oral compositions can comprise at least one of free of hydrophilic surfactants, greater than 1.1% w/w of hydrophilic surfactants, free of PEG-40 hydrogenated castor oil, less than 535 mg of PEG-40 hydrogenated castor oil, less than about 4.5% w/w of PEG-40 hydrogenated castor oil, less than about 20.5% w/w of PEG-40 hydrogenated castor oil, less than about 25.5% w/w of PEG-40 hydrogenated castor oil, less than 37.5% w/w of PEG-40 hydrogenated castor oil, from about 26.0% w/w to about 29.8% w/w of PEG-40 hydrogenated castor oil, greater than about 4.9% w/w of PEG-40 hydrogenated castor oil, greater than about 20.8% w/w of PEG-40 hydrogenated castor oil, greater than about 30.2% w/w of PEG-40 hydrogenated castor oil, and greater than about 40.0% w/w of PEG-40 hydrogenated castor oil.

In one embodiment, the present oral compositions can comprise at least one of free of PEG-35 castor oil, less than about 11.8% w/w of PEG-35 castor oil, less than about 12.8% w/w of PEG-35 castor oil, less than about 22.8% w/w of PEG-35 castor oil, less than about 24.7% w/w of PEG-35 castor oil, less than about 25.8% w/w of PEG-35 castor oil, less than about 37.5% w/w of PEG-35 castor oil, less than about 36.4% w/w of PEG-35 castor oil, from about 13.2% w/w to about 26.8% w/w of PEG-35 castor oil from about 23.2% w/w to about 27.8% w/w of PEG-35 castor oil, greater than about 12.2% w/w of PEG-35 castor oil, greater than about 25.3% w/w of PEG-35 castor oil, greater than about 27.3% w/w of PEG-35 castor oil, greater than about 28.3% w/w of PEG-35 castor oil, greater than about 36.8% w/w of PEG-35 castor oil, and greater than about 40.0% w/w of PEG-35 castor oil.

In one embodiment, the present oral compositions can comprise at least one of free of caprylocaproyl polyoxyl-8 glycerides, free of LABRASOL, less than about 62.5% w/w of caprylocaproyl polyoxyl-8 glycerides, and greater than 63.5% w/w of caprylocaproyl polyoxyl-8 glycerides.

In one embodiment, the present oral compositions can comprise at least one of free of PEG-20 corn glycerides (e.g. CROVOL M-40).

In one embodiment, the present oral compositions can comprise at least one of free of tocopherol polyethylene glycol succinate (TPGS), less than about 2.1% w/w of tocopherol polyethylene glycol succinate, less than about 49.4% w/w of tocopherol polyethylene glycol succinate, less than about 70.5% w/w of tocopherol polyethylene glycol succinate, succinate, greater than about 2.5% w/w of tocopherol polyethylene glycol succinate, greater than about 49.8% w/w of tocopherol polyethylene glycol succinate, and greater than 71.5% w/w of tocopherol polyethylene glycol.

In one embodiment, the present oral compositions can comprise at least one of free of alpha-tocopherol, less than about 7.7% w/w of alpha-tocopherol, less than about 26.5% w/w of alpha-tocopherol, less than about 53.5% w/w of alpha-tocopherol, less than about 58.5% w/w of alpha-tocopherol, less than about 59.5% w/w of alpha-tocopherol, less than about 61.5% w/w of alpha-tocopherol, from about 8.0% w/w to about 44.5% w/w of alpha-tocopherol, from about 27.5% w/w to about 58.5% w/w of alpha-tocopherol, from about 54.5% w/w to about 64.5% w/w of alpha-tocopherol, from about 62.5% w/w to about 67.5% w/w of alpha-tocopherol, from about 63.2% w/w to about 68.0% w/w of alpha-tocopherol, from about 59.5% w/w to about 77.5% w/w of alpha-tocopherol, greater than about 1% alpha-tocopherol, greater than about 45.0% w/w of alpha-tocopherol, greater than about 59.5% w/w of alpha-tocopherol, greater than about 65.5% w/w of alpha-tocopherol, greater than about 68.5% w/w of alpha-tocopherol, and greater than about 71.5% w/w of alpha-tocopherol.

In one embodiment, the present oral compositions can comprise less at least one of than 50% w/w of medium chain monoglycerides, free of medium chain mono-/di-glycerides.

In one embodiment, the present oral compositions can comprise at least one of free of caprylic/capric glycerides (e.g. CAPMUL MCM), less than about 6.7% w/w of caprylic/capric glycerides, less than about 7.8% w/w of caprylic/capric glycerides, less than about 65.0% w/w of caprylic/capric glyceride, less than about 73.0% w/w of caprylic/capric glycerides, less than about 80.5% w/w of caprylic/capric glycerides, less than about 82.0% w/w of caprylic/capric glycerides, less than about 83.0% w/w of caprylic/capric glycerides, greater than about 7.0% w/w of caprylic/capric glycerides, greater than about 9.0% w/w of caprylic/capric glycerides, greater than about 10.0% w/w of caprylic/capric glycerides, greater than about 66.0% w/w of caprylic/capric glycerides, greater than about 74.0% w/w of caprylic/capric glycerides, and greater than about 81.0% w/w of caprylic/capric glycerides, greater than about 83.0% w/w of caprylic/capric glycerides, and greater than 84.0% w/w of caprylic/capric glycerides.

In one embodiment, the present oral compositions can comprise at least one of free of glyceryl mono-/di-caprylates (e.g. IMWITOR 988), less than about 10.5% w/w of glyceryl mono-/di-caprylates, from about 11.2% w/w to about 25.5% w/w of glyceryl mono-/di-caprylates, from about 26.0% w/w to about 44.5% w/w of glyceryl mono-/di-caprylates, and greater than about 45.5% w/w of glyceryl mono-/di-caprylates.

In one embodiment, the present oral compositions can comprise at least one of free of lipophilic surfactants, free of linoleoyl polyoxyl-6 glycerides (e.g. LABRAFIL M2125 CS), greater than 1.10% w/w of lipophilic surfactants, and greater than 1.1% w/w of linoleoyl polyoxyl-6 glycerides.

In one embodiment, the present oral compositions can comprise at least one of free of glyceryl monolinoleate (e.g. MAISINE CC) (previously known as MAISINE 35-1), less than about 8.4% w/w of glyceryl monolinoleate, from about 8.8% w/w to about 19.5% w/w of glyceryl monolinoleate, and greater than about 20.5% w/w of glyceryl monolinoleate.

In one embodiment, the present oral compositions can comprise at least one of free of propylene glycol monolaurate (e.g. LAUROGLYCOL), less than about 36.8% w/w of propylene glycol monolaurate, and greater than about 37.2% w/w of propylene glycol monolaurate.

In one embodiment, the present oral compositions can comprise at least one of free of terpene, free of d-limonene, less than about 4.0% w/w of terpene, and greater than about 4.5% w/w of terpene.

In one embodiment, the present oral compositions can comprise at least one of free of medium chain triglycerides, free of caprylic/capric/lauric triglycerides (e.g. CAPTEX 350, MIGLYOL 812), less than about 64.5% w/w of medium chain triglycerides, and greater than about 66.0% w/w of medium chain triglycerides.

In one embodiment, the present oral compositions can comprise at least one of free of glyceryl caprylate (e.g. CAPMUL 708G), less than about 83.0 w/w of glyceryl caprylate, less than about 71.0% w/w of glyceryl caprylate, less than about 72.0% w/w of glyceryl caprylate, greater than about 72.5% w/w of glyceryl caprylate, greater than about 76.5% w/w of glyceryl caprylate, and greater than about 85.0% w/w of glyceryl caprylate.

In one embodiment, the present oral compositions can comprise at least one of free of edible oil, free of peanut oil, free of sunflower oil, free of olive oil, free of almond oil, free of sesame oil, and free of colza oil.

In one embodiment, the present oral compositions can comprise at least one of free of digestible oil, free of fractionated coconut oil, free of soybean oil, less than about 15.8% w/w of fractionated coconut oil, from about 17.4% w/w to about 23.8% w/w of fractionated coconut oil, greater than about 24.2% w/w of fractionated coconut oil, less than about 15.8% w/w of soybean oil, and greater than about 16.2% w/w of soybean oil.

In one embodiment, the present oral compositions can comprise at least one of free of lipophilic solidifying agents, free of hydrogenated castor oil, less than 4.9% w/w of hydrogenated castor oil, and greater than 5.1% w/w of hydrogenated castor oil.

The compositions can have a daily dose of varying amounts. In one aspect, the therapeutically effective amount of the pregn-4-ene-3,20-dione can be orally administered from one time to twelve times per day. In one example, the daily dose of the therapeutically effective amount of the pregn-4-ene-3,20-dione can comprise from about 10 mg to about 400 mg or 25 mg to 150 mg. In another example, the daily dose of the pregn-4-ene-3,20-dione can be a fixed dose of from about 10 mg to about 3400 mg. In another example, the daily dose of the pregn-4-ene-3,20-dione can be a fixed dose of from about 10 mg to about 500 mg. In another example, the daily dose of the pregn-4-ene-3,20-dione can be a fixed dose of from about 10 mg to about 2500 mg. In another example, the daily dose of the pregn-4-ene-3,20-dione can be a fixed dose of from about 10 mg to about 1500 mg. In another example, the daily dose of the pregn-4-ene-3,20-dione can be a fixed dose of from about 10 mg to about 1000 mg. In another example, the daily dose of the pregn-4-ene-3,20-dione can be a fixed dose of from about 10 mg to about 500 mg. In yet another aspect, a daily dose of the pregn-4-ene-3,20-dione can be administered in a capsule form comprising from 1-4 capsules.

In one embodiment the daily dose of therapeutically effective amount of the pregn-4-ene-3,20-dione can comprise at least one of about 25 mg, about 30 mg, about 35 mg, about 40 mg, about 45 mg, about 50 mg, about 55 mg, about 60 mg, about 65 mg, about 70 mg about 75, mg about 80, mg about 85, mg about 90 mg about 95 mg, about 100 mg, about 110 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, and about 200 mg, or any amount within a range from about 25 mg to about 200 mg.

In another aspect, a daily dose of the composition can provide: a 3α-OH-5α-pregnan-20-one maximum serum concentration level ($C_{max}$) of greater than about 8 ng/ml, about 10 ng/ml, about 12 ng/ml, about 15 ng/ml, about 18 ng/ml, about 20 ng/ml, about 25 ng/ml, about 30 ng/ml, about 35 ng/ml, about 40 ng/ml, about 45 ng/ml, about 50 ng/ml, about 60 ng/ml, about 70 ng/ml, about 80 ng/ml, about 90 ng/ml, or any maximum serum concentration level within a range from about 8 ng/ml to about 90 ng/ml.

In another aspect, a daily dose of the composition can provide a 3α-OH-5β-pregnan-20-one maximum serum concentration level ($C_{max}$) of greater than about 6 ng/ml, about 8 ng/ml, about 10 ng/ml, about 12 ng/ml, about 15 ng/ml, about 18 ng/ml, about 20 ng/ml, about 25 ng/ml, about 30 ng/ml, about 35 ng/ml, about 40 ng/ml, about 45 ng/ml, about 50 ng/ml, about 60 ng/ml, about 70 ng/ml, about 80 ng/ml, about 90 ng/ml, or any maximum serum concentration level within a range from about 6 ng/ml to about 90 ng/ml.

In another aspect, a daily dose of the composition can provide: a 30-OH-5α-pregnan-20-one maximum serum concentration level ($C_{max}$) of greater than about 2.5 ng/ml.

In another aspect, a daily dose of the composition can provide a 30-OH-5β-pregnan-20-one maximum serum concentration level ($C_{max}$) of greater than about 2.0 ng/ml.

In one example, an oral pharmaceutical composition comprising pregn-4-ene-3,20-dione can be formulated in a liquid (e.g., a solution, a suspension, an emulsion, a drink, or the like) or in encapsulated gelatin capsule dosage forms or as a tablet. The gelatin capsule can be a soft gelatin capsule or a hard gelatin capsule. The hard gelatin capsule can be a two-piece, standard gelatin capsule including a first capsule portion bottom and a second capsule portion top. The soft gelatin (or other) capsule can be a two-piece capsule wherein two portions are sealed together or a one-piece that is hermetically sealed capsule.

In one aspect, the amount of pregn-4-ene-3,20-dione per capsule can range from about 10 mg to about 400 mg, from about 10 mg to about 200 mg or from about 25 mg to about 150 mg. In one example, the amount of pregn-4-ene-3,20-dione administered to a subject can be about 10 mg, about 15 mg, about 20 mg, about 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, or any amount within a range from about 10 mg to about 200 mg.

In one aspect, the capsule fill amount of the oral pharmaceutical composition can range from about 100 mg to about 1400 mg, about 300 mg to about 1300 mg, or about 400 mg to about 1400 mg. In further aspects, the capsule fill amount of the oral pharmaceutical composition can be about 200 mg, about 300 mg, about 400 mg, about 500 mg, about 600 mg, about 650 mg, about 700 mg, about 750 mg, about 800 mg, about 850 mg, about 900 mg, about 950 mg, about 1,000 mg, about 1,050 mg, about 1,100 mg, about 1,150 mg, about 1,200 mg, about 1,250 mg, about 1,300 mg, about 1,350 mg, about 1,400 mg, or any amount within a range from about 200 mg to about 1400 mg.

In one aspect, the amount of pregn-4-ene-3,20-dione in the composition can range from about 1 weight percent (wt %) to about 9 wt %, about 10 wt % to about 19 wt %, or about 20 wt % to about 25 wt % of the composition. In a further aspect, a subject can be administered the amount of pregn-4-ene-3,20-dione with about 1 wt %, about 1.5 wt %, about 2 wt %, about 2.5 wt %, about 3 wt %, about 3.5 wt %, about 4 wt %, about 4.5 wt %, about 5 wt %, about 5.5 wt %, about 6 wt %, about 6.5 wt %, about 7 wt %, about 7.5 wt %, about 8 wt %, about 8.5 wt %, about 9 wt %, about 9.5 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 t %, about 25 wt % of the composition total fill amount or any wt % of the composition total fill amount within a range from about 1% to about 25%.

In other aspect, the pregn-4-ene-3,20-dione can be administered to a subject (e.g., males and females) to provide a therapeutically effective amount of 3α-OH-5α-pregnan-20-one or 3α-OH-5β-pregnan-20-one. In one example, the pregn-4-ene-3,20-dione in the oral compositions can have a total daily dose that ranges from about 10 mg to about 3400 mg, and about 10 mg, about 15 mg, about 20 mg, about 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 600 mg, about 800 mg, about 1,000 mg, about 1,200 mg, about 1,500 mg, about 1,800 mg, about 2,000 mg, about 2,400 mg, about 2,800 mg, about 3,000 mg, about 3,400 mg, or any amount within a range from about 10 mg to about 3400 mg.

In another aspect, the amount of pregn-4-ene-3,20-dione in a dosage form (e.g., in a capsule) from the oral pharmaceutical composition can range from about 10 mg to about 400 mg, from about 10 mg to about 200 mg or from about 25 mg to about 150 mg or from about 25 mg to about 100 mg. In some aspects, the amount of pregn-4-ene-3,20-dione administered to a subject can be about 10 mg, about 15 mg, about 20 mg, about 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, or any amount within a range from about 10 mg to about 200 mg.

To receive a target amount of the GABA receptor PAM(s) (e.g., 3α-OH-5α-pregnan-20-one or 3α-OH-5β-pregnan-20-one or both) per single dose, in some aspects, the subject can be administered pregn-4-ene-3,20-dione in amounts of from 10 mg to 400 mg, such as about 10 mg, about 15 mg, about 20 mg, about 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 400 mg, or any amount within a range from about 10 mg to about 400 mg or from about 25 mg to about 200 mg.

In one aspect, the therapeutically effective amount of the pregn-4-ene-3,20-dione can be orally administered once daily in any recited amount until the CNS disease or condition is treated. In one aspect, the oral compositions can be administered in the morning, afternoon, evening, or before bedtime. In another aspect, the oral compositions can be administered 5 hours, 4 hours, 3 hours, 2 hours, or 1 hour before bedtime, or at bedtime.

In other aspects, the oral pharmaceutical composition and/or oral dosage forms can be administered twice daily in any of the above noted amounts until the disease or condition is treated. The oral compositions can be administered in the morning and evening, or 12 hours apart. In yet further aspects, the oral pharmaceutical composition or oral dosage form can be administered greater than or equal to three times daily in any of the recited amounts until the disease or condition is treated. The oral compositions or dosage forms can be administered every 8 hours, every 6 hours, every 4 hours, every 3 hours, every 2 hours, or every 1 hour.

In one aspect, the therapeutically effective amount of the pregn-4-ene-3,20-dione can be orally administered to the subject according to a dosage regimen of at least once per day for a specified duration of from about a single day to about 3 months. In another aspect, the oral pharmaceutical composition can be administered for 1 day, 2 days, 3 days, 4 days, 5 days, 6 days, 7 days, 8 days, 9 days, 10 days, 12 days, 14 days, 16 days, 18 days, 20 days, 21 days, 22 days, 24 days, 26 days, or 28, or 30 days until the disease or condition is treated. In one aspect, the oral pharmaceutical compositions can be administered for 1 week, 2 weeks, 3 weeks, 4 weeks, or 5 weeks until the disease or condition is treated. In another aspect, the oral pharmaceutical can be administered for 1 month, 2 months, or 3 months until the disease or condition is treated.

In one aspect, the oral pharmaceutical composition or dosage form can be administered with or without titration. In one aspect, the oral pharmaceutical compositions can be up-titrated by 50%, 100%, 150%, 200%, 300%, 400%, 500% or more than the initial dose. In another aspect, the oral pharmaceutical compositions can be down-titrated by 50% or more than the initial dose. In another aspect, the oral pharmaceutical compositions can be up-titrated and subsequently down-titrated and/or vice versa. In an aspect, the oral pharmaceutical compositions can be administered with the fixed dose or the consistent dose as the initial dose.

In one aspect, the oral pharmaceutical composition or dosage form can be titrated to a subsequent pregn-4-ene-3,20-dione dose based on a pharmacokinetic or pharmacodynamic response to an initial dose by a subject. In one example, the composition or oral dosage form can be orally administered in an initial pregn-4-ene-3,20-dione dose of from about 10 mg to about 200 mg and titrated to a maintenance pregn-4-ene-3,20-dione dose that is about 25% to about 100% higher than the initial dose. In one example, the pregn-4-ene-3,20-dione dose can be increased or decreased from about 0.25× to about 4× from an initial pregn-4-ene-3,20-dione dose to a pregn-4-ene-3,20-dione maintenance dose.

In another aspect the oral pharmaceutical compositions or dosage forms can be administered with or without food, such as meal, snacks, appetizers, or drinks. In one example, administration without food can be during a fasting period of the subject. Food can include various forms including: no fat and no calorie; no fat and low calorie; no fat and medium calorie; no fat and high calorie; low fat and low calorie; low fat and medium calorie; low fat and high calorie; medium fat and low calorie; medium fat and medium calorie; medium fat and high calorie; high fat and medium calorie; or high fat and high calorie. In one aspect, administration with food can be: without high-fat food; with a meal with at least about 5% calories from fat; with a meal with less than about 20% calories from fat; with a meal having from about 20% to about 35% calorie content from fat; or with a meal having from about 35% to about 60% calorie content from fat. The amount of fat and calories can be categorized via the regulations for foods under the Federal Food, Drug, and Cosmetic Act and its amendments.

Methods

In absence of the analyte assay based on chromatography-combined mass spectrometry method (e.g. LC-MS/MS or GC-MS), serum neurosteroid measurements for pregn-4-ene-3,20-dione, and its PAM or NAM metabolites based on an immunoassay are not accurate because the assay is typically not specific to the target analyte. Consequently, data and results related to oral pregn-4-ene-3,20-dione and its neurosteroid, PAM (e.g., 3α-OH-5α-pregnan-20-one, 3α-OH-5β-pregnan-20-one) or NAM (e.g., 3β-OH-5α-pregnan-20-one, 3β-OH-5β-pregnan-20-one) metabolites with respect to levels of PAM and/or NAM generation or the adequacy of PAM and/or NAM levels for desirable GABA receptor modulation. It has been discovered that inducing immediate conversion post oral administration of the pregn-4-ene-3,20-dione prodrug in favor of high PAM and low NAM generation in the GI tract through the present compositions and methods can be effective to produce desirable levels of neurosteroids to treat CNS depression disorders.

In one embodiment, a method of treating a CNS disorder in a subject can include orally administering to the subject, composition comprising a therapeutically effective amount of pregn-4-ene-3,20-dione that provides an amount of 3α-OH-5α-pregnan-20-one, or 3α-OH-5β-pregnan-20-one, or both that is sufficient to treat the CNS depression disorder. In one aspect, a method of treating a CNS disorder in a subject can include orally administering to the subject, composition comprising a therapeutically effective amount of pregn-4-ene-3,20-dione that provides an amount of 3α-OH-5α-pregnan-20-one, or 3α-OH-5β-pregnan-20-one, or both while generating 20% to 100% altered serum levels of isomeric NAM, 3β-OH-5β-pregnan-20-one or a 3β-OH- 5α-pregnan-20-one, that is sufficient to treat the CNS depression disorder. In one aspect, the therapeutically effective amount of pregn-4-ene-3,20-dione can be in a form that provides a therapeutically effective amount of either 3α-OH-5α-pregnan-20-one, or 3α-OH-5β-pregnan-20-one, or a combination thereof for treating the CNS depression disorder in the subject. In another aspect, the therapeutically effective amount of pregn-4-ene-3,20-dione can be in a form that provides a therapeutically effective amount of either 3α-OH-5α-pregnan-20-one, or 3α-OH-5β-pregnan-20-one, or a combination thereof for treating the CNS depression disorder in the subject with at least 20% to 100% altered serum levels of isomeric NAM, 3β-OH-5β-pregnan-20-one or a 3β-OH-5α-pregnan-20-one, for treating the CNS depression disorder in the subject. In another aspect, the pregn-4-ene-3,20-dione can be combined with a carrier that is sufficient to provide a therapeutically effective amount of either 3α-OH-5α-pregnan-20-one, or 3α-OH-5β-pregnan-20-one, or a combination thereof for treating the CNS disorder in the subject. In another aspect, the pregn-4-ene-3,20-dione can be combined with a carrier that is sufficient to provide a therapeutically effective amount of either 3α-OH-5α-pregnan-20-one, or 3α-OH-5β-pregnan-20-one, or a combination thereof with at least 20% to 100% altered serum levels of isomeric NAM, 30-OH-5β-pregnan-20-one or a 3β-OH-5α-pregnan-20-one, for treating the CNS depression disorder in the subject.

In another aspect, the pregn-4-ene-3,20-dione can be in a form that increases formation of either 3α-OH-5α-pregnan-20-one, or 3α-OH-5β-pregnan-20-one, or both as compared to an equivalent amount of a micronized administration. In one example, the formation of either 3α-OH-5α-pregnan-20-one, or 3α-OH-5β-pregnan-20-one, or both can be increased by up to about 8 times as compared to an equivalent amount of a micronized administration.

In one aspect, the CNS disorder can be selected from the group consisting of: post-partum depression, postpartum blues, postpartum substance use addiction disorder, Major Depressive Disorder with a peripartum onset, the like, or combinations thereof.

In another embodiment, a method of treating a CNS disorder in a subject, can include orally administering to the subject, a therapeutically effective amount of pregn-4-ene-3,20-dione that provides an amount of GABA receptor modulating neurosteroid metabolites that is sufficient to treat the CNS disorder. In one aspect, the GABA receptor binding pregn-4-ene-3,20-dione metabolites can be selected from the group consisting of: 3α-OH-5α-pregnan-20-one, a PAM, or 3α-OH-5β-pregnan-20-one, a PAM, or 3β-OH-5α-pregnan-20-one, a NAM, or, 3β-OH-5β-pregnan-20-one, a NAM, the like, or combinations thereof. In another aspect, the GABA receptor binding pregn-4-ene-3,20-dione metabolites can be selected from the group consisting of: 3α-OH-5α-pregnan-20-one, or 3α-OH-5β-pregnan-20-one, the like, or combinations thereof. In another aspect, the GABA receptor binding pregn-4-ene-3,20-dione metabolites can be selected from the group consisting of: 3β-OH-5α-pregnan-20-one, 3β-OH-5β-pregnan-20-one, the like, or combinations thereof.

In one aspect, the subject can have an acute CNS disorder, an episodic CNS disorder, an intermittent CNS disorder, a sub-chronic CNS disorder, a chronic CNS disorder, or combinations thereof. When the CNS disorder is sub-chronic or chronic, the dosage regimen can range from at least once per day for a specified duration of from about a single day to about 3 months, or more than 3 months.

The subjects, in one embodiment, in need of the oral compositions described herein can have CNS disorders, such as depression disorders (e.g., postpartum depression, postpartum substance addiction disorder, major depressive disorder, treatment resistant depression, perinatal depression, perimenopausal or postmenopausal depression), In some embodiments, the oral compositions comprising can be used for the treatment, reduction, or enhancement of conditions, symptoms, or diseases associated with CNS disorders described hereof can be males or females. In one aspect, subjects can be adolescent males or adult males. In further aspects, subjects can be adolescent, adult, female of childbearing age, pre-menopausal, perinatal, postpartum, pregnant, pen-menopausal, or post-menopausal females. In yet another aspect, the subject may not be exhibiting symptoms, but can have diseases associated with CNS disorders described hereof.

Pharmacokinetics and Pharmacodynamics

Serum neurosteroid measurements for pregn-4-ene-3,20-dione, and its PAM or NAM metabolites based on an immunoassay are not accurate because the assay is typically not specific to the target analyte. To measure the target analyte, the assay should be based on chromatography-combined mass spectrometry method (LC-MS/MS or GC-MS), which can provide reliable data to assess the true pharmacokinetic and pharmacodynamic potential of pregn-4-ene-3,20-dione and its PAM and NAM metabolites.

In one example, a single dose administration of the composition or oral dosage form to a subject can provide a $T_{max}$ for pregn-4-ene-3,20-dione, or 3α-OH-5α-pregnan-20-one, or 3α-OH-5β-pregnan-20-one in less than about 1.5 hours, less than about 2 hours, less than about 3 hours, or less than about 4 hours after the oral administration.

In another example, a single dose administration of the composition or oral dosage form to a subject can provide a reduction time of the $C_{max}$ level to one half of the $C_{max}$ level for 3α-OH-5α-pregnan-20-one, or 3α-OH-5β-pregnan-20-one within: about 1 hour, about 3 hours, about 5 hours, about 6 hours, or about 8 hours of the oral administration.

In another example, a single dose administration of the composition or oral dosage form to a subject can provide a 3α-OH-5α-pregnan-20-one maximum serum concentration level ($C_{max}$) of greater than about 8/ng/ml, about 10 ng/ml, about 12 ng/ml, about 15 ng/ml, about 18 ng/ml, about 20 ng/ml, about 25 ng/ml, about 30 ng/ml, about 35 ng/ml, about 40 ng/ml, about 45 ng/ml, about 50 ng/ml, about 60 ng/ml, about 70 ng/ml, about 80 ng/ml, about 90 ng/ml, or maximum serum concentration level within a range from about 8 ng/ml to about 90 ng/ml.

In another example, a single dose administration of the composition or oral dosage form to a subject can provide a 3α-OH-5β-pregnan-20-one maximum serum concentration level ($C_{max}$) of greater than about 6 ng/ml, about 8 ng/ml, about 10 ng/ml, about 12 ng/ml, about 15 ng/ml, about 18 ng/ml, about 20 ng/ml, about 25 ng/ml, about 30 ng/ml, about 35 ng/ml, about 40 ng/ml, about 45 ng/ml, about 50 ng/ml, about 60 ng/ml, about 70 ng/ml, about 80 ng/ml, about 90 ng/ml, or maximum serum concentration level within a range from about 8 ng/ml to about 90 ng/ml.

In another example, a single dose administration of the composition or oral dosage form to a subject can provide a ratio of $C_{max}$ for 3α-OH-5α-pregnan-20-one (ng/ml) to $C_{max}$ for pregn-4-ene-3,20-dione (ng/ml) of greater than about 1:1, greater than about 2:1, greater than about 3:1, greater than about 4:1, greater than about 5:1, greater than about 10:1, greater than about 20:1, greater than about 30:1, greater than about 40:1, or greater than about 50:1.

In another example, a single dose administration of the composition or oral dosage form to a subject can provide a ratio of $C_{max}$ for 3α-OH-5β-pregnan-20-one (ng/ml) to $C_{max}$ for pregn-4-ene-3,20-dione (ng/ml) of greater than about 1:1, greater than about 2:1, greater than about 3:1, greater than about 4:1, greater than about 5:1, greater than about 10:1, greater than about 20:1, greater than about 30:1, greater than about 40:1, or greater than about 50:1.

In another example, a single dose administration of the composition or oral dosage form to a subject can provide a ratio of a sum of $C_{max}$ for 3α-OH-5α-pregnan-20-one (ng/ml) and 3α-OH-5β-pregnan-20-one (ng/ml) to $C_{max}$ for pregn-4-ene-3,20-dione (ng/ml) of greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1, or greater than 100:1.

In another example, a single dose administration of the composition or oral dosage form to a subject can provide a ratio of $C_{max}$ for 3α-OH-5α-pregnan-20-one (ng/ml) to $C_{max}$ for 3β-OH-5α-pregnan-20-one (ng/ml) of from about 1.2 to about 10.0.

In another example, a single dose administration of the composition or oral dosage form to a subject can provide a ratio of $C_{max}$ for 3α-OH-5β-pregnan-20-one (ng/ml) to $C_{max}$ for 3β-OH-5β-pregnan-20-one (ng/ml) of from about 1.2 to about 10.0.

In another example, a single dose administration of the composition or oral dosage form to a subject can provide a ratio of a sum of $C_{max}$ for 3α-OH-5α-pregnan-20-one (ng/ml) and 3α-OH-5β-pregnan-20-one (ng/ml) to a sum of $C_{max}$ for 3β-OH-5α-pregnan-20-one (ng/ml) and 3β-OH-5β-pregnan-20-one (ng/ml) of about 1.2 to about 10.0.

In another example, a single dose administration of the composition or oral dosage form to a subject can provide a ratio of $C_{max}$ of 3α-OH-5α-pregnan-20-one (ng/ml) to daily dose of pregn-4-ene-3,20-dione (mg) of from about $7.5 \times 10^{-8}$/ml to about $2.5 \times 10^{-6}$/ml. In another example, a single dose administration of the composition to a subject can provide a ratio of $C_{max}$ of 3α-OH-5β-pregnan-20-one (ng/ml) to daily dose of pregn-4-ene-3,20-dione (mg) of from about $5.0 \times 10^{-8}$/ml to about $2.5 \times 10^{-6}$/ml. In another example, a single dose administration of the composition to a subject can provide a ratio of sum of $C_{max}$ for 3α-OH-5α-pregnan-20-one (ng/ml) and 3α-OH-5β-pregnan-20-one (ng/ml) to daily dose of pregn-4-ene-3,20-dione (mg) of from about $1.3 \times 10^{-7}$/ml to about $5.0 \times 10^{-6}$/ml.

In one example, the oral compositions or dosage forms and methods can provide a $C_{max}$ of 3α-OH-5α-pregnan-20-one of about 8 ng/ml to 90 ng/ml or about 18 ng/ml to 80 ng/ml, such as at least about 18 ng/ml, about 20 ng/ml, about 22 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, about 75 ng/ml, about 80 ng/ml, or greater than about 80 ng/ml. In another example, the oral compositions and methods can provide a $C_{max}$ of 3α-OH-5β-pregnan-20-one of about 6 ng/ml-90 ng/ml or about 11 ng/ml-80 ng/ml, such as at least about 11 ng/ml, about 13 ng/ml, about 15 ng/ml, about 18 ng/ml, about 20 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, or greater than 80 ng/ml. In yet further example, the oral compositions and methods can provide a total $C_{max}$ of 3α-OH-5α-pregnan-20-one and 3α-OH-5-pregnan-20-one of about 14 ng/ml-180 ng/ml or about 28 ng/ml-160 ng/ml, such as at least about 28 ng/ml, about 30 ng/ml, about 35 ng/ml, about 40 ng/ml, about 45 ng/ml, about 50 ng/ml, about 60 ng/ml, about 70 ng/ml, about 80 ng/ml, about 90 ng/ml, about 100 ng/ml, about 110 ng/ml, about 120 ng/ml, about 130 ng/ml, about 140 ng/ml, about 150 ng/ml, or greater than about 160 ng/ml.

In another example, a single dose administration of the oral compositions or dosage forms and methods to a subject can provide a ratio of $C_{max}$ for 3α-OH-5β-pregnan-20-one (ng/ml) to $C_{max}$ for pregn-4-ene-3,20-dione (ng/ml) of greater than about 1:1, greater than about 2:1, greater than about 3:1, greater than about 4:1, greater than about 5:1, greater than about 6:1, greater than about 7:1, greater than about 8:1, greater than about 9:1, or greater than about 10:1, greater than about 20:1, greater than about 30:1, greater than about 40:1, or greater than about 50:1.

In another example, a single dose administration of the oral compositions or dosage forms and methods to a subject can provide a ratio of $C_{max}$ for 3α-OH-5α-pregnan-20-one (ng/ml) to $C_{max}$ for pregn-4-ene-3,20-dione (ng/ml) of greater than about 1:1, greater than about 2:1, greater than about 3:1, greater than about 4:1, greater than about 5:1, greater than about 6:1, greater than about 7:1, greater than about 8:1, greater than about 9:1, or greater than about 10:1, greater than about 20:1, greater than about 30:1, greater than about 40:1, or greater than about 50:1.

In another example, a single dose administration of the oral compositions or dosage forms and methods to a subject can provide a ratio of a sum of $C_{max}$ for 3α-OH-5α-pregnan-20-one (ng/ml) and 3α-OH-5β-pregnan-20-one (ng/ml) to $C_{max}$ for pregn-4-ene-3,20-dione (ng/ml) of greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1, or greater than 100:1.

In another example, a single dose administration of the oral compositions or dosage forms and methods to a subject can provide a ratio of $C_{max}$ of 3α-OH-5α-pregnan-20-one (ng/ml) to daily dose of pregn-4-ene-3,20-dione (mg) of from about $7.5 \times 10^{-8}$/ml to about $2.5 \times 10^{-6}$/ml. In another example, a single dose administration of the oral compositions or dosage forms and methods to a subject can provide a ratio of $C_{max}$ of 3α-OH-5β-pregnan-20-one (ng/ml) to daily dose of pregn-4-ene-3,20-dione (mg) of from about $5.0 \times 10^{-8}$/ml to about $2.5 \times 10^{-6}$/ml. In another example, a single dose administration of the oral compositions or dosage forms and methods to a subject can provide a ratio of sum of $C_{max}$ for 3α-OH-5α-pregnan-20-one (ng/ml) and 3α-OH-5β-pregnan-20-one (ng/ml) to daily dose of pregn-4-ene-3,20-dione (mg) of from about $1.3 \times 10^{-7}$/ml to about $5.0 \times 10^{-6}$/ml.

In another example, a single dose administration of the oral compositions or dosage forms and methods to a subject can provide a ratio of $C_{max}$ for 3α-OH-5α-pregnan-20-one (ng/ml) to $C_{max}$ for 3β-OH-5α-pregnan-20-one (ng/ml) of from about 1.2 to about 10.0.

In another example, a single dose administration of the oral compositions or dosage forms and methods to a subject can provide a ratio of $C_{max}$ for 3α-OH-5β-pregnan-20-one (ng/ml) to $C_{max}$ for 3β-OH-5p-pregnan-20-one (ng/ml) of from about 1.2 to about 10.0.

In another example, a single dose administration of the oral compositions or dosage forms and methods to a subject can provide a ratio of a sum of $C_{max}$ for 3α-OH-5α-pregnan-20-one (ng/ml) and 3α-OH-5β-pregnan-20-one (ng/ml) to a sum of $C_{max}$ for 3β-OH-5α-pregnan-20-one (ng/ml) and 3β-OH-5β-pregnan-20-one (ng/ml) of about 1.2 to about 10.0.

In another example, a single dose administration of the composition or oral dosage form and methods to a subject can provide a daily $C_{avg}$ of 3α-OH-5α-pregnan-20-one or 3α-OH-5β-pregnan-20-one serum concentration of greater than about 4 ng/ml.

In another example, a single dose administration of the composition or oral dosage form and methods to a subject can provide sum of daily $C_{avg}$ of 3α-OH-5β-pregnan-20-one and 3α-OH-5β-pregnan-20-one serum concentration of greater than about 8 ng/ml.

In another example, a single dose administration of the composition or oral dosage form and methods to a subject can provide a ratio of daily $C_{avg}$ for 3α-OH-5α-pregnan-20-one (ng/ml) to daily $C_{avg}$ for pregn-4-ene-3,20-dione (ng/ml) of greater than about 1:1, greater than about 2:1, greater than about 3:1, greater than about 4:1, greater than about 5:1, greater than about 6:1, greater than about 7:1, greater than about 8:1, greater than about 9:1, or greater than about 10:1, greater than about 20:1, greater than about 30:1, greater than about 40:1, or greater than about 50:1.

In another example, a single dose administration of the composition or oral dosage form and methods to a subject can provide a ratio of daily $C_{avg}$ for 3α-OH-5β-pregnan-20-one (ng/ml) to daily $C_{avg}$ for pregn-4-ene-3,20-dione (ng/ml) of greater than about 1:1, greater than about 2:1, greater than about 3:1, greater than about 4:1, greater than about 5:1, greater than about 6:1, greater than about 7:1, greater than about 8:1, greater than about 9:1, or greater than about 10:1, greater than about 20:1, greater than about 30:1, greater than about 40:1, or greater than about 50:1.

In another example, a single dose administration of the composition or oral dosage form and methods to a subject can provide a ratio of a sum of daily $C_{avg}$ for 3α-OH-5α-pregnan-20-one (ng/ml) and 3α-OH-5β-pregnan-20-one (ng/ml) to daily $C_{avg}$ for pregn-4-ene-3,20-dione (ng/ml) of greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1, or greater than 100:1.

In another example, a single dose administration of the oral compositions or dosage forms and methods to a subject can provide a ratio of daily $C_{avg}$ of 3α-OH-5α-pregnan-20-one (ng/ml) to daily dose of pregn-4-ene-3,20-dione (mg) of from about $1.0 \times 10^{-8}$/ml to about $1.0 \times 10^{-6}$/ml. In another example, a single dose administration of the oral compositions or dosage forms and methods to a subject can provide a ratio of daily $C_{avg}$ of 3α-OH-5β-pregnan-20-one (ng/ml) to daily dose of pregn-4-ene-3,20-dione (mg) of from about $1.0 \times 10^{-8}$/ml to about $1.0 \times 10^{-6}$/ml. In another example, a single dose administration of the oral compositions or dosage forms and methods to a subject can provide a ratio of sum of daily $C_{avg}$ for 3α-OH-5α-pregnan-20-one (ng/ml) and 3α-OH-5β-pregnan-20-one (ng/ml) to daily dose of pregn-4-ene-3,20-dione (mg) of from about $2.0 \times 10^{-8}$/ml to about $2.0 \times 10^{-6}$/ml.

In another example, a single dose administration of the composition or dosage form to a subject can provide a treatment that occurs in less than about 1 hour or about 2 hours. In one aspect, the oral compositions and methods can provide the onset of CNS activity in less than about 1 hour to about 5 hour, such as about less than 1 hour, about 1 hour to about 1.5 hours, about 2 hours, about 2.5 hours, about 3 hours, about 3.5 hours, about 4 hours, about 4.5 hours, or about 5 hours.

In another example, a single dose administration of the composition or oral dosage form to a subject can provide a treatment that occurs for greater than about 2 hours after administration, about 4 hours after administration, about 8 hours after administration, about 24 hours after administration, or about 2 days after administration. In some aspects, the oral compositions and methods can maintain the duration of CNS activity for at least from about 1 hour to 24 hours, about 1 day to 30 days, about 1 week to 12 weeks, or about 1 month to 6 months. In one example, the oral compositions and methods can maintain the duration of CNS activity from about 1 hour to 24 hours, such as at least about 1 hour, about 2 hours, about 3 hours, about 4 hours, about 5 hours, about 6 hours, about 7 hours, about 8 hours, about 9 hours, about 10 hours, about 11 hours, about 12 hours, about 14 hours, about 16 hours, about 18 hours, about 20 hours, about 22 hours, or about 24 hours.

In another example, the duration of CNS activity can be maintained from about 1 day to 30 days, such as at least about 1 day, about 2 day, about 3 days, about 4 days, about 5 days, about 6 days, about 7 days, about 8 days, about 9 days, about 10 days, about 11 days, about 12 days, about 15 days, about 18 days, about 21 days, about 24 days, about 25 days, about 28 days, or about 30 days. In another example, the oral compositions and methods can maintain the duration of CNS activity from about 1 week to 12 weeks, such as at least about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In yet a further example, the oral compositions and methods can maintain the duration of CNS activity from about 1 month to 6 months, such as at least about 1 month, about 2 months, about 3 months, about 4 months, about 5 months, or about 6 months.

A baseline 17-item HAM-D (Hamilton Depression Rating) score of between 20 and 25 can be associated with moderate depression and a 17-item HAM-D score of greater than about 25 can be associated with severe depression. In one example, oral administration of the composition or dosage form to a subject can reduce a 17-item HAM-D score in a subject by about 3, about 4, about 5, about 6, about 7, about 8, about 9, or about 10, or about 15, or about 20 as compared to baseline when measured at about 1 day to about 45 days after commencement of treatment. In another aspect, the oral compositions and methods can provide a reduction in the HAM-D score by at least about 2.0 or 2.5 compared to the score in the placebo treatment (change from baseline), such as by about 2.0, about 2.5, about 3.0, about 3.5, about 4.0, about 4.5, about 5.0, or greater than about 5.0, when measured post treatment. In one aspect, the oral compositions and methods can provide a reduction in HAM-D score by least about 1.5 or 2.0 compared to the score in the placebo treatment (change from baseline), such as by about 2.0, about 2.5, about 3.0, about 3.5, about 4.0, about 4.5, about 5.0, and greater than about 5.0, at one of 3, 4, 5, 6, 7, 8, 9, 10, 11, 12, 13, 14, 15, 16, 17, 18, 19, 20, 21, 22, 23, 24, 25, 26, 27, 28, 29, 30 or 45 days when measured after commencement of treatment.

In another example, a single dose administration of the composition or oral dosage form and methods to a subject can induce remission of the disease through reduction in a 17-item HAM-D total score in a subject (e.g. total score reduced to <=7) as compared to the baseline at commencement of treatment when measured at about 3 days to about 28 days after commencement of treatment.

In another example, a single dose administration of the composition or oral dosage form and methods to a subject can reduce a 17-item HAM-D score in a subject by at least about 2, about 3, about 4, about 5, about 6, about 7, about 8, about 9, about 10, about 10, about 11, about 12, about 13, about 14, about 15 about 20 as compared to the baseline at commencement of treatment when measured at about 3 days to about 28 days after commencement of treatment. In some examples, the oral compositions and methods can provide a reduction in HAM-D score by at least about 3.0 from the baseline, such as about 3.0, about 3.5, about 4.0, about 4.5, about 5.0, about 5.5, about 6.0, about 6.5, about 7.0, about 7.5, about 8.0, about 8.5, about 9.0, about 9.5, about 10, or greater than about 10 at the efficacy date post treatment. In one example, the oral compositions and methods can provide a reduction in HAM-D score by at least about 2.0 or 2.5 from the baseline, such as about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10, and greater than about 10, at one of 3, 4, 5, 6, 7, 8, 9, 10, 11, 12, 13, 14, 15, 16, 17, 18, 19, 20, 21, 22, 23, 24, 25, 26, 27, 28, 29, or 30 days post administration. In another aspect, the oral compositions or dosage forms and methods can provide a reduction in the HAM-D score by at least about 2.0 or 2.5 compared to the score in the placebo treatment (change from baseline), such as by about 2.0, about 2.5, about 3.0, about 3.5, about 4.0, about 4.5, about 5.0, or greater than about 5.0, when measured post treatment. In one aspect, the oral compositions or dosage forms and methods can provide a reduction in HAM-D score by least about 1.5 or 2.0 compared to the score in the placebo treatment, such as by about 1.5, about 2.0, about 2.5, about 3.0, about 3.5, about 4.0, about 4.5, about 5.0, and greater than about 5.0, at one of 3, 4, 5, 6, 7, 8, 9, 10, 11, 12, 13, 14, 15, 16, 17, 18, 19, 20, 21, 22, 23, 24, 25, 26, 27, 28, 29, 30 or 45 days when measured post treatment (change from baseline).

In another example, a single dose administration of the composition or oral dosage form and methods to a subject can induce remission of the disease through reduction in MADRS score as compared to the baseline at commencement of treatment when measured at about 3 days to about 28 days after commencement of treatment. In one aspect, the oral compositions and methods can provide a reduction from the baseline in MADRS score by at least greater than about 3, about 4, about 5, about 6, about 7, about 8, about 9, about 10, about 15, or about 20 as compared to baseline when measured at about 1 day to about 45 days after commencement of treatment to a subject with MADRS score >20.

In another example, a single dose administration of the composition or oral dosage form and methods to a subject can induce remission of the disease through reduction in EPDS score as compared to the baseline at commencement of treatment when measured at about 3 days to about 28 days after commencement of treatment. In one aspect, the oral compositions and methods can provide a reduction from the baseline in MADRS score by at least greater than about 2, about 3, about 4, about 5, about 6, about 7, about 8, about 9, or about 10 as compared to baseline when measured at about 1 day to about 45 days after commencement of treatment to a subject with MADRS score >10.

Examples

The following examples are provided to promote a clearer understanding of certain invention embodiments, and are in no way meant as a limitation thereon.

Example 1—Pregn-4-ene-3, 20-dione Compositions

TABLE 1A

Vitamin E or its derivative-comprising compositions

| Component | Composition 1A (w/w %) | | | |
| --- | --- | --- | --- | --- |
| | I | II | III | IV |
| Pregn-4-ene-3,20-dione | 20-25 | 15-19 | 10-14 | 1-9 |
| Vitamin E or its derivative (e.g., TPGS, tocopherol, tocopherol acetate, tocotrienol, or a combination) | 10-80 | 10-85 | 10-90 | 2-99 |
| Other carrier ingredients* | q.s. | q.s. | q.s. | q.s. |

TABLE 1B

Fatty acid or its salt-comprising compositions

| Component | Composition 1B (w/w %) | | | |
| --- | --- | --- | --- | --- |
| | I | II | III | IV |
| Pregn-4-ene-3,20-dione | 20-25 | 15-19 | 10-14 | 1-9 |
| Fatty acid or its salt (e.g., oleic acid, linoleic acid, lauric acid, myristic acid, octanoic acid, capric acid, sodium octanoate, sodium caprate, sodium oleate, sodium lauroyl lactylate, sodium stearoyl lactylate, sodium laurate, or a combination) | 30-80 | 30-85 | 30-90 | 30-99 |
| Other carrier ingredients | q.s. | q.s. | q.s. | q.s. |

TABLE 1C

Glyceryl fatty acid ester-comprising compositions

| Component | Composition 1C (w/w %) | | | |
| --- | --- | --- | --- | --- |
| | I | II | III | IV |
| Pregn-4-ene-3,20-dione | 20-25 | 15-19 | 10-14 | 1-9 |
| Glyceryl fatty acid ester (e.g., Capmul MCM, Capmul MCM C8, Capmul 808G, Capmul GMO-50, Capmul 708G, Imwitor 308, Imwitor 382 P, Imwitor 375, Imwitor 742, Imwitor 988, Myvacet 9-45, Maisine 35-1, Maisine CC, or a combination) | 30-80 | 30-85 | 30-90 | 30-99 |
| Other carrier ingredients | q.s. | q.s. | q.s. | q.s. |

TABLE 1D

Polyglycerol fatty acid ester-comprising compositions

| Component | Composition 1D (w/w %) | | | |
|---|---|---|---|---|
| | I | II | III | IV |
| Pregn-4-ene-3,20-dione | 20-25 | 15-19 | 10-14 | 1-9 |
| Polyglycerol fatty acid ester (e.g., Caprol PGE-860, Plurol Oleique CC 497, Caprol MPGO, Caprol 3GO, Caprol 6GC8, Caprol 10G10O, Caprol ET, Drewpol 10-10-O, or a combination) | 30-80 | 30-85 | 30-90 | 30-99 |
| Other carrier ingredients | q.s. | q.s. | q.s. | q.s. |

TABLE 1E

PEG glyceride of fatty acid ester-comprising compositions

| Component | Composition 1E (w/w %) | | | |
|---|---|---|---|---|
| | I | II | III | IV |
| Pregn-4-ene-3,20-dione | 20-25 | 15-19 | 10-14 | 1-9 |
| PEG glyceride of fatty acid ester (e.g., Gelucire 44/14, Gelucire 50/13, Acconon CC-6, Acconon CO-7, Acconon C-30, Acconon C-80, Acconon E, Lipopeg 2-DL, Labrafac PG, TEFOSE 63, Labrafil M2125CS, Labrafil M1944CS, Labrasol, Acconon MC8-2, Acconon C-44, Acconon C-50, Acconon AKG-6, Labrafil M2130CS, Compritol HD 5 ATO or a combination) | 30-80 | 30-85 | 30-90 | 30-99 |
| Other carrier ingredients | q.s. | q.s. | q.s. | q.s. |

TABLE 1F

Triglyceride-comprising compositions

| Component | Composition 1F (w/w %) | | | |
|---|---|---|---|---|
| | I | II | III | IV |
| Pregn-4-ene-3,20-dione | 20-25 | 15-19 | 10-14 | 1-9 |
| Triglyceride (e.g., Captex 300, Captex 300 Low C6, Captex 350, Captex 355, Miglyol 808, Miglyol 810, Miglyol 812, Miglyol 818, Miglyol 829, Labrafac Lipophile WL 1349, or a combination) | 30-80 | 30-85 | 30-90 | 30-99 |
| Other carrier ingredients | q.s. | q.s. | q.s. | q.s. |

TABLE 1G

Hydrogenated polyoxyl vegetable oil or glyceride-comprising compositions

| Component | Composition 1G (w/w %) | | | |
|---|---|---|---|---|
| | I | II | III | IV |
| Pregn-4-ene-3,20-dione | 20-25 | 15-19 | 10-14 | 1-9 |
| Hydrogenated polyoxyl vegetable oil or glyceride (e.g., Kolliphor EL, Kolliphor RH40, Etocas 40, Croduret 60, Kolliphor HS 15, Etocas 5, Sterotex, Sterotex HM, Sterotex K, or a combination) | 1-50 | 1-50 | 1-50 | 1-50 |
| Other carrier ingredients | q.s. | q.s. | q.s. | q.s. |

TABLE 1H

Propylene glycol fatty acid ester-comprising compositions

| Component | Composition 1H (w/w %) | | | |
|---|---|---|---|---|
| | I | II | III | IV |
| Pregn-4-ene-3,20-dione | 20-25 | 15-19 | 10-14 | 1-9 |
| Propylene glycol fatty acid ester (e.g., Lauroglycol 90, Captex 100, Captex 200, Miglyol 840, Neobee M-20, Capmul PG-8, Capmul PG-12, Capmul PG-2L, Capryol 90, Acconon E, or a combination) | 30-80 | 30-85 | 30-90 | 30-99 |
| Other carrier ingredients | q.s. | q.s. | q.s. | q.s. |

TABLE 1I

Edible oil-comprising compositions

| Component | Composition 1I (w/w %) | | | |
|---|---|---|---|---|
| | I | II | III | IV |
| Pregn-4-ene-3,20-dione | 20-25 | 15-19 | 10-14 | 1-9 |
| Edible oil (e.g., peppermint oil, borage oil, soybean oil, olive oil, coconut oil, omega-3 oil, castor oil, and so on) | 30-80 | 30-85 | 30-90 | 30-99 |
| Other carrier ingredients | q.s. | q.s. | q.s. | q.s. |

Other carrier ingredients in Example 1 can be hydrophilic additives, lipophilic additives, co-solvents, other functional additives, or combinations thereof if needed. Co-solvents can be at least one or a combination of: alcohol, glycerin, glycofural, triacetin, trimethyl citrate, propylene glycol, polyethylene glycol, sorbitol, dimethylacetamide, and dimethylsulfoxide.

Example 2—Pregn-4-ene-3, 20-dione Compositions with Lipophilic Additives

TABLE 2A

Vitamin E or its derivative-comprising compositions

| Ingredient | | Composition 2A (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Pregn-4-ene-3,20-dione | | 1-10 | 1-10 | 1-10 | 1-10 | 1-10 | 1-10 | 1-10 | 1-10 | 1-10 | 1-10 | 1-10 | 1-10 | 1-10 | 1-10 |
| Vitamin E or its derivative (e.g., TPGS, tocopherol, tocopherol acetate, tocotrienol, Tocophersolan, and so on) | | 30-50 | 10-22 | 10-22 | 10-22 | 10-22 | 10-22 | 10-22 | 10-22 | 10-22 | 10-22 | 10-22 | 10-22 | 10-22 | 10-22 |
| Lipophilic additives | Glyceryl fatty acid ester (e.g., Capmul MCM C8, Capmul 808G, Imwitor 988, Maisine CC, and so on) | 30-50 | 30-50 | 30-50 | | | | | | | | | | | 18-54 |

TABLE 2A-continued

Vitamin E or its derivative-comprising compositions

Composition 2A (w/w %)

| Ingredient | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Polyglycerol fatty acid ester (e.g., Caprol PGE-860, Plurol Oleique CC 497, Caprol 3GO, Caprol 10G10O, Caprol ET, and so on) | | | 18-54 | 68-89 | 30-50 | | 18-54 | | | | 18-54 | | | |
| Triglyceride (e.g., Captex 300, Captex 300 Low C6, Captex 350, Miglyol 810, Miglyol 812, and so on) | | | | | | 68-89 | 30-50 | | 18-54 | | | | | |
| Propylene glycol fatty acid ester (e.g., Lauroglycol 90, Captex 100, Capmul PG-8, Capmul PG-12, Capryol 90, Acconon E, and so on) | | 18-54 | | | 18-54 | | | 68-89 | 30-50 | | | 18-54 | | |
| Fatty acid or its salt (e.g., oleic acid, linoleic acid, lauric acid, octanoic acid, sodium caprate, sodium laurate, and so on) | | | | | | | | | | 68-89 | 30-50 | | | |
| Edible oil (e.g., borage oil, peppermint oil, olive oil, coconut oil, omega-3 oil, and so on) | | | | | | | | | | | | 68-89 | 30-50 | 30-50 |
| Other carrier ingredients | q.s. | q.s. | q.s. | q.s. | q.s. | q.s. | q.s. | q.s. | q.s. | q.s. | q.s. | q.s. | q.s. | q.s. |

TABLE 2B

Glyceryl fatty acid ester-comprising compositions

Composition 2B (w/w %)

| Ingredient | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Pregn-4-ene-3,20-dione | | 1-10 | 1-10 | 1-8 | 1-8 | 1-8 | 1-8 | 1-8 | 1-8 | 1-8 | 1-8 | 1-8 | 1-8 | 1-8 | 1-8 |
| Glyceryl fatty acid ester (e.g., Capmul MCM C8, Capmul MCM, Capmul 808G, Imwitor 988, Maisine CC, and so on) | | 30-85 | 30-49 | 30-49 | 30-49 | 30-49 | 30-49 | 30-49 | 30-49 | 30-49 | 30-49 | 30-49 | 30-49 | 30-49 | 30-49 |
| Lipophilic additives | Vitamin E or its derivative (e.g., TPGS, tocopherol acetate, tocotrienol, and so on) | 1-30 | 20-40 | | | | 11-40 | | | | | | | | 11-40 |
| | Polyglycerol fatty acid ester (e.g., Caprol PGE-860, Plurol Oleique CC 497, Caprol 3GO, Caprol 10G10O, Caprol ET, and so on) | | | 41-60 | 30-40 | | | | | | | | 3-20 | | |
| | Triglyceride (e.g., Captex 300, Captex 300 Low C6, Captex 350, Miglyol 810, Miglyol 812, and so on) | | | | | 41-60 | 30-40 | | 11-40 | | | | | | |
| | Propylene glycol fatty acid ester (e.g., Lauroglycol 90, Captex 100, Capmul PG-8, Capmul PG-12, Capryol 90, Acconon E, and so on) | | 2-40 | | | | | 41-60 | 30-40 | 30-40 | | 11-40 | | | |
| | Fatty acid or its salt (e.g., oleic acid, linoleic acid, lauric acid, octanoic acid, sodium caprate, sodium laurate, and so on) | | | | | | | | | | 41-60 | 30-40 | | | |
| | Edible oil (e.g., borage oil, peppermint oil, olive oil, coconut oil, omega-3 oil, and so on) | | | | 11-40 | | | | 11-40 | | | | | 41-60 | 30-40 |
| Other carrier ingredients | | q.s. | q.s. | q.s. | q.s. | q.s. | q.s. | q.s. | q.s. | q.s. | q.s. | q.s. | q.s. | q.s. | q.s. |

TABLE 2C

Polyglycerol fatty acid ester-comprising compositions

| | | Composition 2C (w/w %) | | | | | | | | | | | | | |
|---|---|---|---|---|---|---|---|---|---|---|---|---|---|---|---|
| Ingredient | | 1 | 2 | 3 | 4 | 5 | 6 | 7 | 8 | 9 | 10 | 11 | 12 | 13 | 14 |
| Pregn-4-ene-3,20-dione | | 1-8 | 1-6 | 1-6 | 1-5 | 1-5 | 1-5 | 1-5 | 1-5 | 1-5 | 1-5 | 1-5 | 1-5 | 1-5 | 1-5 |
| Polyglycerol fatty acid ester (e.g., Caprol PGE-860, Plurol Oleique CC 497, Caprol 3GO, Caprol 10G10O, Caprol ET, and so on) | | 3-49 | 30-49 | 30-49 | 30-49 | 30-49 | 30-49 | 30-49 | 30-49 | 30-49 | 30-49 | 30-49 | 30-49 | 30-49 | 30-49 |
| Lipophilic additives | Vitamin E or its derivative (e.g., TPGS, tocopherol acetate, tocotrienol, and so on) | 41-68 | 30-40 | | | | 11-40 | | | | | 11-40 | | | 11-40 | 11-40 |
| | Glyceryl fatty acid ester (e.g., Capmul MCM C8, Capmul 808G, Imwitor 988, Maisine CC, and so on) | | | 41-60 | 30-40 | | | | | | | 11-40 | | | | |
| | Triglyceride (e.g., Captex 300, Captex 300 Low C6, Captex 350, Miglyol 810, Miglyol 812, and so on) | | 11-40 | | | 41-60 | 30-40 | | 11-40 | | | | | | | |
| | Propylene glycol fatty acid ester (e.g., Lauroglycol 90, Captex 100, Capmul PG-8, Capmul PG-12, Capryol 90, Acconon E, and so on) | | | | | | | 41-60 | 30-40 | 30-40 | | | | | | |
| | Fatty acid or its salt (e.g., oleic acid, linoleic acid, lauric acid, octanoic acid, sodium caprate, sodium laurate, and so on) | | | | | | | | | | 41-60 | 30-40 | 30-40 | | | |
| | Edible oil (e.g., borage oil, peppermint oil, olive oil, coconut oil, omega-3 oil, and so on) | | | | 11-40 | | | | 11-40 | | | | | 41-60 | 30-40 | |
| Other carrier ingredients | | q.s. | q.s. | q.s. | q.s. | q.s. | q.s. | q.s. | q.s. | q.s. | q.s. | q.s. | q.s. | q.s. | q.s |

TABLE 2D

Triglyceride-comprising compositions

| | | Composition 2D (w/w %) | | | | | | | | | | | | | |
|---|---|---|---|---|---|---|---|---|---|---|---|---|---|---|---|
| Ingredient | | 1 | 2 | 3 | 4 | 5 | 6 | 7 | 8 | 9 | 10 | 11 | 12 | 13 | 14 |
| Pregn-4-ene-3,20-dione | | 1-10 | 1-8 | 1-6 | 1-5 | 1-5 | 1-5 | 1-5 | 1-5 | 1-5 | 1-5 | 1-5 | 1-5 | 1-5 | 1-5 |
| Triglyceride (e.g., Captex 300, Captex 300 Low C6, Captex 350, Miglyol 810, Migyol 812, and so on) | | 30-49 | 30-49 | 30-49 | 30-49 | 30-49 | 30-49 | 30-49 | 30-49 | 30-49 | 30-49 | 30-49 | 30-49 | 30-49 | 30-49 |
| Lipophilic additives | Vitamin E or its derivative (e.g., TPGS, tocopherol acetate, tocotrienol, and so on) | 41-60 | 30-40 | | | | | | | | | | 11-40 | | 11-40 |
| | Glyceryl fatty acid ester (e.g., Capmul MCM C8, Capmul 808G, Imwitor 988, Maisine CC, and so on) | | | 41-60 | 30-40 | | | | 11-40 | | | | | | |
| | Polyglycerol fatty acid ester (e.g., Caprol PGE-860, Plurol Oleique CC 497, Caprol 3GO, Caprol 10G10O, Caprol ET, and so on) | | | | | | 41-60 | 30-40 | | | | | | | |
| | Propylene glycol fatty acid ester (e.g., Lauroglycol 90, Captex 100, Capmul PG-8, Capmul PG-12, Capryol 90, Acconon E, and so on) | | 11-40 | | | 11-40 | 41-60 | 30-40 | 30-40 | | | 11-40 | | | |
| | Fatty acid or its salt (e.g., oleic acid, linoleic acid, lauric acid, octanoic acid, sodium caprate, sodium laurate, and so on) | | | | 11-40 | | | | | | 41-60 | 30-40 | 30-40 | | |
| | Edible oil (e.g., borage oil, peppermint oil, olive oil, coconut oil, omega-3 oil, and so on) | | | | | | | | | 11-40 | | | | 41-60 | 30-40 |
| Other carrier ingredients | | q.s. | q.s. | q.s. | q.s. | q.s. | q.s. | q.s. | q.s. | q.s. | q.s. | q.s. | q.s. | q.s. | q.s. |

TABLE 2E

Propylene glycol fatty acid ester-comprising compositions

| Ingredient | | Composition 2E (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Pregn-4-ene-3,20-dione | | 1-10 | 1-8 | 1-5 | 1-5 | 1-5 | 1-5 | 1-5 | 1-5 | 1-5 | 1-5 | 1-5 | 1-5 | 1-5 | 1-5 |
| Propylene glycol fatty acid ester (e.g., Lauroglycol 90, Captex 100, Capmu PG-8, Capmul PG-12, Capryol 90, Acconon E, and so on) | | 30-59 | 2-59 | 30-59 | 30-59 | 30-59 | 30-59 | 30-59 | 30-59 | 30-59 | 30-59 | 30-59 | 30-59 | 30-59 | 30-59 |
| Lipophilic additives | Vitamin E or its derivative (e.g., TPGS, tocopherol acetate, tocotrienol, and so on) | 31-60 | 20-40 | | | | | | 11-40 | | | 11-40 | | | 11-40 |
| | Glyceryl fatty acid ester (e.g., Capmul MCM C8, Capmul 808G, Imwitor 988, Maisine CC, and so on) | | 11-48 | 31-60 | 20-40 | | | | | 11-40 | | | | | |
| | Polyglycerol fatty acid ester (e.g., Caprol PGE-860, Plurol Oleique CC 497, Caprol 3GO, Caprol 10G10O, Caprol ET, and so on) | | | | | 31-60 | 20-40 | | | | | 11-40 | | | |
| | Triglyceride (e.g., Captex 300, Captex 300 Low C6, Captex 350, Miglyol 810, Miglyol 812, and so on) | | | | | | 11-40 | 31-60 | 20-40 | 20-40 | | | | | |
| | Fatty acid or its salt (e.g., oleic acid, linoleic acid, lauric acid, octanoic acid, sodium caprate, sodium laurate, and so on) | | | | 11-40 | | | | | | 31-60 | 20-40 | 20-40 | | |
| | Edible oil (e.g., borage oil, peppermint oil, olive oil, coconut oil, omega-3 oil, and so on) | | | | | | | | | | | | | 31-60 | 20-40 |
| Other carrier ingredients | | q.s. | q.s. | q.s. | q.s. | q.s. | q.s. | q.s. | q.s. | q.s. | q.s. | q.s. | q.s. | q.s. | q.s |

TABLE 2F

PEG glyceride of fatty acid ester-comprising compositions

| Ingredient | | Composition 2F (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Pregn-4-ene-3,20-dione | | 1-10 | 1-8 | 1-5 | 1-5 | 1-5 | 1-5 | 1-5 | 1-5 | 1-5 | 1-5 | 1-5 | 1-5 | 1-5 | 1-5 |
| PEG glyceride of fatty acid ester (e.g., Gelucire 44/14, Gelucire 50/13, Acconon CC-6, Labrafil M1944CS, Labrasol, and so on) | | 30-49 | 30-49 | 3-20 | 30-49 | 30-49 | 30-49 | 30-49 | 30-49 | 30-49 | 30-49 | 30-49 | 30-49 | 30-49 | 30-49 |
| Lipophilic additives | Vitamin E or its derivative (e.g., TPGS, tocopherol acetate, tocotrienol, and so on) | 41-69 | 20-40 | | | 21-40 | | 21-40 | | | | | | | 21-40 |
| | Glyceryl fatty acid ester (e.g., Capmul MCM C8, Capmul 808G, Imwitor 988, Maisine CC, and so on) | | | 41-69 | 20-40 | | | | | | | | 21-40 | | |
| | Polyglycerol fatty acid ester (e.g., Caprol PGE-860, Plurol Oleique CC 497, Caprol 3GO, Caprol 10G10O, Caprol ET, and so on) | | | | | | 41-69 | 20-40 | | | | | | | |
| | Triglyceride (e.g., Captex 300, Captex 300 Low C6, Captex 350, Miglyol 810, Miglyol 812, and so on) | | | | 21-40 | | | | 41-69 | 20-40 | | | | | |
| | Propylene glycol fatty acid ester (e.g., Lauroglycol 90, Captex 100, Capmul PG-8, Capmul PG-12, Capryol 90, Acconon E, and so on) | | | | | | | | | | 41-69 | 20-40 | | | |

TABLE 2F-continued

PEG glyceride of fatty acid ester-comprising compositions

| Ingredient | | Composition 2F (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| | Fatty acid or its salt (e.g., oleic acid, linoleic acid, lauric acid, octanoic acid, sodium caprate, sodium laurate, and so on) | | 21-40 | | | | | | | | | | 41-69 | 20-40 | |
| | Edible oil (e.g., borage oil, peppermint oil, olive oil, coconut oil, omega-3 oil, and so on) | | | | | | | | | | 21-40 | | | | 41-69 | 20-40 |
| Other carrier ingredients | | q.s. | q.s. | q.s. | q.s. | q.s. | q.s. | q.s. | q.s. | q.s. | q.s. | q.s. | q.s. | q.s. | q.s |

TABLE 2G

Fatty acid or its salt-comprising compositions

| Ingredient | | Composition 2G (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Pregn-4-ene-3,20-dione | | 1-10 | 1-8 | 1-8 | 1-6 | 1-6 | 1-6 | 1-6 | 1-6 | 1-6 | 1-6 | 1-6 | 1-6 | 1-6 | 1-6 |
| Fatty acid or its salt (e.g., oleic acid, linoleic acid, lauric acid, octanoic acid, sodium caprate, sodium laurate, and so on) | | 30-59 | 30-59 | 30-59 | 30-59 | 30-59 | 30-59 | 30-59 | 30-59 | 30-59 | 30-59 | 30-59 | 30-59 | 30-59 | 30-59 |
| Lipophilic additives | Vitamin E or its derivative (e.g., TPGS, tocopherol acetate, tocotrienol, and so on) | 31-60 | 20-40 | 20-40 | | | | 11-40 | | | | | | | 11-40 |
| | Glyceryl fatty acid ester (e.g., Capmul MCM C8, Capmul 808G, Imwitor 988, Maisine CC, and so on) | | 11-40 | | 31-60 | 20-40 | | | | | | | | | |
| | Polyglycerol fatty acid ester (e.g., Caprol PGE-860, Plurol Oleique CC 497, Caprol 3GO, Caprol 10G10O, Caprol ET, and so on) | | | | | | 31-60 | 20-40 | | | | | | 11-40 | |
| | Triglyceride (e.g., Captex 300, Captex 300 Low C6, Captex 350, Miglyol 810, Miglyol 812, and so on) | | | | | | | | 31-60 | 20-40 | | | | | |
| | Propylene glycol fatty acid ester (e.g., Lauroglycol 90, Captex 100, Capmul PG-8, Capmul PG-12, Capryol 90, Acconon E, and so on) | | 11-40 | | 11-40 | | | | | | 11-40 | 31-60 | 20-40 | | |
| | Edible oil (e.g., borage oil, peppermint oil, olive oil, coconut oil, omega-3 oil, and so on) | | | | | | | | | | | 11-40 | 31-60 | 20-40 | 20-40 |
| Other carrier ingredients | | q.s. | q.s. | q.s. | q.s. | q.s. | q.s. | q.s. | q.s. | q.s. | q.s. | q.s. | q.s. | q.s. | q.s |

TABLE 2H

Edible oil-comprising compositions

| Ingredient | | Composition 2H (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Pregn-4-ene-3,20-dione | | 1-10 | 1-8 | 1-6 | 1-5 | 1-5 | 1-5 | 1-5 | 1-5 | 1-5 | 1-5 | 1-5 | 1-5 | 1-5 | 1-5 |
| Edible oil (e.g., borage oil, peppermint oil, olive oil, coconut oil, castor oil, omega-3 oil, and so on) | | 30-59 | 30-59 | 30-59 | 30-59 | 30-59 | 30-59 | 30-59 | 30-59 | 30-59 | 30-59 | 30-59 | 30-59 | 30-59 | 30-59 |
| Lipophilic additives | Vitamin E or its derivative (e.g., TPGS, tocopherol acetate, tocotrienol, and so on) | 31-60 | 20-40 | 20-40 | | | | 11-40 | | | | | | | 11-40 |

TABLE 2H-continued

Edible oil-comprising compositions

| Ingredient | | Composition 2H (w/w %) | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| | Glyceryl fatty acid ester (e.g., Capmul MCM C8, Capmul 808G, Imwitor 988, Maisine CC, and so on) | | 11-40 | | 31-60 | 20-40 | | | | | | | | | |
| | Polyglycerol fatty acid ester (e.g., Caprol PGE-860, Plurol Oleique CC 497, Caprol 3GO, Caprol 10G10O, Caprol ET, and so on) | | | | | | 31-60 | 20-40 | | | | 11-40 | | | |
| | Triglyceride (e.g., Captex 300, Captex 300 Low C6, Captex 350, Miglyol 810, Miglyol 812, and so on) | | | | | | | | 31-60 | 20-40 | | | | | |
| | Propylene glycol fatty acid ester (e.g., Lauroglycol 90, Captex 100, Capmul PG-8, Capmul PG-12, Capryol 90, Acconon E, and so on) | | | 11-40 | | 11-40 | | | | | 11-40 | 31-60 | 20-40 | | 11-40 | |
| | Fatty acid or its salt (e.g., oleic acid, linoleic acid, lauric acid, octanoic acid, sodium caprate, sodium laurate, and so on) | | | | | | | | | | | | | 31-60 | 20-40 | 20-40 |
| Other carrier ingredients | | q.s. | q.s. | q.s. | q.s. | q.s. | q.s. | q.s. | q.s. | q.s. | q.s. | q.s. | q.s. | q.s. | q.s. |

Example 3—Pregn-4-ene-3, 20-dione Compositions with Hydrophilic Additives

TABLE 3A

Vitamin E or its derivative-comprising compositions

| Ingredient | | Composition 3A (w/w %) | | | | | | | | |
|---|---|---|---|---|---|---|---|---|---|---|
| | | 1 | 2 | 3 | 4 | 5 | 6 | 7 | 8 | 9 |
| Pregn-4-ene-3,20-dione | | 1-25 | 1-15 | 1-15 | 1-19 | 1-15 | 1-15 | 1-19 | 1-15 | 1-19 |
| Vitamin E or its derivatives (e.g., TPGS, tocopherol, tocopherol acetate, and so on) | | 15-35 | 40-70 | 40-70 | 40-70 | 40-70 | 40-70 | 40-70 | 40-70 | 40-70 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 5-25 | 5-25 | 5-25 | | | | | | |
| | PEG glyceride of fatty acid esters (e.g., Gelucire 44/14, Gelucire 50/13, Acconon CC-6, Labrafil M1944CS, Labrasol, and so on) | | 5-25 | | 20-50 | 5-25 | 5-25 | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | 5-25 | | | 5-25 | 20-50 | 5-25 | |
| | Polysorbates (e.g., Tween 20, Tween 40, Tween 80, and so on) | | | | | 5-25 | | 5-25 | 20-50 | |
| Other carrier ingredients | | q.s. | q.s. | q.s. | q.s. | q.s. | q.s. | q.s. | q.s. | q.s. |

TABLE 3B

Glyceryl fatty acid ester-comprising compositions

| Ingredient | Composition 3B (w/w %) | | | | | | | | | |
|---|---|---|---|---|---|---|---|---|---|---|
| | 1 | 2 | 3 | 4 | 5 | 6 | 7 | 8 | 9 | 10 |
| Pregn-4-ene-3,20-dione | 1-10 | 4-8 | 4-8 | 4-8 | 5-9 | 4-8 | 5-9 | 4-8 | 5-9 | 4-8 |
| Glyceryl fatty acid esters (e.g., Capmul MCM C8, Capmul MCM, Capmul 808G, Imwitor 988, Maisine CC, and so on) | 40-70 | 40-70 | 40-70 | 40-70 | 40-70 | 40-70 | 40-85 | 40-70 | 40-70 | 40-70 |

TABLE 3B-continued

Glyceryl fatty acid ester-comprising compositions

| Ingredient | | Composition 3B (w/w %) | | | | | | | | | |
|---|---|---|---|---|---|---|---|---|---|---|---|
| | | 1 | 2 | 3 | 4 | 5 | 6 | 7 | 8 | 9 | 10 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | 5-25 | 3-25 | | | 5-25 |
| | PEG glyceride of fatty acid esters (e.g., Gelucire 44/14, Gelucire 50/13, Acconon CC-6, Labrafil M1944CS, Labrasol, and so on) | | 5-25 | 2-25 | 5-25 | | | | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | 20-50 | 5-25 | | | | |
| | Polysorbates (e.g., Tween 20, Tween 40, Tween 80, and so on) | | | | | | | 3-25 | 5-25 | | |
| | Vitamin E esters (e.g., TPGS, tocopherol acetate, and so on) | | | | 5-25 | | | | 5-25 | 20-50 | 5-25 |
| Other carrier ingredients | | q.s. | q.s. | q.s. | q.s. | q.s. | q.s. | q.s. | q.s. | q.s. | q.s. |

TABLE 3C

Polyglycerol fatty acid ester-comprising compositions

| Ingredient | | Composition 3C (w/w %) | | | | | | | | | |
|---|---|---|---|---|---|---|---|---|---|---|---|
| | | 1 | 2 | 3 | 4 | 5 | 6 | 7 | 8 | 9 | 10 |
| Pregn-4-ene-3,20-dione | | 1-5 | 1-5 | 1-5 | 1-5 | 1-5 | 1-5 | 1-5 | 1-5 | 1-5 | 1-5 |
| Polyglycerol fatty acid esters (e.g., Caprol PGE 860, Plurol Oleique CC 497, Caprol 3GO, Caprol 10G10O, Caprol ET, and so on) | | 40-70 | 40-70 | 40-70 | 40-70 | 40-70 | 40-70 | 40-70 | 40-70 | 40-70 | 40-70 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | 5-25 | | | | 5-25 |
| | PEG glyceride of fatty acid esters (e.g., Gelucire 44/14, Gelucire 50/13, Acconon CC-6, Labrafil M1944CS, Labrasol, and so on) | | 5-25 | 20-50 | 5-25 | | | | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | 20-50 | 5-25 | | | | |
| | Polysorbates (e.g., Tween 20, Tween 40, Tween 80, and so on) | | | | | | | 20-50 | 5-25 | | |
| | Vitamin E esters (e.g., TPGS, tocopherol acetate, and so on) | | | | 5-25 | | | | 5-25 | 20-50 | 5-25 |
| Other carrier ingredients | | q.s. | q.s. | q.s. | q.s. | q.s. | q.s. | q.s. | q.s. | q.s. | |

TABLE 3D

Triglyceride-comprising compositions

| Ingredient | Composition 3D (w/w %) | | | | | | | | | |
|---|---|---|---|---|---|---|---|---|---|---|
| | 1 | 2 | 3 | 4 | 5 | 6 | 7 | 8 | 9 | 10 |
| Pregn-4-ene-3,20-dione | 1-5 | 1-5 | 1-5 | 1-5 | 1-5 | 1-5 | 1-5 | 1-5 | 1-5 | 1-5 |
| Triglycerides (e.g., Captex 300, Captex 300 Low C6, Captex 350, Miglyol 810, Miglyol 812, and so on) | 40-70 | 40-70 | 40-70 | 40-70 | 40-70 | 40-70 | 40-70 | 40-70 | 40-70 | 40-70 |

TABLE 3D-continued

Triglyceride-comprising compositions

| Ingredient | | Composition 3D (w/w %) | | | | | | | | | |
|---|---|---|---|---|---|---|---|---|---|---|---|
| | | 1 | 2 | 3 | 4 | 5 | 6 | 7 | 8 | 9 | 10 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | | | | | 5-25 |
| | PEG glyceride of fatty acid esters (e.g., Gelucire 44/14, Gelucire 50/13, Acconon CC-6, Labrafil M1944CS, Labrasol, and so on) | | 5-25 | 20-50 | 5-25 | | | | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | 20-50 | 5-25 | | | | |
| | Polysorbates (e.g., Tween 20, Tween 40, Tween 80, and so on) | | | | | | | | 20-50 | 5-25 | |
| | Vitamin E esters (e.g., TPGS, tocopherol acetate, and so on) | | | | 5-25 | | 5-25 | | 5-25 | 20-50 | 5-25 |
| Other carrier ingredients | | q.s. | q.s. | q.s. | q.s. | q.s. | q.s. | q.s. | q.s. | q.s. | q.s. |

TABLE 3E

Propylene glycol fatty acid ester-comprising compositions

| Ingredient | | Composition 3E (w/w %) | | | | | | | | | |
|---|---|---|---|---|---|---|---|---|---|---|---|
| | | 1 | 2 | 3 | 4 | 5 | 6 | 7 | 8 | 9 | 10 |
| Pregn-4-ene-3,20-dione | | 1-5 | 1-5 | 1-5 | 1-5 | 1-5 | 1-5 | 1-5 | 1-5 | 1-5 | 1-5 |
| Propylene glycol fatty acid esters (e.g., Lauroglycol 90, Captex 100, Capmul PG-8, Capmul PG-12, Capryol 90, Acconon E, and so on) | | 40-70 | 40-70 | 40-70 | 40-70 | 40-70 | 40-70 | 40-70 | 40-70 | 40-70 | 40-70 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | | | | | 5-25 |
| | PEG glyceride of fatty acid esters (e.g., Gelucire 44/14, Gelucire 50/13, Acconon CC-6, Labrafil M1944CS, Labrasol, and so on) | | 5-25 | 20-50 | 5-25 | | | | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | 20-50 | 5-25 | | | | |
| | Polysorbates (e.g., Tween 20, Tween 40, Tween 80, and so on) | | | | | | | | 20-50 | 5-25 | |
| | Vitamin E esters (e.g., TPGS, tocopherol acetate, and so on) | | | | 5-25 | | 5-25 | | 5-25 | 20-50 | 5-25 |
| Other carrier ingredients | | q.s. | q.s. | q.s. | q.s. | q.s. | q.s. | q.s. | q.s. | q.s. | q.s. |

TABLE 3F

PEG glyceride of fatty acid ester-comprising compositions

| Ingredient | Composition 3F (w/w %) | | | | | | | | | |
|---|---|---|---|---|---|---|---|---|---|---|
| | 1 | 2 | 3 | 4 | 5 | 6 | 7 | 8 | 9 | 10 |
| Pregn-4-ene-3,20-dione | 1-5 | 1-5 | 1-5 | 1-5 | 1-5 | 1-5 | 1-5 | 1-5 | 1-5 | 1-5 |
| PEG glyceride of fatty acid esters (e.g., Gelucire 44/14 Gelucire 50/13, Acconon CC-6, Labrafil M1944CS, Labrasol, and so on) | 40-70 | 40-70 | 40-70 | 40-70 | 40-70 | 40-70 | 40-70 | 40-70 | 40-70 | 40-70 |

TABLE 3F-continued

PEG glyceride of fatty acid ester-comprising compositions

| Ingredient | | Composition 3F (w/w %) | | | | | | | | | |
|---|---|---|---|---|---|---|---|---|---|---|---|
| | | 1 | 2 | 3 | 4 | 5 | 6 | 7 | 8 | 9 | 10 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | 5-25 | | | | 5-25 | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | 5-25 | | 20-50 | 5-25 | | | | | 5-25 |
| | Polysorbates (e.g., Tween 20, Tween 40, Tween 80, and so on) | | | | | 5-25 | 20-50 | 5-25 | 5-25 | | |
| | Vitamin E esters (e.g., TPGS, tocopherol acetate, and so on) | | | 5-25 | | | | | 5-25 | 20-50 | 5-25 |
| Other carrier ingredients | | q.s. | q.s. | q.s. | q.s. | q.s. | q.s. | q.s. | q.s. | q.s. | q.s. |

TABLE 3G

Fatty acid or its salt-comprising compositions

| Ingredient | | Composition 3G (w/w %) | | | | | | | | | |
|---|---|---|---|---|---|---|---|---|---|---|---|
| | | 1 | 2 | 3 | 4 | 5 | 6 | 7 | 8 | 9 | 10 |
| Pregn-4-ene-3,20-dione | | 1-5 | 1-5 | 1-5 | 1-5 | 1-5 | 1-5 | 1-5 | 1-5 | 1-5 | 1-5 |
| Fatty acid or its salts (e.g., oleic acid, linoleic acid, lauric acid, octanoic acid, sodium caprate, sodium laurate, and so on) | | 40-70 | 40-70 | 40-70 | 40-70 | 40-70 | 40-70 | 40-70 | 40-70 | 40-70 | 40-70 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | 5-25 | | 5-25 | | 5-25 |
| | PEG glyceride of fatty acid esters (e.g., Gelucire 44/14, Gelucire 50/13, Acconon CC-6, Labrafil M1944CS, Labrasol, and so on) | | | 5-25 | 20-50 | 5-25 | | | | | |
| | Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | | 20-50 | 5-25 | | | |
| | Polysorbates (e.g., Tween 20, Tween 40, Tween 80, and so on) | | | | | | | | 20-50 | 5-25 | |
| | Vitamin E esters (e.g., TPGS, tocopherol acetate, and so on) | | | | | 5-25 | | | | 20-50 | 5-25 |
| Other carrier ingredients | | q.s. | q.s. | q.s. | q.s. | q.s. | q.s. | q.s. | q.s. | q.s. | q.s. |

TABLE 3H

Edible oil-comprising compositions

| Ingredient | | Composition 3H (w/w %) | | | | | | | | | |
|---|---|---|---|---|---|---|---|---|---|---|---|
| | | 1 | 2 | 3 | 4 | 5 | 6 | 7 | 8 | 9 | 10 |
| Pregn-4-ene-3,20-dione | | 1-4 | 1-4 | 1-4 | 1-4 | 1-4 | 1-4 | 1-4 | 1-4 | 1-4 | 1-4 |
| Edible oils (e.g., borage oil, peppermint oil, olive oil, coconut oil, castor oil, omega-3 oil, and so on) | | 40-70 | 40-70 | 40-70 | 40-70 | 40-70 | 40-70 | 40-70 | 40-70 | 40-70 | 40-70 |
| Hydrophilic additives | Polyoxyl vegetable oil or glycerides (e.g., Kolliphor EL, Kolliphor RH40, Etocas 40, Croduret 60, Kolliphor HS 15, Etocas 5, Sterotex, Sterotex HM, Sterotex K, or a combination) | 20-50 | 5-25 | | | | 5-25 | | | | 5-25 |

TABLE 3H-continued

Edible oil-comprising compositions

| Ingredient | Composition 3H (w/w %) | | | | | | | | | |
|---|---|---|---|---|---|---|---|---|---|---|
| | 1 | 2 | 3 | 4 | 5 | 6 | 7 | 8 | 9 | 10 |
| PEG glyceride of fatty acid esters (e.g., Gelucire 44/14, Gelucire 50/13, Acconon CC-6, Labrafil M1944CS, Labrasol, and so on) | | 5-25 | 20-50 | 5-25 | | | | | | |
| Polyglycerol-10 fatty acid esters (e.g., glyceryl-10 mono-caprylate, glyceryl-10 mono-/di-caprylate, glyceryl-10 di-caprylate, glyceryl-10 caprylate/caprate, and so on) | | | | | 20-50 | 5-25 | | | | |
| Polysorbates (e.g., Tween 20, Tween 40, Tween 80, and so on) | | | | | | | | 20-50 | 5-25 | |
| Vitamin E esters (e.g., TPGS, tocopherol acetate, and so on) | | | | 5-25 | | | | 5-25 | 20-50 | 5-25 |
| Other carrier ingredients | q.s. | q.s. | q.s. | q.s. | q.s. | q.s. | q.s. | q.s. | q.s. | q.s. |

Example 4—Pregn-4-ene-3, 20-dione Compositions

TABLE 4A

Specific Examples of Vit-E-comprising Compositions

| Ingredient | | Vit-E-comprising Composition 4A (w/w %) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Pregn-4-ene-3,20-dione | | 10-20 | 20-25 | 1-8 | 1-10 | 1-10 | 1-10 | 1-10 | 1-10 | 1-10 | 1-12 | 1-12 | 1-12 | 1-12 | 1-10 | 1-10 |
| Alpha-Tocopherol | | 80-90 | 20-25 | 2-22 | 20-45 | 10-22 | 4-25 | 10-22 | 10-22 | 10-22 | 10-22 | 10-22 | 10-20 | 10-20 | 10-20 | 10-20 |
| Glyceryl caprylate/caprate (e.g., Capmul MCM, Capmul 708G) | | | | | 40-65 | 20-45 | | | | | | | | | | |
| Glyceryl monocaprylate (e.g., Capmul MCM C8) | | | 30-45 | | | | 30-85 | 20-45 | | | | | | | | |
| Glyceryl monolinoleate (e.g., Maisine) | | | | | | | | | 20-45 | 20-45 | | | | | | |
| Octanoic acid | | | | | | | | | | | 20-45 | 20-45 | | | | |
| Peppermint oil | | | | | | | | | | | | | 20-70 | 20-70 | | |
| Coconut oil | | | | | | | | | | | | | | | 20-70 | 20-70 |
| Lipophilic additives† | Span80 Lauroglycol Labraphil M2125 CS | | 3-6 | 5-25 | | 5-25 | 2-15 | 5-25 | | 5-25 | | 5-25 | | 5-25 | | 5-25 |
| Hydrophilic additives† | TPGS Caprol PGE-860 Labrasol Tween80 Kolliphor EL Kolliphor RH40 | | 10-30 | 25-50 | 5-30 | 5-25 | 5-50 | 5-25 | 25-50 | 5-25 | 25-50 | 5-25 | 25-50 | 5-25 | 25-50 | 5-25 |
| Other carrier ingredients | | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | No | Yes | No | No | No | No | No | No | No | No | No | No | No | No | No |

†Lipophilic or hydrophilic additives can be selected at least one or a combination of the ingredients shown in the table. Hereafter it applies to all examples.

TABLE 4B

Specific examples of fatty acid or its salt-comprising Compositions

| Ingredient | Fatty acid or its salt-comprising Composition 4B (w/w %) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Pregn-4-ene-3,20-dione | 10-15 | 1-8 | 1-8 | 1-12 | 1-12 | 1-10 | 1-10 | 1-10 | 1-10 | 1-10 | 1-10 | 1-10 | 1-10 | 1-10 | 1-10 |
| Octanoic acid | 85-90 | 30-50 | 30-50 | 30-50 | 30-50 | 30-50 | 30-50 | 30-50 | 30-50 | 30-50 | 30-50 | 30-50 | 30-50 | 30-50 | 30-50 |
| Alpha-Tocopherol | | | | 10-22 | 10-22 | | | | | | | | | | |

TABLE 4B-continued

Specific examples of fatty acid or its salt-comprising Compositions

Fatty acid or its salt-comprising Composition 4B (w/w %)

| Ingredient | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Glyceryl caprylate/caprate (e.g., Capmul MCM, Capmul 708G) | | | | | | | 10-30 | 20-30 | | | | | | | | |
| Glyceryl monocaprylate (e.g., Capmul MCM C8) | | | | | | | | | 10-30 | 20-30 | | | | | | |
| Glyceryl monolinoleate (e.g., Maisine) | | | | | | | | | | | 10-30 | 20-30 | | | | |
| Peppermint oil | | | | | | | | | | | | | 10-30 | 20-30 | | |
| Coconut oil | | | | | | | | | | | | | | | 10-30 | 20-30 |
| Lipophilic additives | Span80 | | | 5-25 | | 5-25 | | 5-25 | | 5-25 | | 5-25 | | 5-25 | | 5-25 |
| | Lauroglycol | | | | | | | | | | | | | | | |
| | Labraphil M2125 CS | | | | | | | | | | | | | | | |
| Hydrophilic additives | TPGS | | 25-50 | 5-25 | 25-50 | 5-25 | 25-50 | 5-25 | 25-50 | 5-25 | 25-50 | 5-25 | 25-50 | 5-25 | 25-50 | 5-25 |
| | Caprol PGE-860 | | | | | | | | | | | | | | | |
| | Labrasol | | | | | | | | | | | | | | | |
| | Tween80 | | | | | | | | | | | | | | | |
| | Kolliphor EL | | | | | | | | | | | | | | | |
| | Kolliphor RH40 | | | | | | | | | | | | | | | |
| Other carrier Ingredients | | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | Yes | No | No | No | No | No | No | No | No | No | No | No | No | No | No |

TABLE 4C

Specific examples of glyceryl fatty acid ester-comprising Compositions

Glyceryl fatty acid ester-comprising Composition 4C (w/w %)

| Ingredient | | 1 | 2 | 3 | 4 | 5 | 6 | 7 | 8 | 9 | 10 | 11 | 12 |
|---|---|---|---|---|---|---|---|---|---|---|---|---|---|
| Pregn-4-ene-3,20-dione | | 5-10 | 5-10 | 5-10 | 1-10 | 1-10 | 1-10 | 1-10 | 1-6 | 1-6 | 1-6 | 1-6 | 1-6 |
| Glyceryl caprylate/caprate (e.g., Capmul MCM, Capmul 708G) | | 50-85 | | 50-70 | | | | 30-50 | | | 30-50 | 30-50 | |
| Glyceryl monocaprylate (e.g., Capmul MCM C8) | | | 90-95 | | 40-70 | 40-70 | 30-50 | | 30-50 | 30-50 | | | 30-50 |
| Alpha-Tocopherol | | | | | 10-22 | 10-22 | 10-22 | 10-22 | | | | | |
| Octanoic acid | | | | | | | | | | | 20-30 | 20-30 | |
| Glyceryl monolinoleate (e.g., Maisine) | | | | | | | | | 20-30 | | | | |
| Peppermint oil | | | | | | | | | | | | | 20-35 |
| Coconut oil | | | | | | | | | | | | 20-35 | |
| Lipophilic additives | Span80 | | | 1-10 | | 5-25 | 5-25 | 5-25 | | | 5-25 | 5-25 | |
| | Lauroglycol | | | | | | | | | | | | |
| | Labraphil M2125 CS | | | | | | | | | | | | |
| Hydrophilic additives | TPGS | 5-15 | 20-50 | 0-10 | 5-25 | 5-25 | 5-25 | 5-25 | 25-50 | 25-50 | 5-25 | 5-25 | 25-50 |
| | Caprol PGE-860 | | | | | | | | | | | | |
| | Labrasol | | | | | | | | | | | | |
| | Tween80 | | | | | | | | | | | | |
| | Kolliphor EL | | | | | | | | | | | | |
| | Kolliphor RH40 | | | | | | | | | | | | |
| Other carrier ingredients | | q.s. | q.s. | q.s. | q.s. | q.s. | q.s. | q.s. | q.s. | q.s. | q.s. | q.s. | q.s. |
| Crystalline form of Pregn-4-ene-3,20-dione | | Yes | No | Yes | No | No | No | Yes | No | No | No | Yes | No |

TABLE 4D

Specific examples of PEG glyceride of fatty acid ester-comprising Compositions

PEG glyceride of fatty acid ester comprising Compositon 4D (w/w %)

| Ingredient | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Pregn-4-ene-3,20-dione | | 1-5 | 1-5 | 1-5 | 1-6 | 1-6 | 1-8 | 1-8 | 1-5 | 1-5 | 1-5 | 1-5 | 1-5 | 1-5 | 1-5 | 1-5 |
| PEG-6 mono/di-linoleate (e.g., Labraphil M2125 CS) | | 95-99 | 50-70 | 40-70 | 30-50 | 30-50 | 30-50 | 30-50 | 30-50 | 30-50 | 30-50 | 30-50 | 30-50 | 30-50 | 30-50 | 30-50 |
| Octanoic acid | | | | | 25-40 | 10-25 | | | | | | | | | | |
| Alpha-Tocopherol | | | | | | | 10-22 | 10-22 | | | | | | | | |
| Glyceryl caprylate/caprate (e.g., Capmul MCM, Capmul 708G) | | | | | | | | | 20-30 | | | | | | | |
| Glyceryl monocaprylate (e.g., Capmul MCM C8) | | | | | | | | | | 20-30 | | | | | | |
| Glyceryl monolinoleate (e.g., Maisine) | | | | | | | | | | | 20-30 | 20-30 | | | | |
| Peppermint oil | | | | | | | | | | | | | | 20-30 | 20-30 | |
| Coconut oil | | | | | | | | | | | | | | | 20-30 | 20-30 |
| Lipophilic additives | Span80 | | | 5-25 | | 5-25 | | 5-25 | | 5-25 | | 5-25 | | 5-25 | | 5-25 |
| | Lauroglycol | | | | | | | | | | | | | | | |
| Hydrophilic additives | TPGS | | 20-50 | 5-25 | 25-50 | 5-25 | 25-50 | 5-25 | 25-50 | 5-25 | 25-50 | 5-25 | 25-50 | 5-25 | 25-50 | 5-25 |
| | Caprol PGE-860 | | | | | | | | | | | | | | | |
| | Labrasol | | | | | | | | | | | | | | | |
| | Tween80 | | | | | | | | | | | | | | | |
| | Kolliphor EL | | | | | | | | | | | | | | | |
| | Kolliphor RH40 | | | | | | | | | | | | | | | |
| Other carrier Ingredients | | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | Yes | Yes | Yes | No | No | No | No | Yes | No | Yes | Yes | No | No | Yes | Yes |

TABLE 4E

Specific examples of polyglycerol fatty acid ester-comprising Compositions

Polyglycerol fatty acid ester-comprising Composition 4E (w/w %)

| Ingredient | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Pregn-4-ene-3,20-dione | | 1-4 | 1-4 | 1-4 | 1-6 | 1-6 | 1-6 | 1-6 | 1-5 | 1-5 | 1-5 | 1-5 | 1-5 | 1-5 | 1-5 | 1-5 |
| Polyglyceryl-10 mono/di-oleate (e.g., Caprol PGE-860) | | 95-99 | 50-70 | 40-70 | 30-50 | 30-50 | 30-50 | 30-50 | 30-50 | 30-50 | 30-50 | 30-50 | 30-50 | 30-50 | 30-50 | 30-50 |
| Octanoic acid | | | | | 25-40 | 10-25 | | | | | | | | | | |
| Alpha-Tocopherol | | | | | | | 10-22 | 10-22 | | | | | | | | |
| Glyceryl caprylate/caprate (e.g., Capmul MCM, Capmul 708G) | | | | | | | | | 20-30 | | | | | | | |
| Glyceryl monocaprylate (e.g., Capmul MCM C8) | | | | | | | | | | 20-30 | | | | | | |
| Glyceryl monolinoleate (e.g., Maisine) | | | | | | | | | | | 20-30 | 20-30 | | | | |
| Peppermint oil | | | | | | | | | | | | | | 20-30 | 20-30 | |
| Coconut oil | | | | | | | | | | | | | | | 20-30 | 20-30 |
| Lipophilic additives | Span80 | | | 5-25 | | 5-25 | | 5-25 | | 5-25 | | 5-25 | | 5-25 | | 5-25 |
| | Lauroglycol | | | | | | | | | | | | | | | |
| | Labraphil M2125 CS | | | | | | | | | | | | | | | |
| Hydrophilic additives | TPGS | | 20-50 | 5-25 | 25-50 | 5-25 | 25-50 | 5-25 | 25-50 | 5-25 | 25-50 | 5-25 | 25-50 | 5-25 | 20-50 | 25-50 |
| | Labrasol | | | | | | | | | | | | | | | |
| | Tween80 | | | | | | | | | | | | | | | |
| | Kolliphor EL | | | | | | | | | | | | | | | |
| | Kolliphor RH40 | | | | | | | | | | | | | | | |
| Other carrier Ingredients | | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | Yes | Yes | Yes | No | No | No | No | Yes | Yes | Yes | Yes | No | No | Yes | Yes |

TABLE 4F

Specific examples of triglyceride-comprising Compositions

Polyglycerol fatty acid ester-comprising Composition 4F (w/w %)

| Ingredient | | 1 | 2 | 3 | 4 | 5 | 6 | 7 | 8 | 9 | 12 | 13 | 14 | 15 | 16 | 17 |
|---|---|---|---|---|---|---|---|---|---|---|---|---|---|---|---|---|
| Pregn-4-ene-3,20-dione | | 1-4 | 1-4 | 1-4 | 1-6 | 1-6 | 1-6 | 1-6 | 1-5 | 1-5 | 1-5 | 1-5 | 1-5 | 1-5 | 1-5 | 1-5 |
| Caprylic/Capric triglyceride (e.g., Captex 300) | | 95-99 | 50-70 | 40-70 | 30-50 | 30-50 | 30-50 | 30-50 | 30-50 | 30-50 | 30-50 | 30-50 | 30-50 | 30-50 | 30-50 | 30-50 |
| Octanoic acid | | | | | 25-40 | 10-25 | | | | | | | | | | |
| Alpha-Tocopherol | | | | | | | 10-22 | 10-22 | | | | | | | | |
| Glyceryl caprylate/caprate (e.g., Capmul MCM, Capmul 708G) | | | | | | | | | 20-30 | | | | | | | |
| Glyceryl monocaprylate (e.g., Capmul MCM C8) | | | | | | | | | | 20-30 | | | | | | |
| Glyceryl monolinoleate (e.g., Maisine) | | | | | | | | | | | 20-30 | 20-30 | | | | |
| Peppermint oil | | | | | | | | | | | | | | 20-30 | 20-30 | |
| Coconut oil | | | | | | | | | | | | | | | | 20-30 | 20-30 |
| Lipophilic additives | Span80 Lauroglycol Labraphil M2125 CS | | | 5-25 | | 5-25 | | 5-25 | | 5-25 | | 5-25 | | 5-25 | | 5-25 |
| Hydrophilic additives | TPGS Caprol PGE-860 Labrasol Tween80 Kolliphor EL Kolliphor RH40 | | 20-50 | 5-25 | 25-50 | 5-25 | 25-50 | 5-25 | 25-50 | 5-25 | 25-50 | 5-25 | 25-50 | 5-25 | 25-50 | 5-25 |
| Other carrier ingredients | | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | Yes | Yes | Yes | No | No | No | No | Yes | Yes | Yes | Yes | No | No | Yes | Yes |

TABLE 4G

Specific Examples of propylene glycol fatty acid ester-comprising Compositions

Polyglycerol fatty acid ester-comprising Composition 4G (w/w %)

| Ingredient | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Pregn-4-ene-3,20-dione | | 5-10 | 1-8 | 1-8 | 1-10 | 1-10 | 1-10 | 1-10 | 1-8 | 1-8 | 1-8 | 1-8 | 1-8 | 1-8 | 1-8 | 1-8 |
| Propylene glycol monocaprylate (e.g., Capmul PG-8) | | 90-95 | 50-70 | 40-70 | 30-50 | 30-50 | 30-50 | 30-50 | 30-50 | 30-50 | 30-50 | 30-50 | 30-50 | 30-50 | 30-50 | 30-50 |
| Octanoic acid | | | | | 25-40 | 10-25 | | | | | | | | | | |
| Alpha-Tocopherol | | | | | | | 10-22 | 10-22 | | | | | | | | |
| Glyceryl caprylate/caprate (e.g., Capmul MCM, Capmul 708G) | | | | | | | | | 20-30 | | | | | | | |
| Glyceryl monocaprylate (e.g., Capmul MCM C8) | | | | | | | | | | 20-30 | | | | | | |
| Glyceryl monolinoleate (e.g., Maisine) | | | | | | | | | | | 20-30 | 20-30 | | | | |
| Peppermint oil | | | | | | | | | | | | | | 20-30 | 20-30 | |
| Coconut oil | | | | | | | | | | | | | | | | 20-30 | 20-30 |
| Lipophilic additives | Span80 Lauroglycol Labraphil M2125 CS | | | 5-25 | | 5-25 | | 5-25 | | 5-25 | | 5-25 | | 5-25 | | 5-25 |
| Hydrophilic additives | TPGS Caprol PGE-860 Labrasol Tween80 Kolliphor EL Kolliphor RH40 | | 20-50 | 5-25 | 25-50 | 5-25 | 25-50 | 5-25 | 25-50 | 5-25 | 25-50 | 5-25 | 25-50 | 5-25 | 25-50 | 5-25 |

TABLE 4G-continued

Specific Examples of propylene glycol fatty acid ester-comprising Compositions

| Ingredient | Polyglycerol fatty acid ester-comprising Composition 4G (w/w %) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Other carrier Ingredients | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | No | No | Yes | No | No | No | No | No | No | No | Yes | No | No | No | Yes |

TABLE 4H

Specific Examples of edible oil-comprising Compositions

| Ingredient | | Edible oil-comprising Composition 4H (w/w %) | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| Pregn-4-ene-3,20-dione | | 5-10 | 1-8 | 1-8 | 1-10 | 1-10 | 1-10 | 1-10 | 3-6 | 1-6 | 1-6 | 1-8 | 1-6 | 1-6 | 1-6 | 1-6 | 1-6 |
| Peppermint oil | | 90-95 | 40-80 | 30-60 | 20-50 | 20-50 | 20-50 | 20-50 | | | | | | | | | |
| Coconut oil | | | | | | | | | 94-97 | 40-80 | 30-60 | 20-50 | 20-50 | 20-50 | 20-50 | 20-50 | 20-50 |
| Alpha-Tocopherol | | | | | 10-22 | | | | | | | 10-22 | | | | | |
| Glyceryl caprylate/caprate (e.g., Capmul MCM, Capmul 708G) | | | | | | | | | | | | | 20-40 | | | | |
| Glyceryl monocaprylate (e.g., Capmul MCM C8) | | | | | | 20-40 | | | | | | | | 20-40 | 5-20 | | |
| Glyceryl monolinoleate (e.g., Maisine) | | | | | | | 20-40 | | | | | | | | | 20-40 | |
| Propylene glycol monocaprylate (e.g., Capmul PG-8) | | | | | | | | 20-40 | | | | | | | | | 20-40 |
| Lipophilic additives | Span80 | | | 5-25 | | 5-25 | | 5-25 | | 5-25 | | 5-25 | | 5-25 | | | 5-25 |
| | Labraphil M2125 CS | | | | | | | | | | | | | | | | |
| | Lauroglycol | | | | | | | | | | | | | | | | |
| Hydrophilic additives | TPGS | | 25-50 | 5-25 | 25-50 | 5-25 | 25-50 | 5-25 | | 5-25 | 25-50 | 5-25 | 25-50 | 5-25 | 25-50 | 25-50 | 5-25 |
| | Caprol PGE-860 | | | | | | | | | | | | | | | | |
| | Labrasol | | | | | | | | | | | | | | | | |
| | Tween80 | | | | | | | | | | | | | | | | |
| | Kolliphor EL | | | | | | | | | | | | | | | | |
| | Kolliphor RH40 | | | | | | | | | | | | | | | | |
| Other carrier Ingredients | | q.s. | q.s. | q.s. | q.s. | q.s. | q.s. | q.s. | q.s. | q.s. | q.s. | q.s. | q.s. | q.s. | q.s. | q.s. | q.s. |
| Crystalline form of Pregn-4-ene-3,20-dione | | No | No | Yes | No | No | No | No | No | No | No | No | No | No | No | No | No |

Example 5—Pregn-4-ene-3, 20-dione Compositions

In one aspect, the examples described in the following pharmaceutical composition tables can be formulated with or without at least one or more polymeric release modifiers. In yet another aspect, these examples can be formulated with or without at least one or more 5-alpha-reductase enhancers, wherein the carriers or its components in the formulations herein are surprisingly found to promote conversion of pregn-4-ene-3,20-dione, possibly serving as 5α-reductase enhancers. For example, the carriers comprising alpha-tocopherol, glyceryl monocaprylate, and a combination thereof can increase conversion of pregn-4-ene-3,20-dione to its $GABA_A$ receptor allosteric metabolites (e.g., 3α-OH-5α-pregnan-20-one and/or 3α-OH-5β-pregnan-20-one). 5α-reductase enhancers promote the conversion of pregn-4-ene-3,20-dione into its metabolites (e.g., 3α-OH-5α-pregnan-20-one and/or 3α-OH-5β-pregnan-20-one). These pharmaceutical compositions comprising non crystalline or partially or fully solubilized pregn-4-ene-3,20-dione described herein can provide pharmaceutically effective levels of these $GABA_A$ receptor agonists for treatment of a CNS disorder. These pharmaceutical compositions were prepared using standard techniques commonly used in the pharmaceutical field.

TABLE 5

Oral compositions comprising Non-crystalline forms of pregn-4-ene-3,20-dione

| Component | 5-1 | 5-2 | 5-3 | 5-4 | 5-5 | 5-6 | 5-7 | 5-8 | 5-9 | 5-10 | 5-11 | 5-12 | 5-13 | 5-14 | 5-15* |
|---|---|---|---|---|---|---|---|---|---|---|---|---|---|---|---|
| Pregn-4-ene-3,20-dione | 6-8 | 6-9 | 6-9 | 3-10 | 6-9 | 6-8 | 5-8 | 3-10 | 7-10 | 4-7 | 6-9 | 20-25 | 7-10 | 4-6 | 35-42 |
| Glyceryl monocaprylate (e.g., Capmul MCM C8) | 80-85 | 43-48 | 43-48 | 60-68 | 43-48 | 43-48 | | 43-48 | | | | 30-40 | | | |
| Edible oil (e.g., Peanut oil) | | | | | | | 65-85 | | | | | | | | 45-50 |
| Propylene Glycol monolaurate (e.g., Lauroglycol) | | | | | | | | | 43-48 | 38-43 | | | | | |
| Propylene Glycol Monocaprylate (e.g., Capmul PG-8) | | 2-5 | | | | | | | | | 55-60 | | 13-18 | | |
| Lecithin | | | | | | | | | | | | | | | 0-5 |
| Alpha-tocopherol | 3-5 | 18-22 | 18-22 | 18-22 | 18-22 | 18-22 | | 2-5 | 18-22 | 2-5 | 18-22 | 15-25 | 18-22 | 2-5 | |
| Peppennint oil | | | | | | | | | | | | | 28-35 | 42-50 | |
| TPGS | | | | | 6-10 | | | | | 22-28 | | | 13-18 | 18-22 | |
| Polyethylene glycol castor oil (e.g., Kolliphor EL, Kolliphor RH40) | 4-8 | 22-28 | 22-28 | 4-8 | 13-18 | 13-18 | 3-8 | 42-50 | 28-35 | 22-28 | 13-18 | 10-15 | 7-11 | 22-28 | |
| Sodium lauryl sulfate | | | | | | | 3-8 | | | | | 5-10 | | | |
| Polyglyceryl-10 mono/di-oleate (e.g., Caprol PGE-860) | | | | | | 6-10 | | | | | | | | | |
| Glyceryl distearate | | | | | | | | | | | | 3-6 | | | |
| Additives | q.s. | q.s. | q.s. | q.s. | q.s. | q.s. | q.s. | q.s. | q.s. | q.s. | q.s. | q.s. | q.s. | q.s. | q.s |
| Total | 100 | 100 | 100 | 100 | 100 | 100 | 100 | 100 | 100 | 100 | 100 | 100 | 100 | 100 | 100 |

*An oral composition with a micronized crystalline form of pregn-4-ene-3,20-dione As shown in the above examples, the compositions can provide fully solubilized or non-crystalline forms of pregn-4-ene-3,20-di one. The oral compositions of the present disclosure can be formulated to provide % release rates that can yield enhanced therapeutic effects of the GABA receptor modulating metabolites of Pregn-4-ene-3,20-dione. In one example, the compositions or oral dosage forms (Composition 5-8 and 5-12) were formulated to have a release rate in vitro when measured using a USP Type-I dissolution apparatus in 900 mL of deionized water with 2.0% (w/v) of SLS at 100 rpm at 37'° C. FIG. 2 shows that the present oral compositions or dosage forms (e.g., Composition 5-8 and 5-12) can release at least one of greater than about 5000 of the pregn-4-ene-3,20-dione after 15 minutes, greater than about 75% of the pregn-4-ene-3,20-dione after 30 minutes, greater than about 90% of the pregn-4-ene-3,20-dione after 60 minutes, and greater than 50% of the pregn-4-ene-3,20-dione in 4 hours when measured using a USP Type I dissolution apparatus in 900 mL of deionized water with 2.0% (w/v) of SLS at 100 rpm at 37° C. Surprisingly, it was found that the present oral compositions (e.g., Composition 5-8 and 5-12) can release greater than about 30% more of pregn-4-ene-3,20-dione after 15 minutes as compared to the % release from a micronized administration (e.g., Composition 5-15).

In another example, the compositions or oral dosage forms (Composition 5-4, 5-8, and 5-12) were formulated to have a release rate in vitro when measured using a USP Type-II dissolution apparatus in 900 mL of deionized water with 0.25% (w/v) of SLS at 75 rpm at 37° C. FIG. 3 shows that the present oral compositions or dosage forms (e.g., Composition 5-4, 5-8, and 5-12) can release at least one of greater than about 50% of the pregn-4-ene-3,20-dione after 20 minutes, greater than about 75% of the pregn-4-ene-3, 20-dione after 30 minutes, greater than about 90% of the pregn-4-ene-3,20-dione after 60 minutes, and greater than 50% of the pregn-4-ene-3,20-dione in 4 hours when measured using a USP Type-II dissolution apparatus in 900 mL of deionized water with 0.25% (w/v) of SLS at 75 rpm at 37° C.

Example 6—Pregn-4-ene-3, 20-dione Compositions

TABLE 6

Oral compositions comprising pregn-4-ene-3,20-dione

| Component | 6-1 | 6-2 | 6-3 | 6-4 | 6-5 | 6-6 | 6-7 | 6-8 | 6-9 | 6-10 | 6-11 | 6-12 | 6-13 | 6-14 | 6-15 |
|---|---|---|---|---|---|---|---|---|---|---|---|---|---|---|---|
| Pregn-4-ene-3,20-dione | 7.6 | 7.5 | 7.0 | 9.0 | 7.5 | 7.0 | 6.0 | 4.3 | 8.5 | 5.5 | 6.5 | 23.5 | 8.0 | 5.0 | 40.0 |
| Glyceryl monocaprylate (e.g., Capmul MCM C8) | 82.9 | 45.5 | 46.0 | 63.7 | 46.0 | 46.0 | | 46.0 | | | | 35.0 | | | |
| Edible oil (e.g., Peanut oil) | | | | | | | 84.6 | | | | | | | | 49.6 |
| Propylene Glycol monolaurate (e.g., Lauroglycol) | | 2.0 | | | | | | | 40.0 | 40.0 | | | | | |

TABLE 6-continued

Oral compositions comprising pregn-4-ene-3,20-dione

| Component | 6-1 | 6-2 | 6-3 | 6-4 | 6-5 | 6-6 | 6-7 | 6-8 | 6-9 | 6-10 | 6-11 | 6-12 | 6-13 | 6-14 | 6-15 |
|---|---|---|---|---|---|---|---|---|---|---|---|---|---|---|---|
| Propylene Glycol Monocaprylate (e.g., Capmul PG-8) | | | | | | | | | | | 57.5 | 16.0 | | | |
| Lecithin | | | | | | | | | | | | | | | 0.4 |
| Alpha-tocopherol | 4.6 | 20.0 | 20.5 | 20.5 | 21.0 | 21.0 | | 2.5 | 21.0 | 4.0 | 21.0 | 20.5 | 21.0 | 4.0 | |
| Peppermint oil | | | | | | | | | | | | | 30.0 | 45.0 | |
| TPGS | | | | | 9.0 | | | | | 25.5 | | | 16.0 | 21.0 | |
| Sodium lauryl sulfate | | | | | | | | 4.7 | | | | 6.5 | | | |
| PEG Castor Oil (e.g., Kolliphor EL, Kolliphor RH40) | 4.9 | 25.0 | 26.5 | 6.8 | 16.5 | 17.0 | 4.7 | 47.2 | 30.5 | 25.0 | 15.0 | 10.5 | 9.0 | 25.0 | |
| Polyglyceryl-10 mono/di-oleate (e.g., Caprol PGE-860) | | | | | 9.0 | | | | | | | | | | |
| Glyceryl distearate | | | | | | | | | | | | 4.0 | | | |
| Additives | q.s. | q.s. | q.s. | q.s. | q.s. | q.s. | q.s. | q.s. | q.s. | q.s. | q.s. | q.s. | q.s. | q.s. | q.s. |
| Total | 100 | 100 | 100 | 100 | 100 | 100 | 100 | 100 | 100 | 100 | 100 | 100 | 100 | 100 | 100 |
| % w/w Ratio of Pregn-4-ene-3,20-dione/alpha-tocopherol | 1.7 | 0.4 | 0.4 | 0.4 | 0.4 | 0.3 | N/A | 1.7 | 0.4 | 1.4 | 0.3 | 1.1 | 0.4 | 1.3 | N/A |
| % w/w Ratio of Pregn-4-ene-3,20-dione/glyceryl monocaprylate | 0.1 | 0.2 | 0.2 | 0.1 | 0.2 | 0.2 | N/A | 0.1 | N/A | N/A | N/A | 0.7 | N/A | N/A | N/A |
| % w/w Ratio of alpha-tocopherol/hydrophilic ingredient | 0.9 | 0.8 | 0.8 | 3.0 | 0.8 | 0.8 | N/A | 0.1 | 0.7 | 0.1 | 1.4 | 1.2 | 0.8 | 0.1 | N/A |
| % w/w Ratio of glyceryl monocaprylate/hydrophilic ingredient | 16.9 | 1.8 | 1.8 | 9.4 | 2.8 | 2.7 | N/A | 1.0 | N/A | N/A | N/A | 2.1 | N/A | N/A | N/A |

As shown in the Table 6, the oral compositions or dosage forms can provide a ratio of pregn-4-ene-3,20-dione to alpha-tocopherol from about 0.3 to 2.0, such as about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, and about 2.0.

In one example, the oral compositions or dosage forms can provide a ratio of Pregn-4-ene-3,20-dione to glyceryl monocaprylate less than about 0.7, such as about 0.7, about 0.6, about 0.5, about 0.4, about 0.3, about 0.2, about 0.19, about 0.18, about 0.17, about 0.16, about 0.15, about 0.14, about 0.13, about 0.12, about 0.11, about 0.10, about 0.09, and less than about 0.09.

In another example, the oral compositions or dosage forms can provide a ratio of alpha-tocopherol to a hydrophilic ingredient from about 0.05 to 4.0, such as about 0.05, about 0.1, about 0.3, about 0.5, about 0.7, about 0.9, about 1.1, about 1.3, about 1.4, about 1.7, about 2.0, about 2.3, about 2.6, about 2.9, about 3.2, about 3.5, and about 4.0.

In a further example, the oral compositions or dosage forms can provide a ratio of glyceryl monocaprylate to a hydrophilic ingredient from about 1 to 20 or about 1 to 10, such as about 1, about 2, about 3, about 4, about 5, about 6, about 7, about 8, about 9, and about 10. In another example, the ratio of glyceryl monocaprylate to a hydrophilic ingredient can be from less than about 2.5, such as about 2.4, about 2.3, about 2.2, about 2.1, about 2.0, about 1.9, about 1.8, about 1.7, about 1.6, about 1.5, about 1.4, about 1.3, about 1.2, about 1.1, about 1.0, and less than about 1.0.

Example 7 Pregn-4-ene-3, 20-dione Drink Compositions

TABLE 7A

Drink compositions comprising pregn-4-ene-3,20-dione

| | Composition 7A (w/w %) | | | | |
|---|---|---|---|---|---|
| Component* | I | II | III | IV | V |
| Pregn-4-ene-3,20-dione | 0.067-1 | 0.067-1 | 0.067-1 | 0.067-1 | 0.067-1 |
| Vitamin E or its derivatives (e.g., TPGS, tocopherol, tocopherol acetate, tocotrienol, or a combination) | | | | 0.067-3.33 | 0.067-3.33 |

TABLE 7A-continued

Drink compositions comprising pregn-4-ene-3,20-dione

| | Composition 7A (w/w %) | | | | |
|---|---|---|---|---|---|
| Component* | I | II | III | IV | V |
| Lipophilic additive (e.g., glyceryl monocaprylate, glyceryl mono and dicaprylocaprate, propylene glycol monolaurate, propylene glycol monocaprylate, sorbitan monolaurate, glyceryl monolinoleate, sorbitan monooleate, linoleoyl polyoxyl-6 glycerides, polyglyceryl 3-oleate, oleoyl polyoxyl-6 glyceride, peppermint oil, caprylic acid, oleic acid, castor oil, linoleic acid, and a combination thereof) | 0.33-5.67 | | 0.067-4.67 | 0.067-4.67 | |
| Hydrophilic additive (s) (e.g., PEG-35 castor oil, PEG-40 hydrogenated castor oil, polysorbate 80, polysorbate 20, polyglyceryl-10 monooleate, polyglyceryl-10 dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, lauroyl PEG-32 glyceride, and a combination thereof) | | 0.33-5.67 | 0.33-6.00 | 0.33-6.00 | 0.33-6.00 |
| Purified Water | q.s to 100% | q.s to 100% | q.s to 100% | q.s to 100% | q.s to 100% |

*Components in the drink compositions can comprise other carrier ingredients comprising at least, one of flavoring agents, sweeteners, antimicrobial preservatives, antioxidants, and edible fat.

TABLE 7B

Drink compositions comprising pregn-4-ene-3,20-dione

| | Composition 7B (% w/w) | | | | |
|---|---|---|---|---|---|
| Component* | I | II | III | IV | V |
| Pregn-4-ene-3,20-dione | 0.27 | 0.47 | 0.43 | 0.29 | 0.47 |
| Glyceryl monocaprylate | 2.07 | 3.13 | 3.00 | 3.07 | 3.07 |
| Polyoxyl 40 hydrogenated castor oil | 3.67 | 1.67 | 1.67 | 3.15 | 1.77 |
| Alpha-Tocopherol | 0.67 | 1.33 | 0.93 | 0.17 | 1.37 |
| Propylene glycol Monolaurate | | | 0.63 | | |
| Purified Water | q.s. to 100% | q.s. to 100% | q.s. to 100% | q.s. to 100% | q.s. to 100% |

*Components in the drink compositions can comprise optional carrier ingredients comprising at least, one of flavoring agents, sweeteners, antimicrobial preservatives, antioxidants, and edible fat.

TABLE 7C

Drink compositions comprising pregn-4-ene-3,20-dione

| | Composition 7C (% w/w) | | | |
|---|---|---|---|---|
| Component* | I | II | III | IV |
| Pregn-4-ene-3,20-dione | 0.60 | 0.51 | 0.30 | 0.63 |
| Glyceryl monocaprylate | 4.25 | 5.53 | 4.13 | |
| Polyoxyl 40 hydrogenated castor oil | 0.45 | 0.33 | 2.77 | |
| Alpha-Tocopherol | 1.37 | 0.31 | 0.93 | 1.33 |
| TPGS | | | | 0.50 |
| Propylene glycol Monolaurate | | | 0.90 | |
| Oleoyl polyoxyl-6 glycerides | | | 1.17 | |
| Sorbitan Monooleate | | | 0.60 | |
| Purified Water | q.s. to 100% | q.s. to 100% | q.s. to 100% | q.s. to 100% |

*Components in the drink compositions can comprise optional carrier ingredients comprising at least one of flavoring agents, sweeteners, antimicrobial preservatives, antioxidants, and edible fat.

Example 8—Clinical Study Example I for PK Measure

Assessment of the present dosage forms of Pregn-4-ene-3,20-dione compositions relative to prior art composition in a single dose can be conducted based on actual results and/or simulated data from clinical studies reported in the literature and studies conducted by Applicant as a single-dose crossover design, wherein volunteers were randomized to six different treatments (Composition A, B, C, E: 200 mg, and Composition D and F: 95 mg) under fasting conditions. The pharmaceutical compositions comprising Pregn-4-ene-3,20-dione for this investigation are depicted in Table 7. The study population consisted of twelve (12) healthy non-smoking non-hysterectomized postmenopausal women 45 to 65 years of age with a BMI of 18-32 kg/m².

Venous blood samples were collected into evacuated vacuum collection tubes comprising sodium heparin as anticoagulant for the concentration measurement of plasma pregn-4-ene-3,20-dione and its metabolites at pre-dose (time −1.0, −0.5, and 0.0), 0.5, 1, 1.5, 2, 2.5, 3, 4, 5, 6, 8, 10, 12, 18, and 24 hours after dosing. Time 0 samples were collected within 30 minutes prior to the first study drug administration of each treatment period. Concentrations of pregn-4-ene-3, 20-dione, 3α-OH-5α-pregnan-20-one, 3α-OH-5β-pregnan-20-one, 3β-OH-5α-pregnan-20-one, and 3β-OH-5β-pregnan-20-one were measured using a chromatography combined mass spectrometry method (e.g., LC-MS/MS or GC-MS).

As a result, dosage forms of conventional compositions at 200 mg dose (Composition A, B, and C in Table 8) would not result in adequate levels of neurosteroid essential for $GABA_A$ modulating therapeutics. However, the dosage forms of the representative compositions (Composition D,

TABLE 8A

| | Composition % w/w | | | | | |
|---|---|---|---|---|---|---|
| Component | Comp. A | Comp. B | Comp. C | Comp. D | Comp. E | Comp. F |
| Pregn-4-ene-3,20-dione | 40.0 | 30.0 | 23.5 | 4.3 | 9.0 | 23.5 |
| Edible Oil (e.g., peanut oil) | 49.6 | — | — | — | — | — |
| Caprylic/capric glycerides (e.g., Capmul 708G, Capmul MCM) | — | 65.9 | — | — | — | — |
| Glyceryl monocaprylate (e.g., Capmul MCM C8) | — | — | — | 46.0 | 63.7 | 35.0 |
| Alpha-tocopherol | — | — | — | 2.5 | 20.5 | 20.5 |
| Sodium lauryl sulfate | — | — | 5.9 | — | — | 6.5 |
| Release modulator (e.g., Hydroxypropyl methylcellulose) | — | — | 57.7 | — | — | — |
| Polysorbate 80 | — | — | 1.0 | — | — | — |
| Lecithin | 0.4 | 1.1 | — | — | — | — |
| Lauroyl polyoxyl-32 glycerides (e.g., Gelucire 44/14) | — | 3.0 | — | — | — | — |
| Polyoxyl castor oil (e.g., Kolliphor EL, Kolliphor RH40) | — | — | — | 47.2 | 6.8 | 10.5 |
| Glyceryl distearate | — | — | — | — | — | 4.0 |
| Other carrier ingredients | q.s. | q.s. | q.s. | q.s. | q.s. | q.s. |

TABLE 8B

PK Parameters Post Single Dose Administration of Compositions

| | PK Values | | | | | |
|---|---|---|---|---|---|---|
| PK Parameters | Comp. A | Comp. B | Comp. C | Comp. D | Comp. E | Comp. F |
| Pregn-4-ene-3,20-dione | | | | | | |
| $C_{max}$, mean (ng/ml) | 3.0 | 3.3 | 1.0 | 6.2 | 7.5 | 4.7 |
| $T_{max}$, mean (hr) | 1.5 | 1.5 | 4.5 | 1.5 | 1.5 | 2.0 |
| 3α-OH-5β-pregnan-20-one | | | | | | |
| $C_{max}$, mean (ng/ml) | 10.0 | 10.5 | 2.1 | 26.7 | 31.8 | 20.4 |
| >11.0 ng/ml | No | No | No | Yes | Yes | Yes |
| <90.0 ng/ml | Yes | Yes | Yes | Yes | Yes | Yes |
| 3α-OH-5α-pregnan-20-one | | | | | | |
| $C_{max}$, mean (ng/ml) | 12.3 | 12.2 | 2.1 | 27.5 | 37.0 | 22.0 |
| >18.0 ng/ml | No | No | No | Yes | Yes | Yes |
| <90.0 ng/ml | Yes | Yes | Yes | Yes | Yes | Yes |
| 3β-OH-5α-pregnan-20-one | | | | | | |
| $C_{max}$, mean (ng/ml) >2.5 ng/ml | No | No | No | Yes | Yes | Yes |
| 3β-OH-5β-pregnan-20-one | | | | | | |
| $C_{max}$, mean (ng/ml) >2.0 ng/ml | No | No | No | Yes | Yes | Yes |
| Ratio of $C_{max}$/Dose Amount, /ml | | | | | | |
| 3α-OH-5α-pregnan-20-one/ Pregn-4-ene-3,20-dione | $6.2 \times 10^{-8}$ | $6.1 \times 10^{-8}$ | $1.1 \times 10^{-8}$ | $2.9 \times 10^{-7}$ | $1.9 \times 10^{-7}$ | $2.3 \times 10^{-7}$ |
| $>7.5 \times 10^{-8}$/ml | No | No | No | Yes | Yes | Yes |
| 3α-OH-5b-pregnan-20-one/ Pregn-4-ene-3,20-dione | $5.0 \times 10^{-8}$ | $5.3 \times 10^{-8}$ | $1.1 \times 10^{-8}$ | $2.8 \times 10^{-7}$ | $1.6 \times 10^{-7}$ | $1.1 \times 10^{-7}$ |
| $>5.0 \times 10^{-8}$/ml | No | Yes | No | Yes | Yes | Yes |
| (3α-OH-5a-pregnan-20-one + 3α-OH-5b-pregnan-20-one)/ Pregn-4-ene-3,20-dione | $1.1 \times 10^{-7}$ | $1.1 \times 10^{-7}$ | $2.2 \times 10^{-8}$ | $5.7 \times 10^{-7}$ | $3.5 \times 10^{-7}$ | $2.2 \times 10^{-7}$ |
| $>1.3 \times 10^{-7}$/ml | No | No | No | Yes | Yes | Yes |

E, and F in Table 8) resulted in efficient generation of levels adequate for $GABA_A$ modulating therapeutics with a lower dose or the equivalent dose. Furthermore, the dosage forms of the represented compositions resulted in a higher ratio of $C_{max}$/dose of PAMs (e.g., 3α-OH-5α-pregnan-20-one and/or 3α-OH-5b-pregnan-20-one)/Pregn-4-ene-3,20-dione than ones from the conventional compositions comprising crystalline form of Pregn-4-ene-3,20-dione (e.g., Composition A, B, and C).

Example 9—Clinical Study Example H for PK Measure

Assessment of effects of an inventive daily dose dosage form of the Pregn-4-ene-3,20-dione composition (e.g., composition 6-1 in Table 6) relative to a prior art composition (e.g., composition A in Table 8) in a single dose can be conducted and the PK results and/or simulated data from clinical studies reported in the literature and studies conducted by Applicant as a single-dose crossover design, wherein volunteers were randomized to six different treatments (40 mg, 80 mg, 120 mg Pregn-4-ene-3,20-dione of composition A in Table 8, and 40 mg, 80 mg, 120 mg Pregn-4-ene-3,20-dione of composition 6-1 in Table 6) without regard to meal. The pharmaceutical compositions comprising Pregn-4-ene-3,20-dione for this investigation are depicted in Table 8. The study population consisted of twelve (12) healthy non-smoking non-hysterectomized postmenopausal women 45 to 65 years of age with a BMI of 18-32 kg/m2.

The calculation of all pharmacokinetic parameters was based on the actual time for drug administration and blood sampling. The PK of analytes were measured using a chromatography combined mass spectrometry method (e.g., LC-MS/MS or GC-MS).

TABLE 9

| | Composition % w/w | |
| --- | --- | --- |
| Component | Composition A | Composition 6-1 |
| Pregn-4-ene-3,20-dione | 40.0 | 7.6 |
| Edible Oil (e.g., peanut oil) | 49.6 | — |
| Glyceryl monocaprylate (e.g., Capmul MCM C8) | — | 82.9 |
| Alpha-tocopherol | — | 4.6 |
| Lecithin | 0.4 | — |
| PEG-35 castor oil (e.g., Kolliphor EL) | — | 4.9 |
| Other carrier ingredients | q.s. | q.s. |

| | PK Parameters | | | | | |
| --- | --- | --- | --- | --- | --- | --- |
| Treatment | 1 | 2 | 3 | 4 | 5 | 6 |
| Daily dose amount of Pregn-4-ene-3,20-dione | 40 mg | 80 mg | 120 mg | 40 mg | 80 mg | 120 mg |
| Pregn-4-ene-3,20-dione | | | | | | |
| $C_{max}$, mean (ng/ml) | 0.7 | 1.3 | 1.8 | 2.2 | 3.5 | 5.3 |
| 3α-OH-5β-pregnan-20-one | | | | | | |
| $C_{max}$, mean (ng/ml) >6.0 ng/ml | 2.0 No | 4.0 No | 6.0 No | 6.4 Yes | 12.7 Yes | 19.1 Yes |
| 3α-OH-5α-pregnan-20-one | | | | | | |
| $C_{max}$, mean (ng/ml) >8.0 ng/ml | 2.5 No | 4.9 No | 7.4 No | 8.5 Yes | 14.8 Yes | 22.2 Yes |
| 3β-OH-5α-pregnan-20-one | | | | | | |
| $C_{max}$, mean (ng/ml) >2.5 ng/ml | No | No | No | Yes | Yes | Yes |
| 3β-OH-5β-pregnan-20-one | | | | | | |
| $C_{max}$, mean (ng/ml) >2.0 ng/ml | No | No | No | Yes | Yes | Yes |
| Ratio of $C_{max}$/Daily Dose Amount | | | | | | |
| 3α-OH-5α-pregnan-20-one/Pregn-4-ene-3,20-dione | | | | | | |
| >7.5 × $10^{-8}$/ml | No | No | No | Yes | Yes | Yes |
| 3α-OH-5β-pregnan-20-one/Pregn-4-ene-3,20-dione | | | | | | |
| >5.0 × $10^{-8}$/ml | No | No | No | Yes | Yes | Yes |
| (3α-OH-5α-pregnan-20-one + 3α-OH-5β-pregnan-20-one)/Pregn-4-ene-3,20-dione | | | | | | |
| >1.3 × $10^{-7}$/ml | No | No | No | Yes | Yes | Yes |

A dosage form of conventional compositions (e.g., composition A) at varying doses failed to result in adequate levels of neurosteroid essential for $GABA_A$ modulating therapeutics. However, the dosage forms of the representative inventive compositions (e.g., composition 6-1) with various doses resulted in efficient generation of levels adequate for $GABA_A$ modulating therapeutics at the equivalent dose of pregn-4-ene-3,20-dione of the conventional composition (e.g., composition A). Furthermore, the dosage forms of the represented inventive compositions resulted in higher levels at the assessed dose than ones obtained with composition A (micronized pregn-4-ene-3,20-dione) at all study doses. This is, besides compositional differences and/or release rate differences, possibly due to a difference in predominance of containing crystalline form of pregn-4-ene-3,20-dione in composition A versus predominance of non-crystalline forms (partially or fully solubilized and/or amorphous form of pregn-4-ene-3,20-dione) in the present composition (composition 6-1).

Example 10—Clinical Study Design for Pharmacodynamic Effect in Women with Postpartum Depression The pilot study entails a randomized, placebo-controlled, double-blind study with five arms to assess treatment potential in women with of CNS depressive disorder, such as postpartum depression (PPD). The study arms are following as:

Treatment 1: A 45 mg daily dose capsule of pregn-4-ene-3,20-dione of composition 6-3
Treatment 2: A 90 mg daily dose capsule of pregn-4-ene-3,20-dione of composition 6-3
Treatment 3: A 20 mg daily dose capsule of pregn-4-ene-3,20-dione of composition A (micronized administration)
Treatment 4: A 200 mg daily dose capsule of pregn-4-ene-3,20-dione of composition A (micronized administration)
Treatment 5: A placebo capsule matching composition 6-3

Changes from baseline of HAM-D total, Saccadic Eye Movements, and Mood Rating Score (MRS) can be measured to evaluate the effect of the test drugs on treatment of CNS disorder in women with child-bearing age. The test drugs and placebo are administered in a fasted condition for fourteen days. Subjects are followed for 7 days following the last dose of study drug (Day 21).

The study can comprise 5 scheduled visits. Visit 1 is for screening and determining preliminary study eligibility. At Visit 2, Days 1-4, subjects are randomized and confined following study drug administration through the morning on Day 4. Subjects undergo safety monitoring, intensive pharmacokinetic (PK) sampling of pregn-4-ene-3,20-dione and its metabolites, and monitoring depression symptoms. On Day 4, at the discretion of the Principal Investigator (PI) subjects may leave confinement for the remainder of the study treatment (Day 15), or the confinement stay may be extended. At Visits 3 and 4, Days 8 and 15 respectively, subjects return to the clinic for safety monitoring and measuring of depression symptoms. A follow-up visit (Visit 5) occurs Day 21, where End of Study (EOS) procedures is performed, and subjects exit from the trial.

Table 10 shows treatment effect of the present test composition (Composition 6-3) with two different daily doses and a conventional composition (Composition A) compared to the placebo on change from baseline in the HAM-D total score, Saccadic Eye Movements, and Mood Rating Score at Days 8.

TABLE 10

Treatment effect of the present oral compositions on changes of HAM-D, SEV, and MRS from baseline

| Treatment | Formulation | Daily Dose | Mean baseline score | HAM-D Total Score** Mean CBL† (Std. error) | Placebo-adjusted mean decrease | SEV (Mean CBL, deg/s)* | Saccadic Eye Movement & Mood Rating Scale** Sedation (Mean CBL, mm) | Calmness (Mean CBL, mm) |
|---|---|---|---|---|---|---|---|---|
| | | | | Day 8 | | | | |
| 1 | Composition 6-3 | 45 mg | >20 | -14.3 (1.2) | >2 | -30 | -55 | -18 |
| 2 | Composition 6-3 | 90 mg | >20 | -15.1 (1.2) | >3 | <-40 | <-80 | <-20 |
| 3 | Composition A (Micronized form) | 20 mg | >20 | -12.1 (1.1) | <1 | -22 | -22 | -11 |
| 4 | Composition A (Micronized form) | 200 mg | >20 | -12.7 (1.2) | <1 | -25 | -35 | -15 |
| 5 | Placebo | — | >20 | -12.0 (1.1) | — | -20 | -20 | -10 |

*Saccadic Eye Movement is measured by saccadic eye velocity (SEV) in deg/s.
**Results were obtained by simulation based on data from conducted clinical study results of HAM-D, Saccadic Eye Velocity (SEV), and Mood Rating Scale (MRS) reported in the literature.
†CBL: Change from baseline As a result, the dosage form of the conventional composition at two different doses of pregn-4-ene-3,20-dione (20 mg/day and 200 mg/day) upon micronized administration failed to show effective results for treatment of CNS disorder (e.g., changes from baseline of HAM-D) and/or CNS activity (e.g., SEV and MRS), whereas the present representative composition (composition 6-3) with two different doses of pregn-4-ene-3,20-dione (45 mg/day and 90 mg/day) suggested significant and meaningful changes towards a treatment for CNS depression disorder from baseline and greater changes compared to the placebo.

It is understood that the above-described various types of compositions, dosage forms methods and/or modes of applications are only illustrative of various invention embodiments. Numerous modifications and alternative arrangements may be devised by those skilled in the art without departing from the spirit and scope of the present disclosure and the appended claims are intended to cover such modifications and arrangements. Thus, while invention embodiments have been described above with particularity and detail, it will be apparent to those of ordinary skill in the art that variations including, but not limited to, variations in size, materials, shape, form, function and manner of operation, assembly and use may be made without departing from the principles and concepts set forth herein.

What is claimed is:

1. A method of treating depression in a subject comprising orally administering to the subject an amount of a composition containing pregn-4-ene-3,20-dione in an at least partially solubilized or non-crystalline form that provides at least one of the following ratios comprising:
a $C_{max}$ of 3α-OH-5β-pregnan-20-one/dose of pregn-4-ene-3,20-dione of from about $5.0 \times 10^{-8}$/ml to about $2.5 \times 10^{-6}$/ml,
a $C_{max}$ of 3α-OH-5α-pregnan-20-one/dose of pregn-4-ene-3,20-dione of from about $7.5 \times 10^{-8}$/ml to about $2.5 \times 10^{6}$/ml,
a sum of $C_{max}$ of (3α-OH-5α-pregnan-20-one and 3α-OH-5β-pregnan-20-one)/dose of pregn-4-ene-3,20-dione of from about $1.3 \times 10^{-7}$/ml to about $5.0 \times 10^{-6}$/ml,
a $C_{max}$ of 3α-OH-5α-pregnan-20-one of greater than about 10 ng/ml,
a $C_{max}$ of 3α-OH-5β-pregnan-20-one of greater than about 6 ng/ml,
a ratio of $C_{max}/C_{max}$ of 3α-OH-5α-pregnan-20-one/pregn-4-ene-3,20-dione of from about 2.0 to about 50,
a ratio of $C_{max}/C_{max}$ of 3α-OH-5β-pregnan-20-one/pregn-4-ene-3,20-dione of from about 1.0 to about 50, and
a ratio of $C_{max}/C_{max}$ of (3α-OH-5α-pregnan-20-one and 3α-OH-5β-pregnan-20-one)/pregn-4-ene-3,20-dione of from about 3 to about 100,
wherein at least one of said serum levels is greater than a serum level resulting from a micronized administration, and
wherein said administration comprises a plurality of doses of said composition administered at a frequency of at least four hours apart.

2. The method of claim 1, wherein said subject comprises a male, a premenopausal female, a perimenopausal female, a postmenopausal female, a pregnant female, or a postpartum female.

3. The method of claim 1, wherein said pregn-4-ene-3,20-dione is combined with a pharmaceutically acceptable carrier to form an oral pharmaceutical composition comprising at least one of from about 0.06 wt % to about 25 wt % and from about 3 wt % to 10 wt % of said pregn-4-ene-3,20-dione.

4. The method of claim 3, wherein said carrier comprises at least one of a hydrophilic additive, a lipophilic additive, and a combination thereof, and wherein said carrier comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, PEG-35 castor oil, PEG-40 hydrogenated castor oil, polysorbate 80, polysorbate 20, polyglyceryl-10 monooleate, polyglyceryl-dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, and a combination thereof and wherein said lipophilic additive comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, and a combination thereof and wherein said hydrophilic additive comprises at least one of PEG-35 castor oil, PEG-40 hydrogenated castor oil, polysorbate 80, polysorbate 20, polyglyceryl-10 monooleate, polyglyceryl-10 dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, lauroyl PEG-32 glyceride, and a combination thereof.

5. The method of claim 3, wherein from about 50% to about 100% of the pregn-4-ene-3,20-dione is solubilized in said carrier, and wherein said composition comprises an oral dosage form having at least one of from about 10 mg to about 400 mg of said pregn-4-ene-3,20-dione and from about 25 mg to 100 mg of said pregn-4-ene-3,20-dione.

6. The method of claim 1, wherein a daily dose of said pregn-4-ene-3,20-dione comprises from about 10 mg to about 3400 mg, and
wherein said administration provides at least one of:
a $T_{max}$ for 3α-OH-5β-pregnan-20-one in at least one of less than about 1.5 hours, less than about 2 hours, less than about 3 hours, and less than about 4 hours post-administration;
a reduction in $C_{max}$ level to one half of a $C_{max}$ level for 3α-OH-5β-pregnan-20-one within at least one of about 1 hour, about 2 hours, about 3 hours, about 4 hours, and about 5 hours post-$T_{max}$; and
treatment that occurs within in at least one of less than about 1 hour, less than 2 hours, greater than about 2 hours, greater than 4 hours, greater than 8 hours, greater than about 24 hours, greater than about 2 days, greater than about 3 days, greater than about 4 days, greater than about 5 days, greater than about 6 days, greater than about 7 days, greater than about 8 days, greater than about 14 days, and greater than about 28 days post-administration, and,
wherein said administration results in a reduction of a 17-item HAM-D score in said subject as compared to at least one of a placebo and a baseline by at least one of about 2, about 3, about 4, about 5, about 6, about 7, about 8, about 9, about 10, about 10, about 11, about 12, about 13, about 14, about 15, about 16, about 17, about 18, about 16, and about 20 when measured at from about 3 days to about 30 days after commencement of treatment.

7. The method of claim 1, wherein said composition comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and an injectable, and wherein said drink comprises at least one of a flavoring agent, a sweetener, an antimicrobial preservative, an antioxidant, and edible fat, and wherein said drink comprises a volume of about 15 mL to about 90 mL, and wherein said drink comprises at least one of about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, of said pregn-4-ene-3,20-dione.

8. A method of treating depression comprising:
orally administering to a subject an oral pharmaceutical composition comprising pregn-4-ene-3,20-dione in an at least partially solubilized or non-crystalline form and a pharmaceutically acceptable carrier, which provides in said subject, as compared to a substantially equivalent amount of a micronized administration administered to said subject, at least one of:
a serum level $C_{max}$ of 3α-OH-5α-pregnan-20-one,
a serum level $C_{max}$ of 3α-OH-5β-pregnan-20-one,
a serum level $C_{avg}$ of 3α-OH-5α-pregnan-20-one, and
a serum level $C_{avg}$ of 3α-OH-5β-pregnan-20-one,
that is greater than a serum level provided by said micronized administration,
wherein at least one of said serum levels is greater than a serum level resulting from a micronized administration, and
wherein said administration comprises a plurality of doses of said composition administered at a frequency of at least four hours apart.

9. The method of claim 8, wherein said subject comprises a male or a female, and wherein said female comprises at least one of a pregnant female, a postpartum female who has given birth within at least one of one month, six months, and twelve months, a premenopausal female, a perimenopausal female, and a postmenopausal female.

10. The method of claim 8, wherein said pregn-4-ene-3,20-dione comprises at least one of from about 0.06 wt % to about 25 wt % and from about 3 wt % to 10 wt % of said composition, and wherein said pregn-4-ene-3,20-dione comprises at least one of a substantially non-crystalline form and a substantially solubilized form.

11. The method of claim 8, wherein said carrier comprises at least one of a hydrophilic additive, a lipophilic additive, and a combination thereof, and wherein said carrier comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, PEG-35 castor oil, PEG-40 hydrogenated castor oil, polysorbate 80, polysorbate 20, polyglyceryl-10 monooleate, polyglyceryl-dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, and a combination thereof, and wherein said lipophilic additive comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, and a combination thereof, and wherein said hydrophilic additive comprises at least one of PEG-35 castor oil, PEG-40 hydrogenated castor oil, polysorbate 80, polysorbate 20, polyglyceryl-10 monooleate, polyglyceryl-dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, lauroyl PEG-32 glyceride, and a combination thereof.

12. The method of claim 8, wherein a daily dose of said pregn-4-ene-3,20-dione comprises from about 10 mg to about 3400 mg, and
wherein said administration provides at least one of:
a $T_{max}$ for at least one of 3α-OH-5α-pregnan-20-one, 3α-OH-5β-pregnan-20-one, and a combination thereof in at least one of less than about 1.5 hours, less than about 2 hours, less than about 3 hours, and less than about 4 hours post-administration;
a reduction in $C_{max}$ level to one half of a $C_{max}$ level for at least one of 3α-OH-5α-pregnan-20-one and 3α-OH-5β-pregnan-20-one within at least one of about 1 hour, about 2 hours, about 3 hours, about 4 hours, and about 5 hours post-$T_{max}$; and
treatment that occurs within in at least one of less than about 1 hour, less than 2 hours, greater than about 2 hours, greater than 4 hours, greater than 8 hours, greater than about 24 hours, greater than about 2 days, greater than about 3 days, greater than about 4 days, greater than about 5 days, greater than about 6 days, greater than about 7 days, greater than about 8 days, greater than about 14 days, and greater than about 28 days post-administration, and
wherein said administration results in a reduction of a 17-item HAM-D score in said subject as compared to at least one of a placebo and a baseline by at least one of about 2, about 3, about 4, about 5, about 6, about 7, about 8, about 9, about 10, about 10, about 11, about 12, about 13, about 14, about 15, about 16, about 17, about 18, about 16, and about 20 when measured at from about 3 days to about 30 days after commencement of treatment.

13. The method of claim 8, wherein said composition comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and an injectable, and wherein said drink comprises at least one of a flavoring agent, a sweetener, an antimicrobial preservative, an antioxidant, and edible fat, and wherein said drink comprises a volume of about 15 mL to about 90 mL, and wherein said drink comprises at least one of about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, of said pregn-4-ene-3,20-dione.

14. A method of treating depression comprising:
orally administering to a subject an oral pharmaceutical composition comprising pregn-4-ene-3,20-dione in an at least partially solubilized or non-crystalline form and a pharmaceutically acceptable carrier, which provides in said subject, as compared to a substantially equivalent amount of a micronized administration administered to said subject, a plurality of:
a serum level $C_{max}$ of 3α-OH-5α-pregnan-20-one,
a serum level $C_{max}$ of 3α-OH-5β-pregnan-20-one,
a serum level $C_{avg}$ of 3α-OH-5α-pregnan-20-one, and
a serum level $C_{avg}$ of 3α-OH-5β-pregnan-20-one,
that are greater than a serum level provided by said micronized administration,
wherein at least one of said serum levels is greater than a serum level resulting from a micronized administration, and wherein said administration comprises a plurality of doses of said composition administered at a frequency of at least four hours apart.

15. The method of claim 14, wherein said subject comprises a male or a female, and wherein said female comprises at least one of a pregnant female, a postpartum female who has given birth within at least one of one month, six months, and twelve months, a premenopausal female, a perimenopausal female, and a postmenopausal female.

16. The method of claim 14, wherein said pregn-4-ene-3,20-dione comprises at least one of from about 0.06 wt % to about 25 wt % and from about 3 wt % to 10 wt % of said composition, and wherein said pregn-4-ene-3,20-dione comprises at least one of a substantially non-crystalline form and a substantially solubilized form.

17. The method of claim 14, wherein said carrier comprises at least one of a hydrophilic additive, a lipophilic additive, and a combination thereof, and wherein said carrier comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, PEG-35 castor oil, PEG-40 hydrogenated castor oil, polysorbate 80, polysorbate 20, polyglyceryl-10 monooleate, polyglyceryl-dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, and a combination thereof, and wherein said lipophilic additive comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, and a combination thereof, and wherein said hydrophilic additive comprises at least one of PEG-35 castor oil, PEG-40 hydrogenated castor oil, polysorbate 80, polysorbate 20, polyglyceryl-10 monooleate, polyglyceryl-dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, lauroyl PEG-32 glyceride, and a combination thereof.

18. The method of claim 14, wherein a daily dose of said pregn-4-ene-3,20-dione comprises from about 10 mg to about 3400 mg, and
wherein said administration provides at least one of:
a $T_{max}$ for at least one of 3α-OH-5α-pregnan-20-one, 3α-OH-5β-pregnan-20-one, and a combination thereof in at least one of less than about 1.5 hours, less than about 2 hours, less than about 3 hours, and less than about 4 hours post-administration;
a reduction in $C_{max}$ level to one half of a $C_{max}$ level for at least one of 3α-OH-5α-pregnan-20-one and 3α-OH-5β-pregnan-20-one within at least one of about 1 hour, about 2 hours, about 3 hours, about 4 hours, and about 5 hours post-$T_{max}$; and
treatment that occurs within in at least one of less than about 1 hour, less than 2 hours, greater than about 2 hours, greater than 4 hours, greater than 8 hours, greater than about 24 hours, greater than about 2 days, greater than about 3 days, greater than about 4 days, greater than about 5 days, greater than about 6 days, greater than about 7 days, greater than about 8 days, greater than about 14 days, and greater than about 28 days post-administration, and
wherein said administration results in a reduction of a 17-item HAM-D score in said subject as compared to at least one of a placebo and a baseline by at least one of about 2, about 3, about 4, about 5, about 6, about 7, about 8, about 9, about 10, about 10, about 11, about 12, about 13, about 14, about 15, about 16, about 17, about 18, about 16, and about 20 when measured at from about 3 days to about 30 days after commencement of treatment.

19. The method of claim 14, wherein said composition comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and an injectable, and wherein said drink comprises at least one of a flavoring agent, a sweetener, an antimicrobial preservative, an antioxidant, and edible fat, and wherein said drink comprises a volume of about 15 mL to about 90 mL, and wherein said drink comprises at least one of about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, of said pregn-4-ene-3,20-dione.

20. A method of treating depression in a subject comprising orally administering to the subject a daily dose of about 10 mg to about 3400 mg of a composition containing pregn-4-ene-3,20-dione in an at least partially solubilized or non-crystalline form that provides at least one of the following values comprising:
a serum level $C_{max}$ of 3α-OH-5α-pregnan-20-one of greater than about 10 ng/ml,
a serum level $C_{max}$ of 3α-OH-5β-pregnan-20-one of greater than about 6 ng/ml,
a ratio of $C_{max}/C_{max}$ of 3α-OH-5α-pregnan-20-one/pregn-4-ene-3,20-dione of from about 2.0 to about 50,
a ratio of $C_{max}/C_{max}$ of 3α-OH-5β-pregnan-20-one/pregn-4-ene-3,20-dione of from about 1.0 to about 50, and
a ratio of $C_{max}/C_{max}$ of (3α-OH-5α-pregnan-20-one and 3α-OH-5β-pregnan-20-one)/pregn-4-ene-3,20-dione of from about 3 to about 100,
wherein at least one of said serum levels is greater than a serum level resulting from a micronized administration, and
wherein said administration comprises a plurality of doses of said composition administered at a frequency of at least four hours apart.

21. The method of claim 20, wherein said pregn-4-ene-3,20-dione is combined with a pharmaceutically acceptable carrier to form an oral pharmaceutical composition comprising at least one of from about 0.06 wt % to about 25 wt % and from about 3 wt % to 10 wt % of said pregn-4-ene-3,20-dione, and wherein said carrier comprises at least one of a hydrophilic additive, a lipophilic additive, and a combination thereof.

22. The method of claim 21, wherein said carrier comprises at least one of alpha-tocopherol, glyceryl monocaprylate, glyceryl mono and dicaprylocaprate, propylene glycol monolaurate, propylene glycol monocaprylate, peppermint oil, caprylic acid, oleic acid, castor oil, linoleic acid, steric acid, glyceryl distearate, sorbitan monolaurate, sorbitan monooleate, Linoleoyl Polyoxyl-6 glycerides, polyglyceryl 3-oleate, lauroyl PEG-32 glycerides, oleoyl polyoxyl-6 glyceride, omega-3 esters/derivatives, PEG-35 castor oil, PEG-40 hydrogenated castor oil, polysorbate 80, polysorbate 20, polyglyceryl-10 monooleate, polyglyceryl-10 dioleate, polyglyceryl-10 monocaprylate, polyglyceryl-10 dicaprylate, glyceryl-10 caprylate/caprate, glyceryl-10 monocaprate, caprylocaproyl polyoxyl-8 glyceride, tocopherol polyethylene glycol succinate, and a combination thereof.

23. The method of claim 21, wherein from about 50% to about 100% of the pregn-4-ene-3,20-dione is solubilized in said carrier, and wherein said composition comprises an oral dosage form having at least one of from about 10 mg to about 400 mg of said pregn-4-ene-3,20-dione and from about 25 mg to 100 mg of said pregn-4-ene-3,20-dione.

24. The method of claim 20, wherein said administration provides at least one of:
   a $T_{max}$ for 3α-OH-5α-pregnan-20-one in at least one of less than about 1.5 hours, less than about 2 hours, less than about 3 hours, and less than about 4 hours post-administration;
   a reduction in $C_{max}$ level to one half of a $C_{max}$ level for 3α-OH-5α-pregnan-20-one within at least one of about 1 hour, about 2 hours, about 3 hours, about 4 hours, and about 5 hours post-$T_{max}$;
   treatment that occurs within in at least one of less than about 1 hour, less than 2 hours, greater than about 2 hours, greater than 4 hours, greater than 8 hours, greater than about 24 hours, greater than about 2 days, greater than about 3 days, greater than about 4 days, greater than about 5 days, greater than about 6 days, greater than about 7 days, greater than about 8 days, greater than about 14 days, and greater than about 28 days after commencement of treatment; and
   a reduction of a 17-item HAM-D score in said subject as compared to at least one of a placebo and a baseline by at least one of about 2, about 3, about 4, about 5, about 6, about 7, about 8, about 9, about 10, about 10, about 11, about 12, about 13, about 14, about 15, about 16, about 17, about 18, about 16, and about 20 when measured at from about 3 days to about 30 days after commencement of treatment.

25. The method of claim 20, wherein said composition comprises at least one of a tablet, a capsule, a caplet, a gelcap, a suspension, a solution, a drink, a gel, a syrup, a dispersion, an emulsion, a sprinkle, a lozenge, a microemulsion, a nanoemulsion, an elixir, a paste, a powder, and a granule, and an injectable, and wherein said drink comprises at least one of a flavoring agent, a sweetener, an antimicrobial preservative, an antioxidant, and edible fat, and wherein said drink comprises a volume of about 15 mL to about 90 mL, and wherein said drink comprises at least one of about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, of said pregn-4-ene-3,20-dione.

26. The method of claim 20, wherein said depression comprises perinatal depression, and wherein said subject comprises at least one of a pregnant female and a female who has given birth within at least one of one month, six months, and twelve months.

\* \* \* \* \*